US009283076B2

(12) United States Patent
Sikora et al.

(10) Patent No.: US 9,283,076 B2
(45) Date of Patent: Mar. 15, 2016

(54) GLENOID RESURFACING SYSTEM AND METHOD

(75) Inventors: George Sikora, Bridgewater, MA (US); Steven W. Ek, Bolton, MA (US)

(73) Assignee: Arthrosurface Incorporated, Franklin, MA (US)

(*) Notice: Subject to any disclaimer, the term of this patent is extended or adjusted under 35 U.S.C. 154(b) by 518 days.

(21) Appl. No.: 12/762,920

(22) Filed: Apr. 19, 2010

(65) Prior Publication Data

US 2010/0268238 A1 Oct. 21, 2010

Related U.S. Application Data

(60) Provisional application No. 61/170,290, filed on Apr. 17, 2009, provisional application No. 61/311,605, filed on Mar. 8, 2010.

(51) Int. Cl.
*A61F 5/00* (2006.01)
*A61F 2/30* (2006.01)
(Continued)

(52) U.S. Cl.
CPC ......... *A61F 2/30756* (2013.01); *A61B 17/1684* (2013.01); *A61F 2/4081* (2013.01); *A61F 2/4612* (2013.01); *A61B 17/1604* (2013.01); *A61B 2017/1778* (2013.01); *A61F 2002/30112* (2013.01); *A61F 2002/30233* (2013.01); *A61F 2002/30616* (2013.01); *A61F 2002/30818* (2013.01); *A61F 2002/30879* (2013.01); *A61F 2002/30881* (2013.01); *A61F 2002/30883* (2013.01); *A61F 2002/30884* (2013.01); *A61F 2002/4687* (2013.01); *A61F 2230/0004* (2013.01); *A61F 2230/0069* (2013.01); *A61F 2250/0064* (2013.01)

(58) Field of Classification Search
USPC ............................................ 606/87, 96, 104
See application file for complete search history.

(56) References Cited

U.S. PATENT DOCUMENTS 103,645 A 5/1870 Muscroft
992,819 A 5/1911 Springer
(Continued)

FOREIGN PATENT DOCUMENTS

AU 2001262308 12/2001
AU 2001259327 B2 2/2005
(Continued)

OTHER PUBLICATIONS

United States Office Action issued is related U.S. Appl. No. 10/760,965 dated Feb. 19, 2008.
(Continued)

*Primary Examiner* — Sameh Boles
(74) *Attorney, Agent, or Firm* — Grossman Tucker Perreault & Pfleger PLLC

(57) ABSTRACT

A system and method for repairing a defect on an articular surface. An excision guide is positioned on an articular surface, wherein the excision guide includes a guide head and a guide sleeve disposed on the guide head, wherein the guide head includes a contact surface configured to locate the excision guide relative to the articular surface. A guide pin may be advanced through the guide sleeve and secured to the articular surface, wherein the guide sleeve is configured to receive the guide pin therethrough and position the guide pin at an angle β relative to an axis generally normal and central to a defect on the articular surface, wherein angle β is less than 90 degrees.

17 Claims, 25 Drawing Sheets

49
108
104
112
54
116
50
58
110
55
52

(51) Int. Cl.
*A61F 2/40* (2006.01)
*A61F 2/46* (2006.01)
*A61B 17/16* (2006.01)
*A61B 17/17* (2006.01)

(56) References Cited

U.S. PATENT DOCUMENTS 1,451,610 A 4/1923 Gestas
2,267,925 A 12/1941 Johnston
2,379,984 A 7/1943 Nereaux
2,381,102 A 10/1943 Boyd
2,570,465 A 10/1951 Lundholm
3,176,395 A 4/1965 Warner et al.
3,351,115 A 11/1967 Boehlow
3,715,763 A 2/1973 Link
3,840,905 A 10/1974 Deane
3,852,830 A 12/1974 Marmor
4,016,651 A 4/1977 Kawahara et al.
4,016,874 A 4/1977 Maffei et al.
4,034,418 A 7/1977 Jackson et al.
D245,259 S 8/1977 Shen
4,044,464 A 8/1977 Schiess et al.
4,158,894 A 6/1979 Worrell
4,304,011 A 12/1981 Whelan, III
4,309,778 A 1/1982 Buechel et al.
4,319,577 A 3/1982 Bofinger et al.
4,330,891 A 5/1982 Brånemark et al.
4,340,978 A 7/1982 Buechel et al.
4,344,192 A 8/1982 Imbert
4,433,687 A 2/1984 Burke et al.
4,462,120 A 7/1984 Rambert et al.
4,474,177 A 10/1984 Whiteside
4,484,570 A 11/1984 Sutter et al.
4,531,517 A 7/1985 Forte et al.
4,535,768 A 8/1985 Hourahane et al.
4,565,768 A 1/1986 Nonogaki et al.
4,567,885 A 2/1986 Androphy
4,634,720 A 1/1987 Dorman et al.
4,655,752 A 4/1987 Honkanen et al.
4,661,536 A 4/1987 Dorman et al.
4,662,371 A 5/1987 Whipple et al.
4,664,669 A 5/1987 Ohyabu et al.
4,673,407 A 6/1987 Martin
4,693,986 A 9/1987 Vit et al.
4,708,139 A 11/1987 Dunbar, IV
4,712,545 A 12/1987 Honkanen
4,714,478 A 12/1987 Fischer
4,719,908 A 1/1988 Averill et al.
4,722,331 A 2/1988 Fox
4,729,761 A 3/1988 White
4,778,473 A 10/1988 Matthews et al.
4,781,182 A 11/1988 Purnell et al.
4,787,383 A 11/1988 Kenna
4,788,970 A 12/1988 Kara et al.
4,823,780 A 4/1989 Odensten et al.
4,842,604 A 6/1989 Dorman et al.
4,896,663 A 1/1990 Vandewalls
4,911,153 A 3/1990 Border
4,911,720 A 3/1990 Collier
4,919,671 A 4/1990 Karpf
4,920,958 A 5/1990 Walt et al.
4,927,421 A 5/1990 Goble et al.
4,936,853 A 6/1990 Fabian et al.
4,938,778 A 7/1990 Ohyabu et al.
4,940,467 A 7/1990 Tronzo
4,945,904 A 8/1990 Bolton et al.
4,955,916 A 9/1990 Carignan et al.
4,976,037 A 12/1990 Hines
4,978,258 A 12/1990 Lins
4,979,957 A 12/1990 Hodorek
4,989,110 A 1/1991 Zevin et al.
4,990,163 A 2/1991 Ducheyne et al.
4,997,434 A 3/1991 Seedhorn et al.
4,998,938 A 3/1991 Ghajar et al.
5,007,930 A 4/1991 Dorman et al.
5,019,104 A 5/1991 Whiteside et al.
5,030,219 A 7/1991 Matsen, III et al.
5,053,049 A 10/1991 Campbell
5,092,895 A 3/1992 Albrektsson et al.
5,100,405 A 3/1992 McLaren
5,122,144 A 6/1992 Bert et al.
5,127,413 A 7/1992 Ebert
5,127,920 A 7/1992 MacArthur
5,147,386 A 9/1992 Carignan et al.
5,152,797 A 10/1992 Luckman et al.
5,154,720 A 10/1992 Trott et al.
5,180,384 A 1/1993 Mikhail
5,192,291 A 3/1993 Pannek, Jr.
5,194,066 A 3/1993 Van Zile
5,201,881 A 4/1993 Evans
5,207,753 A 5/1993 Badrinath
5,211,647 A 5/1993 Schmieding
5,224,945 A 7/1993 Pannek, Jr.
5,234,435 A 8/1993 Seagrave, Jr.
5,254,119 A 10/1993 Schreiber
5,255,838 A 10/1993 Gladdish, Jr. et al.
5,263,498 A 11/1993 Caspari et al.
5,263,987 A 11/1993 Shah
5,282,863 A 2/1994 Burton
5,290,313 A 3/1994 Heldreth
5,312,411 A 5/1994 Steele
5,314,478 A 5/1994 Oka et al.
5,314,482 A 5/1994 Goodfellow et al.
5,324,295 A 6/1994 Shapiro
5,326,366 A 7/1994 Pascarella et al.
5,336,224 A 8/1994 Selman
5,336,266 A 8/1994 Caspari et al.
5,354,300 A 10/1994 Goble et al.
5,358,525 A 10/1994 Fox et al.
5,360,446 A 11/1994 Kennedy
5,374,270 A 12/1994 McGuire et al.
5,383,937 A 1/1995 Mikhail
5,387,218 A 2/1995 Meswania
5,395,376 A 3/1995 Caspari et al.
5,395,401 A 3/1995 Bahler
5,409,490 A 4/1995 Ethridge
5,409,494 A 4/1995 Morgan
5,413,608 A 5/1995 Keller
5,423,822 A 6/1995 Hershberger
5,423,823 A 6/1995 Schmieding
5,425,733 A 6/1995 Schmieding
5,458,643 A 10/1995 Oka et al.
5,480,443 A 1/1996 Elias
5,486,178 A 1/1996 Hodge
5,509,918 A 4/1996 Romano
5,514,139 A 5/1996 Goldstein et al.
5,520,695 A 5/1996 Luckman
5,522,900 A 6/1996 Hollister
5,534,031 A 7/1996 Matsuzaki et al.
5,540,696 A 7/1996 Booth, Jr. et al.
5,562,664 A 10/1996 Durlacher et al.
5,580,352 A 12/1996 Sekel
5,580,353 A 12/1996 Mendes et al.
5,591,170 A 1/1997 Spievack et al.
5,593,448 A 1/1997 Dong
5,593,450 A 1/1997 Scott et al.
5,595,193 A 1/1997 Walus et al.
5,597,273 A 1/1997 Hirsch
5,601,550 A 2/1997 Esser
5,607,480 A 3/1997 Beaty
5,616,146 A 4/1997 Murray
5,620,055 A 4/1997 Javerlhac
5,624,463 A 4/1997 Stone et al.
5,632,745 A 5/1997 Schwartz
5,634,927 A 6/1997 Houston et al.
5,645,598 A 7/1997 Brosnahan, III
5,681,311 A 10/1997 Foley et al.
5,681,320 A 10/1997 McGuire
5,682,886 A 11/1997 Delp et al.
5,683,400 A 11/1997 McGuire
5,683,465 A 11/1997 Shinn et al.
5,683,466 A 11/1997 Viatle
5,700,264 A 12/1997 Zucherman et al.
5,700,265 A 12/1997 Romano

(56) References Cited

U.S. PATENT DOCUMENTS 5,702,401 A 12/1997 Shaffer
5,702,465 A 12/1997 Burkinshaw
5,702,467 A 12/1997 Gabriel et al.
5,741,266 A 4/1998 Moran et al.
5,765,973 A 6/1998 Hirsch et al.
5,769,855 A 6/1998 Bertin et al.
5,769,899 A 6/1998 Schwartz et al.
5,771,310 A 6/1998 Vannah
5,776,137 A 7/1998 Katz
5,782,835 A 7/1998 Hart et al.
5,800,440 A 9/1998 Stead
5,810,851 A 9/1998 Yoon
5,816,811 A 10/1998 Beaty
5,817,095 A 10/1998 Smith
5,824,087 A 10/1998 Aspden et al.
5,824,105 A 10/1998 Ries et al.
RE36,020 E 12/1998 Moore et al.
5,879,396 A 3/1999 Walston et al.
5,882,350 A 3/1999 Ralph et al.
5,885,297 A 3/1999 Matsen, III
5,885,298 A 3/1999 Herrington et al.
5,888,210 A 3/1999 Draenert
5,893,889 A 4/1999 Harrington
5,895,390 A 4/1999 Moran et al.
5,911,126 A 6/1999 Massen
5,918,604 A 7/1999 Whelan
5,919,196 A 7/1999 Bobic et al.
5,928,239 A 7/1999 Mirza
5,928,241 A 7/1999 Menut et al.
5,928,286 A 7/1999 Ashby et al.
5,964,752 A 10/1999 Stone
5,964,768 A 10/1999 Huebner
5,964,808 A 10/1999 Blaha et al.
5,968,050 A 10/1999 Torrie
5,989,269 A 11/1999 Vibe-Hansen et al.
5,990,382 A 11/1999 Fox
5,997,543 A 12/1999 Truscott
5,997,582 A 12/1999 Weiss
6,004,323 A 12/1999 Park et al.
6,010,502 A 1/2000 Bagby
6,015,411 A 1/2000 Ohkoshi et al.
6,017,348 A 1/2000 Hart et al.
6,019,767 A 2/2000 Howell
6,019,790 A 2/2000 Holmberg et al.
6,033,410 A 3/2000 McLean et al.
6,045,554 A 4/2000 Grooms et al.
6,045,564 A 4/2000 Walen
6,052,909 A 4/2000 Gardner
6,059,831 A 5/2000 Braslow
6,069,295 A 5/2000 Leitao
6,071,310 A 6/2000 Picha et al.
6,081,741 A 6/2000 Hollis
6,086,593 A 7/2000 Bonutti
6,086,614 A 7/2000 Mumme
6,102,948 A 8/2000 Brosnahan, III
6,102,954 A 8/2000 Albrektsson et al.
6,120,511 A 9/2000 Chan
6,120,542 A 9/2000 Camino et al.
6,132,433 A 10/2000 Whelan
6,139,508 A 10/2000 Simpson et al.
6,146,385 A 11/2000 Torrie et al.
6,149,654 A 11/2000 Johnson
6,152,960 A 11/2000 Pappas
6,159,216 A 12/2000 Burkinshaw et al.
6,165,223 A 12/2000 Metzger et al.
6,168,626 B1 1/2001 Hyon et al.
6,171,340 B1 1/2001 McDowell
6,193,724 B1 2/2001 Chan
6,206,885 B1 3/2001 Ghahremani et al.
6,206,926 B1 3/2001 Pappas
6,207,218 B1 3/2001 Layrolle et al.
6,217,549 B1 4/2001 Selmon et al.
6,217,619 B1 4/2001 Keller
6,228,119 B1 5/2001 Ondrla et al.
6,235,060 B1 5/2001 Kubein-Meesenburg et al.
6,245,074 B1 6/2001 Allard et al.
6,251,143 B1 6/2001 Schwartz et al.
6,254,605 B1 7/2001 Howell
6,270,347 B1 8/2001 Webster et al.
6,280,474 B1 8/2001 Cassidy et al.
6,299,645 B1 10/2001 Ogden
6,299,648 B1 10/2001 Doubler et al.
6,306,142 B1 10/2001 Johanson et al.
6,310,116 B1 10/2001 Yasuda et al.
6,315,798 B1 11/2001 Ashby et al.
6,322,500 B1 11/2001 Sikora et al.
6,328,752 B1 12/2001 Sjostrom et al.
6,342,075 B1 1/2002 MacArthur
6,358,251 B1 3/2002 Mirza
6,358,253 B1 3/2002 Torrie et al.
6,364,910 B1 * 4/2002 Shultz et al. .............. 623/19.13
6,375,658 B1 4/2002 Hangody et al.
6,383,188 B2 5/2002 Kuslich
6,402,785 B1 6/2002 Zdeblick et al.
6,415,516 B1 7/2002 Tirado et al.
6,416,518 B1 7/2002 DeMayo
6,443,954 B1 9/2002 Bramlet et al.
6,451,023 B1 9/2002 Salazar et al.
6,461,373 B2 10/2002 Wyman et al.
6,468,309 B1 10/2002 Lieberman
6,478,801 B1 11/2002 Ralph et al.
6,478,822 B1 11/2002 Leroux et al.
6,482,210 B1 11/2002 Skiba et al.
6,494,914 B2 12/2002 Brown
6,520,964 B2 2/2003 Tallarida et al.
6,527,754 B1 3/2003 Tallarida et al.
6,530,956 B1 3/2003 Mansmann
6,537,274 B1 3/2003 Katz
6,540,786 B2 4/2003 Chibrac et al.
6,547,823 B2 4/2003 Scarborough et al.
6,551,322 B1 4/2003 Lieberman
6,554,866 B1 4/2003 Aicher et al.
6,558,422 B1 5/2003 Baker et al.
6,575,980 B1 6/2003 Robie et al.
6,575,982 B1 6/2003 Bonutti
6,585,666 B2 7/2003 Suh et al.
6,589,281 B2 7/2003 Hyde, Jr.
6,591,581 B2 7/2003 Schmieding
6,599,321 B2 7/2003 Hyde et al.
6,602,258 B1 8/2003 Katz
6,607,561 B2 8/2003 Brannon
6,610,067 B2 8/2003 Tallarida
6,610,095 B1 8/2003 Pope et al.
6,623,474 B1 9/2003 Ponzi
6,626,950 B2 9/2003 Brown et al.
6,629,997 B2 10/2003 Mansmann
6,632,246 B1 10/2003 Simon et al.
6,679,917 B2 1/2004 Ek
6,720,469 B1 4/2004 Curtis et al.
6,746,451 B2 6/2004 Middleton et al.
6,755,837 B2 6/2004 Ebner
6,755,865 B2 6/2004 Tarabishy
6,770,078 B2 8/2004 Bonutti
6,783,550 B2 8/2004 MacArthur
6,783,551 B1 8/2004 Metzger
6,802,864 B2 10/2004 Tornier
6,814,735 B1 11/2004 Zimgibl
6,827,722 B1 12/2004 Schoenefeld
6,860,902 B2 3/2005 Reiley
6,881,228 B2 4/2005 Zdeblick et al.
6,884,246 B1 4/2005 Sonnabend et al.
6,884,621 B2 4/2005 Liao et al.
6,893,467 B1 5/2005 Bercovy
6,923,813 B2 8/2005 Phillips et al.
6,926,739 B1 8/2005 O'Connor
6,951,538 B2 10/2005 Ritland
6,953,478 B2 10/2005 Bouttens et al.
6,962,577 B2 11/2005 Tallarida et al.
6,969,393 B2 11/2005 Pinczewski et al.
6,984,248 B2 1/2006 Hyde, Jr.
6,989,016 B2 1/2006 Tallarida et al.
7,029,479 B2 4/2006 Tallarida
7,048,767 B2 5/2006 Namavar
7,063,717 B2 6/2006 St. Pierre et al.

(56) References Cited

U.S. PATENT DOCUMENTS 7,112,205 B2 9/2006 Carrison
7,115,131 B2 10/2006 Engh et al.
7,118,578 B2 10/2006 West, Jr. et al.
7,156,880 B2 1/2007 Evans et al.
7,160,305 B2 1/2007 Schmieding
7,163,541 B2 1/2007 Ek
7,166,133 B2 1/2007 Evans et al.
7,192,431 B2 3/2007 Hangody et al.
7,192,432 B2 3/2007 Wetzler et al.
7,204,839 B2 4/2007 Dreyfuss et al.
7,204,854 B2 4/2007 Guederian et al.
7,235,107 B2 6/2007 Evans et al.
7,238,189 B2 7/2007 Schmieding et al.
7,241,316 B2 7/2007 Evans et al.
7,264,634 B2 9/2007 Schmieding
7,290,347 B2 11/2007 Augustino et al.
7,303,577 B1 12/2007 Dean
7,311,702 B2 12/2007 Tallarida et al.
7,361,195 B2 4/2008 Schwartz et al.
7,368,065 B2 5/2008 Yang et al.
7,371,260 B2 5/2008 Malinin
7,462,199 B2 12/2008 Justin et al.
7,468,075 B2 12/2008 Lang et al.
7,476,250 B1 1/2009 Mansmann
7,491,235 B2 2/2009 Fell
7,501,073 B2 3/2009 Wen et al.
7,510,558 B2 3/2009 Tallarida
7,531,000 B2 5/2009 Hodorek
7,559,932 B2 7/2009 Truckai et al.
7,569,059 B2 8/2009 Cerundolo
7,572,291 B2 8/2009 Gil et al.
7,575,578 B2 8/2009 Wetzler et al.
7,578,824 B2 8/2009 Justin et al.
7,604,641 B2 10/2009 Tallarida et al.
7,611,653 B1 11/2009 Elsner et al.
7,618,451 B2 11/2009 Berez et al.
7,618,462 B2 11/2009 Ek
7,632,294 B2 12/2009 Milbodker et al.
7,641,658 B2 1/2010 Shaolian et al.
7,641,689 B2 1/2010 Fell et al.
7,670,381 B2 3/2010 Schwartz
7,678,151 B2 3/2010 Ek
7,682,540 B2 3/2010 Boyan et al.
7,687,462 B2 3/2010 Ting et al.
7,708,741 B1 5/2010 Bonutti
7,713,305 B2 5/2010 Ek
7,722,676 B2 5/2010 Hanson et al.
7,731,720 B2 6/2010 Sand et al.
7,731,738 B2 6/2010 Jackson et al.
7,738,187 B2 6/2010 Pazidis et al.
7,758,643 B2 7/2010 Stone et al.
7,806,872 B2 10/2010 Ponzi
7,815,645 B2 10/2010 Haines
7,828,853 B2 11/2010 Ek et al.
7,842,042 B2 11/2010 Reay-Young et al.
7,857,817 B2 12/2010 Tallarida et al.
7,896,883 B2 3/2011 Ek et al.
7,896,885 B2 3/2011 Miniaci et al.
7,901,408 B2 3/2011 Ek et al.
7,914,545 B2 3/2011 Ek
7,931,683 B2 4/2011 Weber et al.
7,951,163 B2 5/2011 Ek
7,955,382 B2 6/2011 Flanagan et al.
7,959,636 B2 6/2011 Schmieding
7,959,650 B2 6/2011 Kaiser et al.
7,959,681 B2 6/2011 Lavi
7,967,823 B2 6/2011 Ammann et al.
7,993,360 B2 8/2011 Hacker et al.
7,993,369 B2 8/2011 Dreyfuss
7,998,206 B2 8/2011 Shepard
8,012,206 B2 9/2011 Schmieding
8,021,367 B2 9/2011 Bourke et al.
8,038,652 B2 10/2011 Morrison et al.
8,038,678 B2 10/2011 Schmieding et al.
8,043,315 B2 10/2011 Shepard
8,043,319 B2 10/2011 Lyon et al.
8,048,079 B2 11/2011 Iannarone
8,048,157 B2 11/2011 Albertorio
8,057,478 B2 11/2011 Kuczynski et al.
8,062,301 B2 11/2011 Ammann et al.
8,062,319 B2 11/2011 O'Quinn et al.
8,083,746 B2 12/2011 Novak
8,083,749 B2 12/2011 Taber
8,083,803 B2 12/2011 Albertorio et al.
8,097,040 B2 1/2012 Russo et al.
8,137,406 B2 3/2012 Novak et al.
8,142,502 B2 3/2012 Stone et al.
8,147,559 B2 4/2012 Tallarida et al.
8,152,847 B2 4/2012 Strzepa et al.
8,157,867 B2 4/2012 Goble et al.
8,162,947 B2 4/2012 Dreyfuss
8,163,027 B2 4/2012 Rhodes et al.
8,167,951 B2 5/2012 Ammann et al.
8,177,738 B2 5/2012 Schmieding et al.
8,177,841 B2 5/2012 Ek
8,182,489 B2 5/2012 Horacek
8,202,282 B2 6/2012 Schmieding et al.
8,202,296 B2 6/2012 Burkhart
8,202,297 B2 6/2012 Burkhart
8,202,298 B2 6/2012 Cook et al.
8,202,306 B2 6/2012 Dreyfuss
8,202,318 B2 6/2012 Willobee
8,211,112 B2 7/2012 Novak et al.
8,221,455 B2 7/2012 Shurnas et al.
8,231,653 B2 7/2012 Dreyfuss
8,231,674 B2 7/2012 Albertorio et al.
8,236,000 B2 8/2012 Ammann et al.
8,267,977 B2 9/2012 Roth
8,298,247 B2 10/2012 Sterrett et al.
8,298,284 B2 10/2012 Cassani
8,303,830 B2 11/2012 Tong et al.
8,308,662 B2 11/2012 Lo
8,308,732 B2 11/2012 Millett et al.
8,323,347 B2 12/2012 Guederian et al.
8,328,716 B2 12/2012 Schmieding et al.
8,333,774 B2 12/2012 Morrison
8,343,186 B2 1/2013 Dreyfuss et al.
8,348,960 B2 1/2013 Michel et al.
8,348,975 B2 1/2013 Dreyfuss
8,353,915 B2 1/2013 Helenbolt et al.
8,361,159 B2 1/2013 Ek
8,377,068 B2 2/2013 Aker et al.
8,382,789 B2 2/2013 Weber et al.
8,382,810 B2 2/2013 Peterson et al.
8,388,624 B2 3/2013 Ek et al.
8,398,678 B2 3/2013 Baker et al.
8,409,209 B2 4/2013 Ammann et al.
8,409,250 B2 4/2013 Schmieding et al.
8,414,908 B2 4/2013 Jin et al.
8,419,794 B2 4/2013 ElAttrache et al.
8,425,554 B2 4/2013 Denove et al.
8,430,909 B2 4/2013 Dreyfuss
8,435,272 B2 5/2013 Dougherty et al.
8,439,976 B2 5/2013 Albertorio et al.
8,444,680 B2 5/2013 Dooney, Jr. et al.
8,460,317 B2 6/2013 Merves
8,460,318 B2 6/2013 Murray et al.
8,460,350 B2 6/2013 Albertorio et al.
8,460,379 B2 6/2013 Albertorio et al.
8,475,536 B2 7/2013 Tong et al.
8,486,072 B2 7/2013 Haininger
8,496,662 B2 7/2013 Novak et al.
8,506,573 B2 8/2013 Dreyfuss et al.
8,512,376 B2 8/2013 Thornes
8,512,411 B2 8/2013 Sluss et al.
8,523,872 B2 9/2013 Ek
8,535,330 B2 9/2013 Sherman et al.
8,535,703 B2 9/2013 Schmieding et al.
8,540,717 B2 9/2013 Tallarida et al.
8,540,777 B2 9/2013 Ammann et al.
8,540,778 B2 9/2013 Rhodes et al.
8,551,101 B2 10/2013 Kuczynski
8,579,940 B2 11/2013 Dreyfuss et al.
8,579,944 B2 11/2013 Holloway et al.

(56) References Cited

U.S. PATENT DOCUMENTS 8,591,514 B2 11/2013 Sherman
8,591,523 B2 11/2013 Weber
8,591,544 B2 11/2013 Jolly et al.
8,591,578 B2 11/2013 Albertorio et al.
8,591,592 B2 11/2013 Dreyfuss
8,597,361 B2 12/2013 Sidebotham et al.
8,623,052 B2 1/2014 Dreyfuss et al.
8,628,573 B2 1/2014 Roller et al.
8,652,139 B2 2/2014 Sterrett et al.
8,663,230 B2 3/2014 Miniaci et al.
8,663,250 B2 3/2014 Weber
8,663,251 B2 3/2014 Burkhart et al.
8,663,279 B2 3/2014 Burkhart et al.
8,663,324 B2 3/2014 Schmieding et al.
8,663,333 B2 3/2014 Metcalfe et al.
8,668,738 B2 3/2014 Schmieding et al.
8,702,715 B2 4/2014 Ammann et al.
8,702,752 B2 4/2014 Schmieding et al.
8,709,052 B2 4/2014 Ammann et al.
8,709,091 B2 4/2014 Rhodes et al.
8,721,722 B2 5/2014 Shah et al.
8,728,131 B2 5/2014 Di Giacomo et al.
8,734,449 B2 5/2014 Schmied et al.
8,753,375 B2 6/2014 Albertorio
8,758,356 B2 6/2014 Fearon et al.
8,764,797 B2 7/2014 Dreyfuss et al.
8,764,807 B2 7/2014 Michel et al.
8,764,839 B2 7/2014 Rhodes et al.
8,771,279 B2 7/2014 Philippon et al.
8,771,351 B2 7/2014 ElAttrache et al.
8,784,423 B2 7/2014 Kowarsch et al.
8,790,401 B2 7/2014 Schmieding et al.
8,801,755 B2 8/2014 Dreyfuss et al.
8,821,541 B2 9/2014 Dreyfuss et al.
8,834,475 B2 9/2014 Ammann et al.
8,834,521 B2 9/2014 Pinto et al.
8,840,619 B2 9/2014 Zajac et al.
8,840,643 B2 9/2014 Dreyfuss
8,852,190 B2 10/2014 Sherman
8,852,201 B2 10/2014 Schmieding et al.
8,858,560 B2 10/2014 Bradley et al.
8,864,827 B2 10/2014 Ek
8,870,877 B2 10/2014 Koogle, Jr.
8,876,900 B2 11/2014 Guederian et al.
8,882,833 B2 11/2014 Saylor et al.
8,882,847 B2 11/2014 Burdulis, Jr. et al.
8,888,781 B2 11/2014 Sterrett
8,888,785 B2 11/2014 Ammann et al.
8,888,815 B2 11/2014 Holmes, Jr.
8,906,026 B2 12/2014 Ammann et al.
8,911,457 B2 12/2014 Koogle, Jr. et al.
8,920,497 B2 12/2014 Albertorio et al.
8,926,615 B2 1/2015 Ek
8,927,283 B2 1/2015 Komvopoulos et al.
8,939,980 B2 1/2015 Schmieding et al.
8,939,999 B2 1/2015 Sterrett et al.
8,956,369 B2 2/2015 Millett et al.
8,961,538 B2 2/2015 Koogle, Jr. et al.
8,961,575 B2 2/2015 Choinski
8,961,614 B2 2/2015 Ek et al.
8,974,537 B2 3/2015 Dreyfuss
8,986,346 B2 3/2015 Dreyfuss
9,005,245 B2 4/2015 Thornes et al.
9,005,246 B2 4/2015 Burkhart et al.
9,044,343 B2 6/2015 Ek
9,055,955 B2 6/2015 Ek et al.
9,066,716 B2 6/2015 Sikora et al.
9,072,510 B2 7/2015 Thornes et al.
9,072,555 B2 7/2015 Michel
9,078,650 B2 7/2015 Weber
9,078,661 B2 7/2015 Gallo
9,089,363 B2 7/2015 Dooney, Jr. et al.
9,089,433 B2 7/2015 Karnes et al.
9,095,641 B2 8/2015 Albertorio
9,101,366 B2 8/2015 Sterrett et al.
9,101,461 B2 8/2015 Albertorio et al.
9,107,653 B2 8/2015 Sullivan
9,107,676 B2 8/2015 Burkhart et al.
9,113,859 B2 8/2015 Dooney, Jr. et al.
9,113,920 B2 8/2015 Ammann et al.
9,138,223 B2 9/2015 Jolly et al.
9,138,237 B2 9/2015 Meade et al.
9,138,241 B2 9/2015 Kuczynski
9,138,246 B2 9/2015 Anderson et al.
9,146,576 B2 9/2015 Schmieding et al.
9,168,124 B2 10/2015 Guerra et al.
9,179,907 B2 11/2015 ElAttrache et al.
9,179,950 B2 11/2015 Zajac et al.
9,186,432 B2 11/2015 Mazzocca et al.
9,204,873 B2 12/2015 Tallarida et al.
9,204,874 B2 12/2015 Denove et al.
9,204,960 B2 12/2015 Albertorio et al.
9,216,017 B2 12/2015 Burkhart
9,216,022 B2 12/2015 Karnes et al.
9,216,090 B2 12/2015 Metcalfe
9,216,091 B2 12/2015 Hardy et al.
9,226,743 B2 1/2016 Dreyfuss et al.
9,226,815 B2 1/2016 Schmieding et al.
2001/0010023 A1 7/2001 Schwartz et al.
2001/0012967 A1 8/2001 Mosseri
2001/0016775 A1 8/2001 Scarborough et al.
2001/0034526 A1 10/2001 Kuslich et al.
2001/0039455 A1 11/2001 Simon et al.
2001/0053914 A1 12/2001 Landry et al.
2001/0056266 A1 12/2001 Tallarida et al.
2002/0022847 A1 2/2002 Ray, III et al.
2002/0022889 A1 2/2002 Chibrac et al.
2002/0022890 A1 2/2002 Jacobsson et al.
2002/0049444 A1 4/2002 Knox
2002/0055783 A1 5/2002 Tallarida et al.
2002/0082701 A1 6/2002 Zdeblick et al.
2002/0106393 A1 8/2002 Bianchi et al.
2002/0138150 A1 9/2002 Leclercq
2002/0143342 A1 10/2002 Hangody et al.
2002/0147498 A1 10/2002 Tallarida et al.
2002/0155144 A1 10/2002 Troczynski et al.
2002/0156480 A1 10/2002 Overes et al.
2002/0173797 A1 11/2002 Van Zile et al.
2002/0183760 A1 12/2002 McGovern et al.
2003/0028196 A1 2/2003 Bonutti
2003/0060887 A1 3/2003 Ek
2003/0065391 A1 4/2003 Re et al.
2003/0100953 A1 5/2003 Rosa et al.
2003/0105465 A1 6/2003 Schmieding et al.
2003/0120276 A1 6/2003 Tallarida et al.
2003/0120278 A1 6/2003 Morgan et al.
2003/0130741 A1 7/2003 McMinn
2003/0144736 A1 7/2003 Sennett
2003/0171756 A1 9/2003 Fallin et al.
2003/0171820 A1 9/2003 Wilshaw et al.
2003/0181878 A1 9/2003 Tallarida et al.
2003/0195470 A1 10/2003 Ponzi
2003/0204195 A1 10/2003 Keane et al.
2003/0204267 A1 10/2003 Hazebrouck et al.
2003/0216669 A1 11/2003 Lang et al.
2003/0216742 A1 11/2003 Wetzler et al.
2003/0225456 A1 12/2003 Ek
2003/0225457 A1 12/2003 Justin et al.
2003/0229352 A1 12/2003 Penenberg
2004/0015170 A1 1/2004 Tallarida et al.
2004/0033212 A1 2/2004 Thomson et al.
2004/0034359 A1 2/2004 Schmieding et al.
2004/0034437 A1 2/2004 Schmieding
2004/0039389 A1 2/2004 West, Jr. et al.
2004/0082906 A1 4/2004 Tallarida et al.
2004/0083005 A1 4/2004 Jacobsson et al.
2004/0092946 A1 5/2004 Bagga et al.
2004/0106928 A1 6/2004 Ek
2004/0133276 A1 7/2004 Lang et al.
2004/0138754 A1 7/2004 Lang et al.
2004/0138758 A1 7/2004 Evans et al.
2004/0148030 A1 7/2004 Ek
2004/0153086 A1 8/2004 Sanford
2004/0153087 A1 8/2004 Sanford et al.

(56) References Cited

U.S. PATENT DOCUMENTS

2004/0167632 A1 8/2004 Wen et al.
2004/0167633 A1 8/2004 Wen et al.
2004/0176775 A1 9/2004 Burkus et al.
2004/0186582 A1 9/2004 Yasuda et al.
2004/0193172 A1 9/2004 Ross et al.
2004/0193175 A1 9/2004 Maroney et al.
2004/0193267 A1 9/2004 Jones et al.
2004/0193268 A1 9/2004 Hazebrouck
2004/0193281 A1 9/2004 Grimes
2004/0199166 A1 10/2004 Schmieding et al.
2004/0204760 A1 10/2004 Fitz et al.
2004/0210309 A1 10/2004 Denzer et al.
2004/0220574 A1 11/2004 Pelo et al.
2004/0230315 A1 11/2004 Ek
2004/0260303 A1 12/2004 Carrison
2005/0015153 A1 1/2005 Gobel et al.
2005/0038520 A1 2/2005 Binette et al.
2005/0043805 A1 2/2005 Chudik
2005/0043808 A1 2/2005 Felt et al.
2005/0049716 A1 3/2005 Wagener et al.
2005/0065612 A1 3/2005 Winslow
2005/0075642 A1 4/2005 Felt
2005/0085909 A1 4/2005 Eisermann
2005/0090905 A1 4/2005 Hawkins et al.
2005/0119758 A1 6/2005 Alexander et al.
2005/0143731 A1 6/2005 Justin et al.
2005/0143745 A1 6/2005 Hodorek et al.
2005/0143821 A1 6/2005 Zdeblick et al.
2005/0143831 A1 6/2005 Justin et al.
2005/0149044 A1 7/2005 Justin et al.
2005/0154398 A1 7/2005 Miniaci et al.
2005/0165487 A1 7/2005 Muhanna et al.
2005/0177171 A1 8/2005 Wetzler et al.
2005/0209705 A1 9/2005 Niederauer et al.
2005/0222687 A1 10/2005 Vunjak-Novakovic et al.
2005/0229323 A1 10/2005 Mills et al.
2005/0234461 A1 10/2005 Burdulis, Jr. et al.
2005/0251268 A1 11/2005 Truncale
2005/0287187 A1 12/2005 Mansmann
2006/0004461 A1 1/2006 Justin et al.
2006/0009774 A1 1/2006 Goble et al.
2006/0020343 A1 1/2006 Ek
2006/0052878 A1 3/2006 Schmieding
2006/0058744 A1 3/2006 Tallarida et al.
2006/0058809 A1* 3/2006 Zink et al. .................... 606/102
2006/0058883 A1 3/2006 Aram et al.
2006/0069394 A1 3/2006 Weiler et al.
2006/0074430 A1 4/2006 Deffenbaugh et al.
2006/0085006 A1 4/2006 Ek
2006/0085077 A1 4/2006 Cook et al.
2006/0105015 A1 5/2006 Perla et al.
2006/0111787 A1 5/2006 Bailie et al.
2006/0121080 A1 6/2006 Lye et al.
2006/0142772 A1 6/2006 Ralph et al.
2006/0149370 A1 7/2006 Schmieding et al.
2006/0154206 A1 7/2006 Petersson et al.
2006/0167560 A1 7/2006 Heck et al.
2006/0184187 A1 8/2006 Surti
2006/0190002 A1 8/2006 Tallarida
2006/0195112 A1 8/2006 Ek
2006/0217728 A1 9/2006 Chervitz et al.
2006/0229726 A1 10/2006 Ek
2006/0271059 A1 11/2006 Reay-Young et al.
2007/0005143 A1 1/2007 Ek
2007/0029951 A1 2/2007 Schmieding
2007/0038302 A1 2/2007 Shultz et al.
2007/0038307 A1 2/2007 Webster et al.
2007/0073394 A1 3/2007 Seedhom et al.
2007/0093842 A1 4/2007 Schmieding
2007/0093848 A1 4/2007 Harris et al.
2007/0093890 A1 4/2007 Eliasen et al.
2007/0093896 A1 4/2007 Malinin
2007/0118136 A1 5/2007 Ek
2007/0118224 A1 5/2007 Shah et al.
2007/0123921 A1 5/2007 Ek
2007/0134291 A1 6/2007 Ting et al.
2007/0173850 A1 7/2007 Rangaiah et al.
2007/0179608 A1 8/2007 Ek
2007/0233128 A1 10/2007 Schmieding et al.
2007/0244484 A1 10/2007 Luginbuehl
2007/0250067 A1 10/2007 Schmieding et al.
2007/0255399 A1 11/2007 Eliasen et al.
2007/0255412 A1 11/2007 Hajaj et al.
2007/0265700 A1 11/2007 Eliasen et al.
2007/0270711 A1 11/2007 Gil et al.
2007/0270873 A1 11/2007 Flickinger et al.
2007/0282455 A1 12/2007 Luginbuehl et al.
2007/0288031 A1 12/2007 Dreyfuss et al.
2007/0299519 A1 12/2007 Schmieding
2007/0299529 A1 12/2007 Rhodes et al.
2008/0004659 A1 1/2008 Burkhart et al.
2008/0015607 A1 1/2008 D'Alessio et al.
2008/0015709 A1 1/2008 Evans et al.
2008/0027430 A1 1/2008 Montgomery et al.
2008/0033443 A1 2/2008 Sikora et al.
2008/0033447 A1 2/2008 Sand
2008/0046084 A1 2/2008 Sledge
2008/0071381 A1 3/2008 Buscher et al.
2008/0086139 A1 4/2008 Bourke et al.
2008/0086152 A1 4/2008 McKay et al.
2008/0097618 A1 4/2008 Baker et al.
2008/0103506 A1 5/2008 Volpi et al.
2008/0138611 A1 6/2008 Yasuzawa et al.
2008/0154271 A1 6/2008 Berberich et al.
2008/0172125 A1 7/2008 Ek
2008/0183290 A1 7/2008 Baird et al.
2008/0188935 A1 8/2008 Saylor et al.
2008/0195113 A1 8/2008 Sikora
2008/0208201 A1 8/2008 Moindreau et al.
2008/0243262 A1 10/2008 Lee
2008/0243263 A1 10/2008 Lee et al.
2008/0262500 A1 10/2008 Collazo
2008/0262625 A1 10/2008 Spriano et al.
2008/0275451 A1 11/2008 McAllister et al.
2008/0275512 A1 11/2008 Albertirio et al.
2008/0294168 A1 11/2008 Wieland
2008/0306483 A1 12/2008 Iannarone
2008/0317807 A1 12/2008 Lu et al.
2009/0018543 A1 1/2009 Ammann et al.
2009/0035722 A1 2/2009 Balasundaram et al.
2009/0054899 A1 2/2009 Ammann et al.
2009/0069816 A1 3/2009 Sasing et al.
2009/0076512 A1 3/2009 Ammann et al.
2009/0088753 A1 4/2009 Aram et al.
2009/0088858 A1 4/2009 Zinger et al.
2009/0105772 A1 4/2009 Seebeck et al.
2009/0112211 A1 4/2009 Johnstone
2009/0138077 A1 5/2009 Weber et al.
2009/0143783 A1 6/2009 Dower
2009/0143784 A1 6/2009 Petersen et al.
2009/0149860 A1 6/2009 Scribner et al.
2009/0198288 A1 8/2009 Hoof et al.
2009/0210057 A1 8/2009 Liao et al.
2009/0216268 A1 8/2009 Panter
2009/0216285 A1 8/2009 Ek et al.
2009/0220561 A1 9/2009 Jin et al.
2009/0222012 A1 9/2009 Karnes et al.
2009/0228105 A1 9/2009 Son et al.
2009/0234452 A1 9/2009 Steiner et al.
2009/0264889 A1 10/2009 Long et al.
2009/0264928 A1 10/2009 Blain
2009/0276052 A1 11/2009 Regala et al.
2009/0283701 A1 11/2009 Ogawa
2010/0003638 A1 1/2010 Collins et al.
2010/0015244 A1 1/2010 Jain et al.
2010/0028387 A1 2/2010 Balasundaram et al.
2010/0028999 A1 2/2010 Nain
2010/0036381 A1 2/2010 Vanleeuwen et al.
2010/0057197 A1 3/2010 Weber et al.
2010/0087829 A1 4/2010 Metzger et al.
2010/0092535 A1 4/2010 Cook et al.
2010/0112519 A1 5/2010 Hall et al.
2010/0136289 A1 6/2010 Extrand et al.
2010/0168854 A1 7/2010 Luers et al.

(56) References Cited

U.S. PATENT DOCUMENTS

| | | | |
|---|---|---|---|
| 2010/0185294 | A1 | 7/2010 | Ek |
| 2010/0217315 | A1 | 8/2010 | Jolly et al. |
| 2010/0227372 | A1 | 9/2010 | Bilek et al. |
| 2010/0249930 | A1 | 9/2010 | Myers |
| 2010/0256645 | A1 | 10/2010 | Zajac et al. |
| 2010/0256758 | A1 | 10/2010 | Gordon et al. |
| 2010/0268227 | A1 | 10/2010 | Tong et al. |
| 2010/0268330 | A1 | 10/2010 | Tong et al. |
| 2010/0268346 | A1 | 10/2010 | Tong et al. |
| 2010/0268347 | A1 | 10/2010 | Tong et al. |
| 2011/0009964 | A1 | 1/2011 | Schwartz et al. |
| 2011/0035012 | A1 | 2/2011 | Linares |
| 2011/0059312 | A1 | 3/2011 | Howling et al. |
| 2011/0066242 | A1 | 3/2011 | Lu et al. |
| 2011/0085968 | A1 | 4/2011 | Jin et al. |
| 2011/0087280 | A1 | 4/2011 | Albertorio |
| 2011/0106271 | A1 | 5/2011 | Regala et al. |
| 2011/0125263 | A1 | 5/2011 | Webster et al. |
| 2011/0125277 | A1 | 5/2011 | Nygren et al. |
| 2011/0152869 | A1 | 6/2011 | Ek et al. |
| 2011/0159070 | A1 | 6/2011 | Jin et al. |
| 2011/0190902 | A1 | 8/2011 | Tong et al. |
| 2011/0196367 | A1 | 8/2011 | Gallo |
| 2011/0213375 | A1 | 9/2011 | Sikora et al. |
| 2011/0236435 | A1 | 9/2011 | Biris |
| 2011/0238069 | A1 | 9/2011 | Zajac et al. |
| 2011/0251621 | A1 | 10/2011 | Sluss et al. |
| 2011/0257753 | A1 | 10/2011 | Gordon et al. |
| 2011/0300186 | A1 | 12/2011 | Hellstrom et al. |
| 2011/0301716 | A1 | 12/2011 | Sirivisoot et al. |
| 2012/0022656 | A1 | 1/2012 | Lavi |
| 2012/0027837 | A1 | 2/2012 | DeMuth et al. |
| 2012/0051489 | A1 | 3/2012 | Varanasi et al. |
| 2012/0058328 | A1 | 3/2012 | Tourvieille et al. |
| 2012/0065732 | A1 | 3/2012 | Roller et al. |
| 2012/0109136 | A1 | 5/2012 | Bourque et al. |
| 2012/0116502 | A1 | 5/2012 | Su et al. |
| 2012/0123474 | A1 | 5/2012 | Zajac et al. |
| 2012/0123541 | A1 | 5/2012 | Albertorio et al. |
| 2012/0128666 | A1 | 5/2012 | Pébay et al. |
| 2012/0150225 | A1 | 6/2012 | Burkhart et al. |
| 2012/0150286 | A1 | 6/2012 | Weber et al. |
| 2012/0165868 | A1 | 6/2012 | Burkhart et al. |
| 2012/0183799 | A1 | 7/2012 | Steele et al. |
| 2012/0185058 | A1 | 7/2012 | Albertorio et al. |
| 2012/0189833 | A1 | 7/2012 | Suchanek et al. |
| 2012/0189844 | A1 | 7/2012 | Jain et al. |
| 2012/0209278 | A1 | 8/2012 | Ries et al. |
| 2012/0265298 | A1 | 10/2012 | Schmieding et al. |
| 2012/0330357 | A1 | 12/2012 | Thal |
| 2013/0023907 | A1 | 1/2013 | Sterrett et al. |
| 2013/0023927 | A1 | 1/2013 | Cassani |
| 2013/0046312 | A1 | 2/2013 | Millett et al. |
| 2013/0096563 | A1 | 4/2013 | Meade et al. |
| 2013/0096612 | A1 | 4/2013 | Zajac et al. |
| 2013/0103104 | A1 | 4/2013 | Krupp et al. |
| 2013/0110165 | A1 | 5/2013 | Burkhart et al. |
| 2013/0138108 | A1 | 5/2013 | Dryfuss et al. |
| 2013/0138150 | A1 | 5/2013 | Baker et al. |
| 2013/0150885 | A1 | 6/2013 | Dreyfuss |
| 2013/0165954 | A1 | 6/2013 | Dreyfuss et al. |
| 2013/0165972 | A1 | 6/2013 | Sullivan |
| 2013/0178871 | A1 | 7/2013 | Koogle, Jr. et al. |
| 2013/0184818 | A1 | 7/2013 | Coughlin et al. |
| 2013/0190819 | A1 | 7/2013 | Norton |
| 2013/0190885 | A1 | 7/2013 | Ammann et al. |
| 2013/0204257 | A1 | 8/2013 | Zajac |
| 2013/0204259 | A1 | 8/2013 | Zajac |
| 2013/0205936 | A1 | 8/2013 | Schmieding et al. |
| 2013/0218176 | A1 | 8/2013 | Denove et al. |
| 2013/0238099 | A1 | 9/2013 | Hardy et al. |
| 2013/0245775 | A1 | 9/2013 | Metcalfe |
| 2013/0268073 | A1 | 10/2013 | Albertorio et al. |
| 2013/0289570 | A1 | 10/2013 | Chao |
| 2013/0304209 | A1 | 11/2013 | Schmieding et al. |
| 2013/0331886 | A1 | 12/2013 | Thornes |
| 2013/0338722 | A1 | 12/2013 | Yalizis |
| 2013/0338792 | A1 | 12/2013 | Schmieding et al. |
| 2013/0344600 | A1 | 12/2013 | Jin et al. |
| 2013/0345747 | A1 | 12/2013 | Dreyfuss |
| 2013/0345748 | A1 | 12/2013 | Dreyfuss |
| 2014/0012267 | A1 | 1/2014 | Skiora et al. |
| 2014/0012389 | A1 | 1/2014 | Ek |
| 2014/0052178 | A1 | 2/2014 | Dooney, Jr. |
| 2014/0052179 | A1 | 2/2014 | Dreyfuss et al. |
| 2014/0074164 | A1 | 3/2014 | Dreyfuss et al. |
| 2014/0074239 | A1 | 3/2014 | Albertorio et al. |
| 2014/0079921 | A1 | 3/2014 | De Volder |
| 2014/0081273 | A1 | 3/2014 | Sherman |
| 2014/0081399 | A1 | 3/2014 | Roller et al. |
| 2014/0088601 | A1 | 3/2014 | Kuczynski |
| 2014/0088602 | A1 | 3/2014 | Ammann et al. |
| 2014/0114322 | A1 | 4/2014 | Perez, III |
| 2014/0114367 | A1 | 4/2014 | Jolly et al. |
| 2014/0121700 | A1 | 5/2014 | Dreyfuss et al. |
| 2014/0121701 | A1 | 5/2014 | Dreyfuss et al. |
| 2014/0128889 | A1 | 5/2014 | Sullivan et al. |
| 2014/0128915 | A1 | 5/2014 | Dreyfuss et al. |
| 2014/0128921 | A1 | 5/2014 | Parsons et al. |
| 2014/0155902 | A1 | 6/2014 | Sikora et al. |
| 2014/0188232 | A1 | 7/2014 | Metcalfe et al. |
| 2014/0194880 | A1 | 7/2014 | Schmieding et al. |
| 2014/0228849 | A1 | 8/2014 | Sterrett et al. |
| 2014/0236306 | A1 | 8/2014 | Karnes et al. |
| 2014/0243439 | A1 | 8/2014 | Papangelou et al. |
| 2014/0243891 | A1 | 8/2014 | Schmieding et al. |
| 2014/0243892 | A1 | 8/2014 | Choinski |
| 2014/0243976 | A1 | 8/2014 | Schmieding et al. |
| 2014/0257297 | A1 | 9/2014 | Koogle, Jr. et al. |
| 2014/0257299 | A1 | 9/2014 | Berelsman et al. |
| 2014/0257384 | A1 | 9/2014 | Dreyfuss et al. |
| 2014/0276841 | A1 | 9/2014 | Albertorio et al. |
| 2014/0276990 | A1 | 9/2014 | Perez, III |
| 2014/0277020 | A1 | 9/2014 | Koogle et al. |
| 2014/0277121 | A1 | 9/2014 | Pilgeram et al. |
| 2014/0277134 | A1 | 9/2014 | ElAttrache et al. |
| 2014/0277181 | A1 | 9/2014 | Garlock |
| 2014/0277186 | A1 | 9/2014 | Granberry et al. |
| 2014/0277214 | A1 | 9/2014 | Helenbolt et al. |
| 2014/0277448 | A1 | 9/2014 | Guerra et al. |
| 2014/0288657 | A1 | 9/2014 | Lederman et al. |
| 2014/0309689 | A1 | 10/2014 | Sikora et al. |
| 2014/0324167 | A1 | 10/2014 | Schmieding et al. |
| 2014/0335145 | A1 | 11/2014 | Jin et al. |
| 2014/0350688 | A1 | 11/2014 | Michel et al. |
| 2015/0134066 | A1 | 5/2015 | Bachmaier |
| 2015/0142052 | A1 | 5/2015 | Koogle, Jr. et al. |
| 2015/0201951 | A1 | 7/2015 | Bradley et al. |
| 2015/0216541 | A1 | 8/2015 | Schmieding et al. |
| 2015/0245831 | A1 | 9/2015 | Sullivan |
| 2015/0250472 | A1 | 9/2015 | Ek et al. |
| 2015/0250475 | A1 | 9/2015 | Ek |
| 2015/0250594 | A1 | 9/2015 | Ek |
| 2015/0250602 | A1 | 9/2015 | Sikora et al. |
| 2015/0313586 | A1 | 11/2015 | Burkhart et al. |

FOREIGN PATENT DOCUMENTS

| | | | |
|---|---|---|---|
| AU | 2002248198 | B2 | 5/2007 |
| AU | 2005202099 | B2 | 6/2007 |
| AU | 2002357284 | B2 | 8/2007 |
| AU | 2006202337 | B2 | 5/2008 |
| AU | 2003262428 | | 8/2009 |
| AU | 2007216648 | B2 | 11/2009 |
| AU | 2004216106 | B2 | 6/2010 |
| AU | 2008207536 | B2 | 3/2011 |
| CA | 2470194 | C | 2/2011 |
| DE | 2933174 | | 4/1980 |
| DE | 3516743 | | 11/1986 |
| DE | 3840466 | | 6/1990 |
| DE | 19505083 | | 11/1995 |
| DE | 102004053606 | | 5/2006 |
| DE | 112013003358 | | 3/2015 |
| EP | 0240004 | | 10/1987 |

(56) References Cited

FOREIGN PATENT DOCUMENTS

| | | |
|---|---|---|
| EP | 0241240 | 10/1987 |
| EP | 0290736 | 11/1988 |
| EP | 0350780 | 7/1989 |
| EP | 0350780 | 1/1990 |
| EP | 0485678 | 5/1992 |
| EP | 0327387 | 9/1992 |
| EP | 0505634 | 9/1992 |
| EP | 0736292 | 10/1996 |
| EP | 0903125 | 3/1999 |
| EP | 0903127 | 3/1999 |
| EP | 0993812 | 4/2000 |
| EP | 0661023 | 8/2001 |
| EP | 1374782 | 1/2004 |
| EP | 1426013 | 9/2004 |
| EP | 1870060 | 12/2007 |
| EP | 1927328 | 6/2008 |
| EP | 1278460 | 4/2009 |
| EP | 2062541 | 5/2009 |
| EP | 2314257 | 2/2013 |
| EP | 2804565 | 10/2014 |
| EP | 2481368 | 12/2014 |
| FR | 2242068 | 3/1975 |
| FR | 2642301 | 3/1990 |
| FR | 2676917 | 12/1992 |
| FR | 2693650 | 1/1994 |
| FR | 2718014 | 10/1995 |
| FR | 2733904 | 11/1996 |
| FR | 2739151 | 3/1997 |
| GB | 2281577 | 3/1995 |
| GB | 2372707 | 9/2002 |
| JP | 61502029 | 9/1986 |
| JP | 63300758 | 12/1988 |
| JP | 3504932 | 10/1991 |
| JP | H03-092328 | 11/1992 |
| JP | 518511 | 3/1993 |
| JP | 06339490 | 12/1994 |
| JP | 11244315 | 9/1999 |
| JP | 2964035 | 10/1999 |
| JP | 2001525210 | 12/2001 |
| JP | 2002291779 | 10/2002 |
| JP | 2003534096 | 11/2003 |
| WO | 88/03781 | 6/1988 |
| WO | 8803781 | 6/1988 |
| WO | 8909578 | 10/1989 |
| WO | 9409730 | 5/1994 |
| WO | 9427507 | 12/1994 |
| WO | 9624304 | 8/1996 |
| WO | 9722306 | 6/1997 |
| WO | 9920192 | 4/1999 |
| WO | 0013597 | 3/2000 |
| WO | 0105336 | 1/2001 |
| WO | 0166021 | 9/2001 |
| WO | 0166022 | 9/2001 |
| WO | 0182677 | 11/2001 |
| WO | 0191648 | 12/2001 |
| WO | 0191672 | 12/2001 |
| WO | 0217821 | 3/2002 |
| WO | 02086180 | 10/2002 |
| WO | 03047470 | 6/2003 |
| WO | 03051210 | 6/2003 |
| WO | 03051211 | 6/2003 |
| WO | 03061516 | 7/2003 |
| WO | 03065909 | 8/2003 |
| WO | 2004014261 | 2/2004 |
| WO | 2004026170 | 4/2004 |
| WO | 2004052216 | 6/2004 |
| WO | 2004075777 | 9/2004 |
| WO | 2004100839 | 11/2004 |
| WO | 2005051231 | 6/2005 |
| WO | 2005512331 | 6/2005 |
| WO | 2006004885 | 1/2006 |
| WO | 2006074321 | 7/2006 |
| WO | 2006091686 | 8/2006 |
| WO | 2014008126 | 1/2014 |
| WO | 2014172347 | 10/2014 |

OTHER PUBLICATIONS

Australian Office Action issued in related Australian Patent Application No. 2003262428 dated Mar. 20, 2008.

Australian Office Action issued in related Australian Patent Application No. 2004293042 dated Feb. 20, 2008.

U.S. Office Action issued in related U.S. Appl. No. 11/326,133 dated Jun. 12, 2008.

International Search Report and Written Opinion dated Jun. 24, 2008 issued in related International Patent Application No. PCT/US07/73685.

International Search Report and Written Opinion dated Jun. 11, 2008 issued in related International Patent Application No. PCT/US07/25284.

International Search Report and Written Opinion dated Aug. 8, 2008 issued in related International Patent Application No. PCT/US08/53988.

U.S. Office Action issued in related U.S. Appl. No. 10/994,453 dated Jun. 5, 2007.

Japanese Office Action dated Jul. 22, 2008 issued in related Japanese Patent Application No. 2006-501193.

U.S. Office Action issued in related U.S. Appl. No. 10/373,463 dated Apr. 21, 2008.

Notice of Allowance received in U.S. Appl. No. 10/618,887 dated Aug. 15, 2008.

Australia Office Action issued in related Australian Patent Application No. 2007216648 dated May 30, 2008.

European Office Action issued in related European Patent Application No. 01932833.5-2310 dated Apr. 25, 2008.

U.S. Office Action received in related U.S. Appl. No. 11/169,326 dated Jun. 30, 2008.

U.S. Office Action received in related U.S. Appl. No. 11/169,326 dated Jul. 27, 2007.

U.S. Office Action received in related U.S. Appl. No. 11/169,326 dated Apr. 17, 2007.

U.S. Office Action received in related U.S. Appl. No. 11/169,326 dated Mar. 9, 2007.

Canadian Office Action issued in related Canadian Patent Application No. 2546582 dated Aug. 21, 2008.

U.S. Office Action issued in related U.S. Appl. No. 10/994,453 dated Sep. 3, 2008.

USPTO Office Action dated Dec. 21, 2007 issued in corresponding U.S. Appl. No. 11/169,326.

USPTO Office Action dated Dec. 26, 2007 issued in U.S. Appl. No. 11/379,151.

USPTO Office Action dated Oct. 9, 2007 issued in U.S. Appl. No. 10/373,463.

USPTO Office Action dated Aug. 29, 2007 issued in U.S. Appl. No. 10/760,965.

USPTO Office Action dated May 31, 2007 issued in corresponding U.S. Appl. No. 11/326,133.

USPTO Office Action dated Apr. 26, 2007 issued in U.S. Appl. No. 10/373,463.

USPTO Office Action dated Apr. 4, 2007 issued in corresponding U.S. Appl. No. 10/789,545.

USPTO Office Action dated Mar. 15, 2007 issued in U.S. Appl. No. 10/760,965.

USPTO Office Action dated Feb. 20, 2007 issued in corresponding U.S. Appl. No. 11/326,133.

USPTO Office Action dated Nov. 6, 2006 issued in U.S. Appl. No. 10/760,965.

USPTO Office Action dated Oct. 17, 2006 issued in U.S. Appl. No. 10/373,463.

USPTO Office Action dated Oct. 31, 2006 issued in U.S. Appl. No. 10/760,965.

USPTO Office Action dated Jul. 25, 2006 issued in U.S. Appl. No. 10/760,965.

USPTO Office action dated May 10, 2006 issued in corresponding U.S. Appl. No. 10/373,463.

USPTO Office Action dated Apr. 21, 2006 issued in corresponding U.S. Appl. No. 10/308,718.

USPTO Office Action dated Nov. 9, 2005 issued in corresponding U.S. Appl. No. 10/308,718.

(56) References Cited

OTHER PUBLICATIONS

USPTO Office action dated Dec. 8, 2005 issued in corresponding U.S. Appl. No. 10/373,463.
USPTO Office Action dated Aug. 31, 2005 issued in corresponding U.S. Appl. No. 10/308,718.
USPTO Office action dated Aug. 16, 2005 issued in corresponding U.S. Appl. No. 10/373,463.
USPTO Office action dated Jan. 27, 2005 issued in corresponding U.S. Appl. No. 10/373,463.
USPTO Office action dated Aug. 13, 2004 issued in corresponding U.S. Appl. No. 10/373,463.
USPTO Notice of Allowance issued Sep. 26, 2003 in U.S. Appl. No. 10/162,533.
USPTO Notice of Allowance issued May 12, 2003 in U.S. Appl. No. 10/024,077.
USPTO Office Action dated Apr. 1, 2003 issued in U.S. Appl. No. 10/162,533.
USPTO Office action dated Mar. 28, 2003 issued in corresponding U.S. Appl. No. 10/024,077.
USPTO Notice of Allowance issued Sep. 30, 2002 in U.S. Appl. No. 09/846,657.
USPTO Office Action dated Apr. 2, 2002 issued in corresponding U.S. Appl. No. 09/846,657.
USPTO Office Action dated Feb. 27, 2002 issued in corresponding U.S. Appl. No. 09/846,657.
USPTO Office Action dated Jan. 3, 2002 issued in corresponding U.S. Appl. No. 09/846,657.
AU Examiners report dated Jan. 18, 2006 issued in corresponding Australian patnet application No. 2005202099.
AU Examiners report dated Jan. 12, 2007 issued in corresponding Australian patnet application No. 2006202337.
AU Examiners report dated Feb. 21, 2007 issued in corresponding Australian patnet application No. 2005202099.
AU Examiners report dated May 23, 2007 issued in corresponding Australian patnet application No. 2005202099.
AU Notice of Acceptance dated Aug. 6, 2007 in Patent Application No. 20022357284.
EPO supplementary partial search report dated May 10, 2004 issued in corresponding European application 01932833.5-231-/US0114061.
EPO supplementary search report dated Aug. 30, 2004 issued in corresponding European application 01932833.5.
EPO Office Action dated Aug. 23, 2004, received in related EPO application No. 03 026 286.9 (4 pgs).
EPO Office Action dated Mar. 15, 2005, received in related EPO application No. 03 026 286.9, (3 pgs).
EPO Search Report received in related EPO Application No. 03 02 6286.9 dated Feb. 26, 2004 (5pgs).
EPO Search Report received in related EPO Application No. 03 02 6286.9 dated Apr. 27, 2004 (6pgs).
Examination Report dated Feb. 22, 2005 received in corresponding European Application No. 01932833.5 (3pages).
EPO Office Action dated Sep. 22, 2005 issued in corresponding European application 01932833.5-2310.
EPO Office Action dated Sep. 11, 2006 issued in corresponding European application 01932833.5-2310.
International Preliminary Examination Report dated Aug. 19, 2004 issued in corresponding PCT patent application No. PCT/US02/40310.
International Preliminary Examination Report dated Nov. 5, 2002 issued in corresponding PCT patent application No. PCT/US01/14061.
US Office Action issued in related U.S. Appl. No. 10/994,453 dated Feb. 25, 2008.
International Preliminary Examination Report dated Nov. 12, 2002 issued in corresponding PCT patent application No. PCT/US01/48821.
International Preliminary Examination Report dated Sep. 12, 2003 issued in corresponding PCT patent application No. PCT/US02/40310.
International Preliminary Examination Report dated Oct. 27, 2003 issued in corresponding PCT patent application No. PCT/US01/48821.
U.S. Office Action dated Oct. 21, 2008 issued in related U.S. Appl. No. 11/461,240.
U.S. Office Action dated Jun. 25, 2008 issued in related U.S. Appl. No. 11/359,891.
U.S. Office Action dated Sep. 25, 2008 issued in related U.S. Appl. No. 11/326,133.
U.S. Office Action dated Jul. 2, 2008 issued in related U.S. Appl. No. 11/379,151.
European Office Action dated Oct. 6, 2008 issued in related European Patent Application No. 01932833.5-2310.
U.S. Office Action dated Jun. 27, 2008 issued in related U.S. Appl. No. 10/760,965.
International Search Report and Written Opinion dated Oct. 1, 2008 issued in related International Patent Application No. PCT/US08/53194.
International Search Report and Written Opinion dated Oct. 9, 2008 issued in related International Patent Application No. PCT/US07/82262.
European Search Report dated Nov. 4, 2008 issued in related European Patent Application No. 04811836.8-2310.
Habermeyer, “Eclipse, Schaftfreie Schulterprothese Operationsanleitung,” (dated unknown).
U.S. Office Action dated Jan. 9, 2009 issued in related U.S. Appl. No. 10/373,463.
Canadian Office Action dated Dec. 9, 2008 issued in related Canadian Patent Application No. 2407440.
Supplemental European Search Report dated Nov. 6, 2008 issued in related European Patent Application No. 05791453.3-2310.
Japanese Office Action dated Dec. 19, 2008 issued in Japanese Patent Application No. 2006501193.
Japanese Office Action dated Jan. 13, 2009 issued in Japanese Patent Application No. 2003552147.
International Search Report dated Jan. 30, 2006 issued in related International Patent Application No. PCT/US04/39181.
U.S. Office Action dated Mar. 27, 2009 issued in related U.S. Appl. No. 11/169,326.
European Office Action dated Feb. 26, 2009 in related European Patent Application No. 05791453.3.
Australian Office Action dated Apr. 9, 2010 issued in related Australian Patent Application No. 2005260590.
U.S. Office Action dated Mar. 2, 2010 issued in related U.S. Appl. No. 11/169,326.
U.S. Office Action dated Mar. 9, 2010 issued in related U.S. Appl. No. 11/359,892.
Australian Office Action dated Feb. 26, 2010 issued in related Australian Patent Application No. 2008207536.
Supplemental Notice of Allowance dated Feb. 2, 2010 issued in related U.S. Appl. No. 10/373,463.
European office communication dated Feb. 10, 2010 issued in European Patent Application No. 09002088.4-2310.
International Preliminary Report on Patentability dated Aug. 20, 2009 issued in related International Patent Application No. 2008053194.
Notice of Allowance dated Aug. 25, 2009 issued in related U.S. Appl. No. 11/379,151.
Notice of Allowance dated Aug. 27, 2009 issued in related U.S. Appl. No. 10/760,965.
Notice of Allowance dated Dec. 12, 2011 issued in U.S. Appl. No. 12/582,345, 19 pages.
U.S. Office Action dated Dec. 22, 2011 issued in U.S. Appl. No. 11/623,513, 8 pages.
U.S. Office Action dated Dec. 27, 2011 issued in U.S. Appl. No. 12/620,309, 10 pages.
U.S. Office Action dated Jan. 4, 2012 issued in U.S. Appl. No. 12/001,473, 19 pages.
U.S. Office Action dated Jan. 10, 2012 issued in U.S. Appl. No. 12/031,534, 9 pages.
U.S. Office Action dated Jan. 18, 2012 issued in U.S. Appl. No. 12/778,055, 9 pages.

(56) References Cited

OTHER PUBLICATIONS

European Office Action dated Jan. 23, 2012 issued in European Patent Application No. 01 997 077.1, 3 pages.
Habermeyer, Peter, ATOS News, Oct. 2005, "The Artificial Limb "Eclipse"—A new draft without shank in the implantation of artificial shoulder limbs", cover page w/pp. 40-41, with English translation dated Jan. 13, 2006 (2 pgs).
Thermann, et al, ATOS Newsletter, Jun. 2005, Aktuelle Thernen, (16 pages).
Gray, Henry, Anatomy of the Human Body, 1918, 6d. The Foot 1. The Tarsus, II. Osteology, cover page and 12 pgs, ww. Bartleby.com/107/63.html#i268 Oct. 25, 2004.
Chainsaw, Wikipedia, the free encyclopedia, http://en.wikipedia.org/w/index.php?title=Chainsaw&printable=yes, Jun. 26, 2007 (3 pages).
Cannulated Hemi Implants from Vielex, (3 pages).
APTA | Knee,/http://www.apta.org/AM/PrinerTemplate.cfm?Section=Home&TEMPLATE=/CM/HTMLDisplay.dfg& . . . Jun. 25, 2007 (1page).
Arthrosurface, Restoring the Geometry of Motion, HemiCAP Patello—Femoral Resurfacing System (19 pages).
Anatomical Arthroplastie, Total Evolutive Shoulder System T.E.S.S., Biomet France, Biomet Europe (4 pages).
American Machinist, Full-radius milling cutters, http://www.americanmachinist.com/Classes/Article/ArticleDraw_P.aspx, Jun. 26, 2007 (1 page).
Chuck (engineering),Wikipedia, the free encyclopedia, http://en.wikipedia.org/w/index.php?title=Chuck_%28engineering%29 &printable=yes, Jun. 25, 2007, (4 pages).
Dovetail Rails, http://www.siskiyou.com/MDRSeries.htm, Jun. 25, 2007 (2 pages).
Knee Resurfacing, Permedica, GKS, Global Knee System. Cod. 104570 vers 1.0 del Mar. 15, 2006 (8pages).
Major Biojoint System, La nuova frontiera della biointegrazione naturale, Finceramica Biomedical solutions (4 pages).
Makita Industrial Power Tools, Product Details Print Out, Chain Mortiser, http://www.makita.com/menu.php?pg=product_det_prn &tag=7104L, Jun. 26, 2007 (3pgs).
Milling machine, Wikipedia, the free encyclopedia, http://en.wikipedia.org/w/index.php?title=Milling_machine&printable=yes, Jun. 26, 2007 (4 pages).
Mortise and tenon, Wikipedia, the free encyclopedia, http://en.wikipedia.org/w/index.php?title=Mortise_and_tenon &printable=yes, Jun. 25, 2007 (3 pages).
Oka et al, "Development of artificial articular cartilage", Proc Instn Mech Engrs vol. 214 Part H, 2000 pp. 59-68 (10 pages).
Reversed Arthroplastie, Total Evolutive Shoulder System T.E.S.S., Biomet France, Biomet Europe (4 pages).
M. Siguier, MD et al, "Preliminary Results of Partial Surface Replacement of the Femoral Head in Osteonecrosis", The Jorunal of Arthroplasty, vol. 14, No. 1, 1999, pp. 45-51.
T. Siguier, MD et al, Partial Resurfacing Arthroplasty of the Femoral Head in Avascular Necrosis, Clinical Orthopaedics and Related Research, No. 386, 2001, pp. 85-92.
Suganuma, et al—"Arthroscopically Assisted Treatment of Tibial Plateau Fractures", Arthroscopy: The Journal of Arthroscopic and Related Surgery, vol. 20, No. 10, Dec. 2004, pp. 1084-1089 (6 pages).
The Mini Uni: A New Solution for Arthritic Knew Pain and Disability, AORI, 4 pages, www.aori.org/uniknee.htm Apr. 20, 2004.
The Stone Clinic, Orthopaedic Surgery Sports Medicine and Rehabilitation, Unicompartmental Replacement (partial knee joint replacement), Aug. 21, 2000, 3 pages, www.stoneclinic.com/unicopartrepl.htm, Apr. 20, 2004.
Ushio et al, "Partial hemiarthroplasty for the treatment of osteonecrosis of the femoral hear", An Experimantal Study in the Dog, The Journal of Bone and Joint Surgery, vol. 85-B, No. 6, Aug. 2003, pp. 922-930 (9 pages).
Russell E. Windsor, MD, In-Depth Topic Reviews, Unicompartmental Knee Replacement, Nov. 7, 2002, 9 pages.
Yaw angle, Wikipedia, the free encyclopedia, http://en.wikipedia.org/w/index.php?title=Yaw_angle&printable=yes, Jun. 25, 2007 (1 page).
Japanese Notice of Reasons for Rejection dated Jun. 1, 2010 issued in related Japanese Patent Application No. 2003394702.
European Office Action dated Jun. 1, 2010 issued in related European Patent Application No. 04811836.8-2310.
Japanese Notice of Reasons for Rejection dated Jun. 29, 2010 issued in related Japanese Patent Application No. 2007519417.
Australian Office Action dated Jun. 11, 2010 issued in related Australian Patent Application No. 2005277078.
International Search Report dated Jun. 9, 2010 issued in related International Patent Application No. PCT/US2010/031594.
European Office Action dated May 7, 2010 issued in related European Patent Application No. 06733631.3-2310.
International Search Report dated Jun. 18, 2010 issued in related International Patent Application No. PCT/US2010/031602.
U.S. Office Action dated Jun. 8, 2010 issued in related U.S. Appl. No. 11/209,170.
Ascension Orthopedics, Inc., Ascension Orthopedics Announces Market Release of TITAN™ Inset Mini Glenoid, PR Newswire, downloaded from internet Jul. 18, 2011, http://www.orthospinenews.com/ascension-orthopedics-announces-market-release-of-titan™-inset-mini-glenoid, Jul. 6, 2011, 2 pages.
PCT International Preliminary Report on Patentability dated Sep. 9, 2011 issued in PCT Patent Application No. PCT/US2010/025464, 7 pages.
Notice of Allowance dated Nov. 26, 2010 issued in related U.S. Appl. No. 11/209,170.
Supplemental Notice of Allowance dated Dec. 8, 2010 issued in related U.S. Appl. No. 11/209,170.
Notice of Allowance dated Dec. 13, 2010 issued in related U.S. Appl. No. 12/397,095.
Notice of Allowance dated Jan. 5, 2011 issued in related U.S. Appl. No. 11/326,133.
Supplemental Notice of Allowance dated Jan. 5, 2011 issued in related U.S. Appl. No. 11/326,133.
Canadian Office Action dated Jan. 7, 2011 issued in related Canadian Patent Application No. 2407440.
European Office Action dated Dec. 23, 2010 issued in related European Patent Application No. 028051882.9-2310.
European Office Action dated Dec. 30, 2010 issued in related European Patent Application No. 01997077.1-2310.
Examination Report dated Dec. 30, 2011 issued in European Patent Application No. 09 002 088.4, 6 pages.
Intent to Grant dated Feb. 17, 2012 issued in European Patent Application No. 02 805 182.9, 5 pages.
Notice of Allowance dated Feb. 24, 2012 issued in U.S. Appl. No. 12/027,121, 9 pages.
Intent to Grant dated Feb. 29, 2012 issued in European Patent Application No. 10 012 693.7, 5 pages.
Supplemental Notice of Allowance dated Mar. 2, 2012 issued in U.S. Appl. No. 12/027,121, 2 pages.
Office Action dated Mar. 2, 2012 issued in U.S. Appl. No. 12/713,135, 7 pages.
Extended Search Report dated Feb. 22, 2011 issued in European Patent Application No. 10012693.7, 8 pages.
Notice of Allowance dated Mar. 2, 2011 issued in Australian Patent Application No. 2008207536, 3 pages.
Notice of Allowance dated Mar. 15, 2011 issued in U.S. Appl. No. 11/551,912, 7pages.
U.S. Office Action dated Apr. 11, 2011 issued in U.S. Appl. No. 11/779,044, 10 pages.
Notice of Allowance dated Apr. 28, 2011 issued in U.S. Appl. No. 12/027,121, 9 pages.
U.S. Office Action dated Mar. 29, 2012 issued in U.S. Appl. No. 10/789,545, 7 pages.
U.S. Office Action dated Apr. 18, 2012 issued in U.S. Appl. No. 12/725,181, 9 pages.
U.S. Notice of Allowance dated May 31, 2012 issued in U.S. Appl. No. 11/623,513, 5 pages.
U.S. Office Action dated May 11, 2011 issued in U.S. Appl. No. 11/623,513, 12 pages.

(56) References Cited

OTHER PUBLICATIONS

U.S. Office Action dated May 11, 2011 issued in U.S. Appl. No. 12/001,473, 18 pages.
U.S. Office Action dated May 16, 2011 issued in U.S. Appl. No. 12/582,345, 9 pages.
International Search Report and Written Opinion dated May 19, 2011 issued in PCT Application No. PCT/US2011/027451, 11 pages.
Canadian Notice of Allowance dated Jun. 1, 2011 issued in Canadian Patent Application No. 2,470,936, 1 page.
Examiner interview summary dated Jul. 1, 2011 issued in European Patent Application No. 02 805 182.9, 3 pages.
U.S. Final Office Action dated Jul. 8, 2011 issued in U.S. Appl. No. 11/169,326, 26 pages.
Canadian Office Action dated Jul. 29, 2010 issued in related Canadian Patent Application No. 2470936.
Supplemental European Search Report dated Aug. 9, 2010 issued in related European Patent Application No. 04714211.2-2300.
Australian Office Action dated Aug. 23, 2010 issued in related Australian Patent Application No. 2006203909.
U.S. Office Action dated Aug. 30, 2006 issued in related U.S. Appl. No. 10/618,887.
U.S. Office Action dated Jan. 15, 2008 issued in related U.S. Appl. No. 10/618,887.
U.S. Office Action dated May 18, 2009 issued in related U.S. Appl. No. 11/209,170.
U.S. Office Action dated May 28, 2009 issued in related U.S. Appl. No. 11/359,891.
U.S. Office Action dated May 13, 2009 issued in related U.S. Appl. No. 11/359,892.
International Search Report and Written Opinion dated Jun. 1, 2009 issued in related International Patent Application No. PCT/US2009/035889.
International Preliminary Report and Patentability dated May 7, 2009 issued in related International Patent Application No. PCT/US2007/082262.
Supplemental European Search Report dated May 28, 2009 issued in related International European Patent Application No. 01997077.1.
Supplemental European Search Report dated May 11, 2009 issued in related International European Patent Application No. 02805182.9.
Notice of Allowance dated Feb. 20, 2009 issued in related U.S. Appl. No. 10/618,887.
International Preliminary Report on Patentability dated Sep. 1, 2011 issued in PCT International Patent Application No. PCT/US2010/025095, 8 pages.
International Preliminary Report on Patentability dated Oct. 27, 2011 issued in PCT International Patent Application No. PCT/US2010/031602, 8 pages.
International Preliminary Report on Patentability dated Oct. 27, 2011 issued in PCT International Patent Application No. PCT/US2010/031594, 7 pages.
U.S. Office Action dated Nov. 1, 2011 issued in U.S. Appl. No. 12/713,135, 10 pages.
U.S. Notice of Allowance dated 11/23/11 issued in U.S. Appl. No. 11/623,513, 19 pages.
U.S. Office Action dated Nov. 28, 2011 issued in U.S. Appl. No. 12/711,039, 6 pages.
Notice of Allowability dated Oct. 9, 2012, issued in U.S. Appl. No. 12/713,135, 5 pages.
Notice of Allowability dated October11, 2012, issued in U.S. Appl. No. 11/169,326 2 pages.
U.S. Office Action dated Oct. 23, 2012, issued in U.S. Appl. No. 13/042,382, 17 pages.
U.S. Office Action dated Oct. 24, 2012, issued in U.S. Appl. No. 12/942,923, 9 pages.
U.S. Office Action dated Oct. 31 2012, issued in U.S. Appl. No. 13/075,006, 9 pages.
Notice of Allowance dated Nov. 13, 2012 issued in U.S. Appl. No. 12/725,181, 5 pages.
Preliminary Report on Patentability dated Sep. 20, 2012 issued in PCT Patent Application No. PCT/US2011/027451, 3 pages.
McCarty, III., et al., "Nonarthoplasty Treatment of Glenohumeral Cartilage Lesions," Arthroscopy, The Journal of Arthroscopic and related Surgery, vol. 21, No. 9; Sep. 2005 (pp. 1131-1142).
Bushnell, et al., "Bony Instability of the Shoulder," Arthroscopy, The Journal of Arthroscopic and related Surgery, vol. 24, No. 9; Sep. 2005 (pp. 1061-1073).
Scalise, et al., "Resurfacing Arthroplasty of the Humerus: Indications, Surgical Technique, and Clinical Results," Techniques in Shoulder and Elbow Surgery 8(3):152-160; 2007.
Davidson, et al., "Focal Anatomic Patellofemoral Inlay Resurfacing: Theoretic Basis, Surgical Technique, and Case Reports," Orthop. Clin. N. Am., 39 (2008) pp. 337-346.
Provencher, et al., "Patellofemoral Kinematics After Limited Resurfacing of the Trochlea," The Journal of Knee Surgery, vol. 22 No. 2 (2008) pp. 1-7.
Dawson, et al., "The Management of Localized Articular Cartilage Lesions of the Humeral Head in the Athlete," Operative Techniques in Sports Medicine, vol. 16, Issue 1, pp. 14-20 (2008).
Uribe, et al., "Partial Humeral Head Resurfacing for Osteonecrosis," Journal of Shoulder and Elbow Surgery, (2009) 6 pages.
Burks, "Implant Arthroplasty of the First Metatarsalphalangeal Joint," Clin. Podiatr. Med. Surg., 23 (2006) pp. 725-731.
Hasselman, et al., "Resurfacing of the First Metatarsal Head in the Treatment of Hallux Rigidus," Techniques in Foot & Ankle Surgery 7(1):31-40, 2008.
Gelenkoberflachen, et al., "Partial hemi-resurfacing of the hip joint—a new approach to treat local osteochondral defects?" Biomed Tech 2006; 51:371-376 (2006).
Sullivan, "Hallux Rigidus: MTP Implant Arthroplasty," Foot Ankle Clin. N. Am. 14 (2009) pp. 33-42.
Cook, et al., "Meta-analysis of First Metatarsophalangeal Joint Implant Arthroplasty," Journal of Foot and Ankle Surgery, vol. 48, Issue 2, pp. 180-190 (2009).
Derner, "Complications and Salvage of Elective Central Metatarsal Osteotomies," Clin. Podiatr. Med. Surg. 26 (2009) 23-35.
Kirker-Head, et al., "Safety of, and Biological Functional Response to, a Novel Metallic Implant for the Management of Focal Full-Thickness Cartilage Defects: Preliminary Assessment in an Animal Model Out to 1 year," Journal of Orthopedic Research, May 2006 pp. 1095-1108.
Beecher, et al. "Effects of a contoured articular prosthetic device on tibiofemoral peak contact pressure: a biomechanical study," Knee Surg Sports Traumatol Arthrosc. Jan. 2008; 16(1): 56-63.
United States Office Action dated May 13, 2009 issued in related U.S. Appl. No. 11/359,892.
United States Office Action dated May 18, 2009 issued in related U.S. Appl. No. 11/209,170.
United States Office Action dated May 1, 2009 issued in related U.S. Appl. No. 11/461,240.
Australian Office Action dated Jan. 29, 2009 issued in related Australian Patent Application No. 2004216106.
European Search Report dated Apr. 22, 2009 issued in related European Patent Application No. 09002088.4.
Notice of Reasons for Rejection dated Nov. 17, 2009 issued in Japanese Patent Application No. 2007-519417.
European Search Report dated Dec. 3, 2009 issued in related European Patent Application No. 06735827.5.
Office Action dated Dec. 24, 2009 issued in related U.S. Appl. No. 10/994,453.
Supplemental Notice of Allowance dated Nov. 25, 2009 issued in related U.S. Appl. No. 10/373,463.
Notice of Reasons for Rejection issued in related Japanese Patent Application No. 2003-394702 mailed Jul. 21, 2009.
Notice of Reasons for Rejection issued in related Japanese Patent Application No. 20-541615 mailed May 26, 2009.
International Preliminary Report on Patentability issued in related International Patent Application No. PCT/US2007/025284 dated Jun. 25, 2009.
Office Action issued in related Australian Patent Application No. 2007216648 dated Jul. 28, 2009.
European Search Report dated Jul. 10, 2009 issued in related European Patent Application No. 09002088.4.

(56) References Cited

OTHER PUBLICATIONS

U.S. Office Action dated Sep. 2, 2009 issued in relation U.S. Appl. No. 10/994,453.
U.S. Office Action dated Oct. 5, 2009 issued in relation U.S. Appl. No. 10/789,545.
U.S. Office Action dated Oct. 15, 2009 issued in relation U.S. Appl. No. 11/551,912.
U.S. Office Action dated Oct. 14, 2009 issued in relation U.S. Appl. No. 11/461,240.
International Preliminary Report on Patentability dated Aug. 20, 2009 issued in related International Patent Application No. PCT/US2008/053194.
Australian Notice of Allowance dated Oct. 29, 2009 issued in related Australian Patent Application No. 2007216648.
Notice of Allowance dated Oct. 9, 2009 issued in related U.S. Appl. No. 10/373,463.
Australian Office Action dated Oct. 29, 2009 issued in related Australian Patent Application No. 2007203623.
Japanese Notice of Reasons for Rejection dated Sep. 8, 2009 issued in related Japanese Patent Application No. 2003552147.
International Search Report and Written Opinion dated Apr. 21, 2010 issued in related International Patent Application No. PCT/US2010/025095.
International Search Report and Written Opinion dated May 3, 2010 issued in related International Patent Application No. PCT/US2010/025464.
European Office Action dated Apr. 13, 2010 issued in related European Patent Application No. 02805182.9-2310.
European Office Action dated Mar. 25, 2010 issued in related European Patent Application No. 01997077.1-2310.
U.S. Office Action dated May 18, 2010 issued in related U.S. Appl. No. 12/415,503.
Extended Search Report dated Jul. 3, 2012 issued in European Patent Application No. 12002103.5, 5 pages.
Decision to Grant dated Jul. 26, 2012 issued in European Patent Application No. 10012693.7, 1 page.
Final Office Action dated Aug. 13, 2012 issued in U.S. Appl. No. 12/711,039, 12 pages.
Office Action dated Aug. 14, 2012 issued in U.S. Appl. No. 12/001,473, 17 pages.
Office Action dated Aug. 20, 2012 issued in U.S. Appl. No. 13/037,998, 11 pages.
Office Action dated Aug. 21, 2012 issued in U.S. Appl. No. 13/043,430, 11 pages.
U.S. Office Action dated Aug. 28, 2012 issued in U.S. Appl. No. 12/762,948, 12 pages.
U.S. Notice of Allowance dated Sep. 4, 2012 issued in U.S. Appl. No. 11/169,326, 6 pages.
Notice of Allowance dated Sep. 9, 2010 issued in related U.S. Appl. No. 10/994,453.
Office Action dated Sep. 21, 2010 issued in related U.S. Appl. No. 11/169,326.
Office Action dated Sep. 29, 2010 issued in related U.S. Appl. No. 11/461,240.
Office Action dated Oct. 11, 2010 issued in related Australian Patent Application No. 2006216725.
International Preliminary Report on Patentability dated Sep. 16, 2010 issued in related International Patent Application No. PCT/US2009/035889.
Supplemental Notice of Allowance dated Oct. 13, 2010 issued in related U.S. Appl. No. 10/994,453.
Supplemental Notice of Allowance dated Oct. 6, 2010 issued in related U.S. Appl. No. 12/415,503.
U.S. Office Action dated Oct. 15, 2010 received in related U.S. Appl. No. 12/027,121.
U.S. Supplemental Notice of Allowance dated Oct. 28, 2010 issued in related U.S. Appl. No. 12/415,503.
European Search Report dated Nov. 4, 2010 issued in related European Patent Application No. 07862736.1-1269.
Office Action dated Sep. 2, 2010 issued in related U.S. Appl. No. 12/415,503.
Office Action dated Aug. 30, 2010 issued in related U.S. Appl. No. 12/397,095.
Office Action dated Jul. 21, 2010 issued in related U.S. Appl. No. 11/551,912.
Office Action dated Aug. 5, 2010 issued in related U.S. Appl. No. 11/325,133.
Notice of Allowance dated Aug. 6, 2010 issued in related U.S. Appl. No. 11/359,892.
European Office Action dated Apr. 16, 2013 issued in European Patent Application No. 12 002 103.5, 5 pages.
European Office Action dated May 15, 2013 issued in European Patent Application No. 05 763 817.3, 4 pages.
Decision to Grant dated Sep. 19, 2013 issued in European Patent Application No. 07862736.1, 1 page.
Extended European Search report mailed Dec. 10, 2012 issued in European Patent Application No. 07844549.1, 6 pages.
Supplementary European Search Report dated Jan. 3, 2013 issued in European Patent Application No. 05763817.3, 3 pages.
Great Britain Examination Report dated Feb. 6, 2013 issued in Great Britain Patent Application No. 1114417.7, 2 pages.
Supplementary European Search Report dated Feb. 18, 2013 issued in European Patent Application No. 08729178.7, 10 pages.
Canadian Office Action dated Dec. 13, 2012 issued in Canadian Patent Application No. 2,407,440, 6 pages.
International Search Repoort and Written Opinion dated Mar. 8, 2013 issued in PCT Patent Application No. PCT/US12/71199, 13 pages.
U.S. Office Action dated Apr. 15, 2013 issued in U.S. Appl. No. 13/470,678, 10 pages.
U.S. Office Action dated Apr. 22, 2013 issued in U.S. Appl. No. 12/001,473, 16 pages.
U.S. Office Action dated Apr. 23, 2013 issued in U.S. Appl. No. 13/037,998, 8 pages.
European Intent to Grant dated Apr. 29, 2013 issued in European Patent Application No. 07 862 736.1, 7 pages.
U.S. Notice of Allowance dated May 9, 2013 issued in U.S. Appl. No. 12/725,181, 6 pages.
U.S. Office Action dated May 15, 2013 issued in U.S. Appl. No. 12/762,948, 10 pages.
U.S. Office Action dated Jul. 11, 2013 issued in U.S. Appl. No. 12/711,039, 10 pages.
U.S. Notice of Allowance dated Jul. 29, 2013 issued in U.S. Appl. No. 12/725,181, 7 pages.
U.S. Final Office Action dated Jul. 30, 2013 issued in U.S. Appl. No. 13/075,006, 10 pages.
U.S. Corrected Notice of Allowance dated Jul. 30, 2013 issued in U.S. Appl. No. 11/623,513, 2 pages.
Corrected Notice of Allowability dated Sep. 10, 2013 issued in U.S. Appl. No. 13/043,430, 7 pages.
U.S. Final Office Action dated Jun. 5, 2013 issued in U.S. Appl. No. 12/942,923, 26 pages.
U.S. Final Office Action dated Jun. 24, 2013 issued in U.S. Appl. No. 13/042,382, 28 pages.
U.S. Notice of Allowance dated Jun. 14, 2013 issued in U.S. Appl. No. 13/043,430, 10 pages.
U.S. Office Action dated Aug. 13, 2014, issued in U.S. Appl. No. 12/762,948, 12 pages.
U.S. Notice of Allowance dated Aug. 21, 2014, issued in U.S. Appl. No. 13/075,006, 5 pages.
U.S. Office Action dated Sep. 18, 2014, issued in U.S. Appl. No. 13/785,867, 8 pages.
U.S. Notice of Allowance dated Oct. 6, 2014, issued in U.S. Appl. No. 12/942,923, 5 pages.
Office Action dated Mar. 3, 2015, issued in U.S. Appl. No. 12/979,992, 11 pages.
Notice of Allowance dated Jan. 21, 2015, issued in U.S. Appl. No. 13/752,858, 7 pages.
Notice of Allowability dated Feb. 19, 2015, issued in U.S. Appl. No. 13/037,929, 2 pages.
U.S. Office Action dated Feb. 19, 2015, issued in U.S. Appl. No. 14/035,061, 6 pages.

(56) References Cited

OTHER PUBLICATIONS

Notice of Allowance dated Feb. 25, 2015, issued in U.S. Appl. No. 13/436,188, 8 pages.
U.S. Office Action issued in U.S. Appl. No. 13/438,095, dated Nov. 4, 2014, 11 pages.
International Search Report and Written Opinion issued in PCT Patent Application Serial No. PCT/US14/34157, dated Nov. 4, 2014, 12 pages.
European Extended Search Report issued in European Patent Application Serial No. 10765332.1, dated Nov. 10, 2014, 6 pages.
U.S. Office Action issued in U.S. Appl. No. 12/711,039, dated Nov. 10, 2014, 10 pages.
European Extended Search Report issued in European Patent Application Serial No. 10746863.9, dated Nov. 13, 2014, 5 pages.
European Decision to Grant issued in European Patent Application Serial No. 12002103.5, dated Nov. 20, 2014, 1 page.
European Office Action issued in European Patent Application No. 08 729 178.7, dated Nov. 25, 2014, 4 pages.
U.S. Notice of Allowance issued in U.S. Appl. No. 13/037,929, dated Dec. 11, 2014, 5 pages.
U.S. Office Action dated Apr. 29, 2014, issued in U.S. Appl. No. 13/037,929, 11 pages.
U.S. Office Action dated May 19, 2014, issued in U.S. Appl. No. 13/436,188, 10 pages.
U.S. Office Action dated May 28 2014, issued in U.S. Appl. No. 13/752,858, 8 pages.
U.S. Office Action dated Jun. 4, 2014, issued in U.S. Appl. No. 12/762,920, 10 pages.
Notice of Allowance dated Jun. 19, 2014, issued in U.S. Appl. No. 13/470,678, 5 pages.
Intent to Grant dated Jun. 27, 2014, issued in European Patent Application No. 12 002 103.5, 6 pages.
U.S. Office Action dated Jul. 7, 2014, issued in U.S. Appl. No. 121/979,992, 6 pages.
U.S. Office Action dated Jul. 7, 2014, issued in U.S. Appl. No. 12/001,473, 15 pages.
International Preliminary Report on Patentability dated Jan. 15, 2015, issued in PCT Patent Application No. PCT/US2013/048569, 9 pages.
Canadian Office Action dated Feb. 27, 2015 issued in Canadian Patent Application Serial No. 2,407,440, 7 pages.
U.S. Office Action dated Oct. 8, 2013 issued in U.S. Appl. No. 13/438,095, 8 pages.
International Search Report and Written Opinion dated Oct. 22, 2013 issued in PCT International Patent Application No. PCT/US2013/048569, 15 pages.
Notice of Allowance dated Oct. 30, 2013 issued in U.S. Appl. No. 13/037,998, 28 pages.
U.S. Final Office Action dated Dec. 5, 2013 issued in U.S. Appl. No. 13/470,678, 8 pages.
U.S. Office Action dated Dec. 12, 2013 issued in U.S. Appl. No. 12/979,992, 12 pages.
U.S. Office Action dated Dec. 17, 2013 issued in U.S. Appl. No. 12/001,473, 21 pages.
U.S. Office Action dated Feb. 5, 2014, issued in U.S. Appl. No. 13/438,095, 9 pages.
U.S. Office Action dated Feb. 7, 2014, issued in U.S. Appl. No. 13/075,006, 9 pages.
Australian Examination Report dated Feb. 7, 2014, issued in Australian Patent Application No. 2010236182, 3 pages.
Australian Examination Report dated Feb. 14, 2014, issued in Australian Patent Application No. 2011222404, 3 pages.
European Extended Search Report dated Feb. 24, 2014, issue in European Patent Application No. 09716273.9, 7 pages.
Australian Examination Report dated Feb. 28, 2014, issued in Australian Patent Application No. 2010217907, 3 pages.
U.S. Final Office Action dated Mar. 20, 2014, issued in U.S. Appl. No. 12/711,039, 17 pages.
European Examination Report dated Mar. 20, 2014, issued in European Patent Application No. 12 002 103.5, 3 pages.
U.S. Office Action dated Mar. 21, 2014, issued in U.S. Appl. No. 12/942,923, 6 pages.
U.S. Notice of Allowance dated Apr. 1, 2014, issued in U.S. Appl. No. 13/470,678, 7 pages.
Australian Examination Report dated Apr. 3, 2014, issued in Australian Patent Application No. 2010217907, 3 pages.
Intent to Grant dated Jul. 8, 2015, issued in European Patent Application No. 08 729 178.7, 7 pages.
Extended Search Report dated Sep. 9, 2015, issued in European Patent Application No. 11751521.3, 13 pages.
Partial supplementary European search report dated Mar. 25, 2015, issued in EP Patent Application No. 11751521.3, 6 pages.
U.S. Office Action dated May 1, 2015, issued in U.S. Appl. No. 14/133,943, 25 pages.
U.S. Examiner interview summary dated Apr. 8, 2015, issued in U.S. Appl. No. 12/001,473, 4 pages.
U.S. Final Office Action dated Jun. 2, 2015, issued in U.S. Appl. No. 12/001,473, 18 pages.
U.S. Supplemental Notice of Allowance dated Apr. 21, 2015, issued in U.S. Appl. No. 13/436,188, 6 pages.
U.S. Final Office Action dated Apr. 28, 2015, issued in U.S. Appl. No. 13/785,867, 8 pages.
U.S. Final Office Action dated May 22, 2015, issued in U.S. Appl. No. 13/438,095, 7 pages.
U.S. Office Action dated Jun. 25, 2015, issued in U.S. Appl. No. 12/711,039, 10 pages.
U.S. Final Office Action dated Jul. 7, 2015, issued in U.S. Appl. No. 12/762,948, 15 pages.
Notice of Allowance dated Jul. 31, 2015, issued in U.S. Appl. No. 13/438,095, 8 pages.
U.S. Final Office Action dated Sep. 17, 2015, issued in U.S. Appl. No. 14/035,061, 10 pages.
European Office Action dated Jan. 11, 2010 issued in related European Patent Application No. 2005218302.
U.S. Office Action dated Jan. 25, 2010 issued in related U.S. Appl. No. 11/326,133.
Notice of Allowance issued in corresponding U.S. Appl. No. 10/618,887 dated Sep. 13, 2007.
International Preliminary Report on Patentability and Written Opinion dated May 22, 2006 in corresponding PCT patent application No. PCT/US04/039181.
English language translation of Japanese Office Action dated Aug. 9, 2007 issued in corresponding Japanese application No. 2003-552148.
Canadian Office Action dated Jan. 2, 2008 issued in corresponding Canadian Application No. 2407440.
International Preliminary Report on Patentability and Written Opinion dated Mar. 1, 2007 in corresponding PCT patent application No. PCT/US05/030120.
International Preliminary Report on Patentability and Written Opinion dated Jun. 28, 2007 in corresponding PCT patent application No. PCT/US2005/005980.
International Preliminary Report on Patentability and Written Opinion dated Jul. 19, 2007 in corresponding PCT patent application No. PCT/US2006/000380.
International Search Report dated Dec. 27, 2001 issued in corresponding PCT patent application No. PCT/US01/14061.
Office Action issued in corresponding U.S. Appl. No. 10/741,044 dated Oct. 26, 2005.
International Search Report dated May 23, 2003 issued in corresponding PCT patent application No. PCT/US02/40310.
International Search Report and Written Opinion dated Dec. 30, 2004 issued in corresponding PCT patent application No. PCT/US04/05539.
International Search Report and Written Opinion dated Jan. 30, 2006 issued in corresponding PCT patent application No. PCT/US04/39181.
International Search Report and Written Opinion dated Aug. 30, 2006 issued in corresponding PCT patent application No. PCT/US06/06323.
International Search Report and Written Opinion dated Sep. 29, 2006 issued in corresponding PCT patent application No. PCT/US05/30120.

(56) References Cited

OTHER PUBLICATIONS

International Search Report and Written Opinion dated Nov. 27, 2006 issued in corresponding PCT patent application No. PCT/US06/00380.
International Search Report and Written Opinion dated Nov. 29, 2006 issued in corresponding PCT patent application No. PCT/US05/023200.
International Search Report and Written Opinion dated May 22, 2007 issued in corresponding PCT patent application No. PCT/US05/05980.
International Search Report and Written Opinion dated Aug. 8, 2007 issued in corresponding PCT patent application No. PCT/US06/29875.
Notice of Allowance issued in corresponding U.S. Appl. No. 10/308,718 dated Sep. 11, 2006.
Office Action issued in corresponding U.S. Appl. No. 11/326,133 dated Oct. 17, 2007.
Bale, MD, Reto J., et al, "Osteochondral Lesions of the Talus: Computer=assisted Retrograde Drilling Feasibility and Accuracy in Initial Experriences", (Radiology. 2001;218:278-282)© RSNA, 2001.
Biomet/Copeland, "Aequalis® Resurfacing Head" Tornier, Scientific Vision, Surgical Leadership, SS-401 Jan. 2007.
Kumai, M.D., Tsukasa, et al Arthroscopic Drilling for the Treatment of Osteochondral Lesions of the Talus*, The Journal of Bone & Joint Surgery, American vol. 81:1229-35(1999).
Matsusue, M.D., Yoshitaka, et al, "Arthroscopic Osteochondral Autograft Transplantation for Chondral Lesion of the Tibial Plateau of the Knee", Arthroscopy: The Journal of Arthroscopic and Related Surgery, vol. 17, No. 6 (Jul.-Aug. 2001),:pp. 653-659.
Pill M.S., P.T., Stephan G. et al, "Osteochondritis Dissecans of the Knee: Experiences at the Children's Hospital of Philadelphia and a Review of Literature", the University of Pennsylvania Orthopaedic Journal 14: 25-33, 2001.
Schneider, T., et al, "Arthroscopy of the ankle joint. A list of indications and realistic expectations", Foot and Ankle Surgery 1996 2:189-193, ® 1996 Amette Blackwell SA.
Taranow WS, et al, "Retrograde drilling of osteochondral lesions of the medial talar dome", PubMed, www.pubmed.gov, A service of the National Library of Medicing and the Natinal Institutes of Health, Foot Ankle Int. Aug. 1999; 20 (8):474-80.
Ueblacker, M.D., Peter, et al, "Retrograde Cartilage Transplantation of the Proximal and Distal Tibia", Arthroscopy: The Journal of Arthroscipic and Related Surgery, vol. 20, No. 1 (Jan. 2004),: pp. 73-78.
European Decision to Grant dated Dec. 17, 2015, issued in European Patent Application No. 08729178.7, 2 pages.
International Preliminary Report on Patentability dated Oct. 29, 2015, issued in PCT Patent Application No. PCT/US/2014/034157, 5 pages.
European Examination Report dated Oct. 28, 2015, issued in European Patent Application No. 05 763 817.3, 4 pages.
Partial Supplementary European Search Report dated Nov. 5, 2015, issued in European Patent Application No. 12860168.9, 6 pages.
European Examination Report dated Dec. 7, 2015, issued in European Patent Application No. 10 765 332.1, 4 pages.
US Office Action dated Dec. 8, 2015, issued in U.S Appl. No. 13/796,675, 16 pages.
US Office Action dated Nov. 25, 2015, issued in U.S. Appl. No. 13/863,917, 12 pages.
US Office Action dated Nov. 25, 2015, issued in U.S. Appl. No. 13/723,902, 13 pages.
US Notice of Allowance dated Oct. 30, 2015, issued in U.S. Appl. No. 12/762,920, 8 pages.
US Office Action dated Nov. 17, 2015, issued in U.S. Appl. No. 13/930,737, 9 pages.

* cited by examiner

GLENOID RESURFACING SYSTEM AND METHOD

CROSS-REFERENCE

This application claims the benefit of the filing date of U.S. Provisional No. 61/170,290 filed on Apr. 17, 2009 and U.S. Provisional No. 61/311,605, filed Mar. 8, 2010, the teaching of which are both incorporated by reference herein. This application also relates to U.S. application Ser. No. 12/762, 948, filed Apr. 19, 2010, the teachings of which are incorporated herein by reference.

FIELD

This disclosure relates to devices and methods for the repair of defects that occur in articular cartilage on the surface of bones, particularly the shoulder.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an implant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF DRAWINGS

The above-mentioned and other features of this disclosure, and the manner of attaining them, may become more apparent and better understood by reference to the following description of embodiments described herein taken in conjunction with the accompanying drawings, wherein.

DETAILED DESCRIPTION

According to one embodiment, the present disclosure may feature a system and method for resurfacing at least a portion of an articular surface having a defect by replacing a portion of the articular surface with an implant. The implant may comprise a load bearing surface having a contour and/or shape substantially corresponding to the patient's original articular surface about the defect site which may be configured to engage an adjacent articular surface. The present disclosure will describe a system and method for replacing a portion of the articular surface of the glenoid; however, it should be understood that the system and method according to the present disclosure may also be used to resurface articular surfaces other than the glenoid.

As an initial matter, many of the devices described herein comprise cannulated components configured to be arranged over other components. The degree to which the cannulated passageway (i.e., internal diameter of the passageway/cavity) of a first component corresponds to the external diameter of the component over which it is being placed may be close enough to generally eliminate excessive movement. Excessive movement may be defined as an amount of movement that may result in surgically relevant misalignment of the implant relative to the articular surface.

Figure 1:
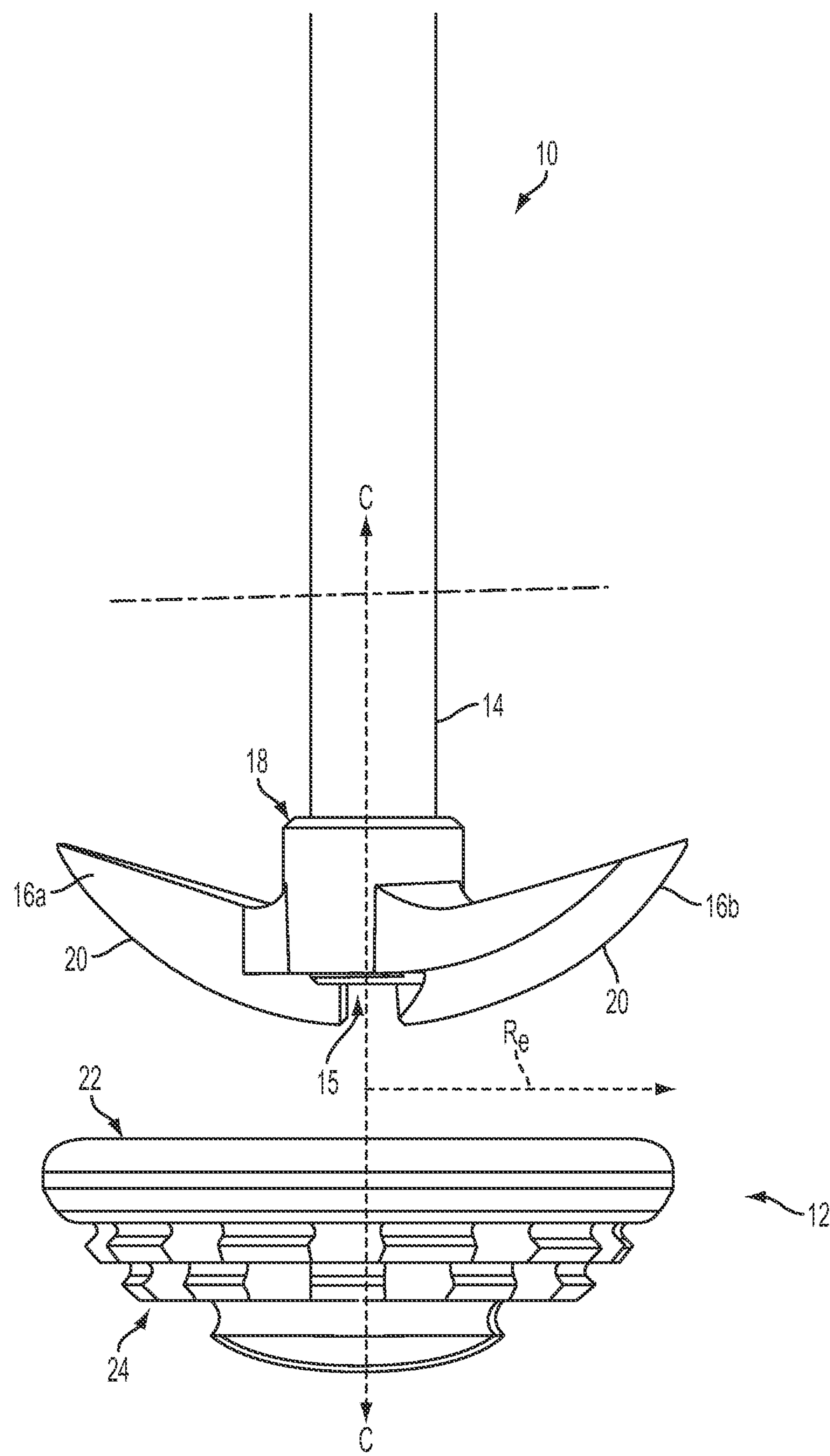
FIG. 1 illustrates a side view of an example of an excision device and an implant.

Referring now to FIG. 1, one embodiment of an excision device 10 and an implant 12 are generally illustrated. As will be explained in greater detail herein, the excision device 10 may be configured to form an implant or excision site within the articular surface (e.g., the glenoid) configured to receive at least a portion of the implant 12. The implant 12 may be configured to replace the articular surface in an area proximate one or more defects. The system and method consistent with the present disclosure may repair a defect on the articular surface of a glenoid without having to replace the entire glenoid.

Accordingly to at least one embodiment, the implant 12 may be configured to replace only a portion of the articular surface proximate the defect site rather than the entire articular surface. As such, the implant 12 may minimize the amount of the articular surface which is operated on thus allowing more of the patient's original articular surface to be unaffected and providing a more physiologically normal joint. The system and method consistent with one embodiment of the present disclosure may allow for "key-hole" surgery in which a minimum number and size of incisions are made. As may be appreciated, "key-hole" surgery may reduce the amount of pain and/or discomfort experienced by the patient and may reduce healing times.

The excision device 10 may include a cannulated shaft 14 defining a passageway 15 configured to be received over at least a portion of a guide pin or the like (not shown). The excision device 10 may also include at least one cutter 16*a*, 16*b* extending radially outwardly and away from a distal end 18 of the shaft 14. Each cutter 16*a*, 16*b* may have a cutting surface 20 configured to create a hemispherical implant site, i.e., an excision site to receive the implant. For example, the cutting surface 20 may have a generally arcuate shape which sweeps towards the proximal end of the shaft 14 as the radius $R_e$ from the shaft 14 increases on the cutter 16*a*, 16*b*. It may be appreciated that the hemi-spherical excision site may exhibit some degree of deviation and the hemi-spherical excision site may be, in some examples, teardrop shaped or pyriform.

The contour of the cutting surfaces 20 may define the contours of the excision site as the cutters 16*a*, 16*b* are rotated about the central axis of the excision site. While the cutting surfaces 20 are illustrated having a generally constant arc or curvature, the cutting surfaces 20 may include one or more protrusions and/or recesses configured to create corresponding radial groove and/or lips/protrusions within the excision site. These radial grooves and/or lips/protrusions on the cutting surfaces 20 may facilitate alignment of the implant 12 and/or may increase the mechanical coupling of the implant 12 within the excision site.

Figure 2:
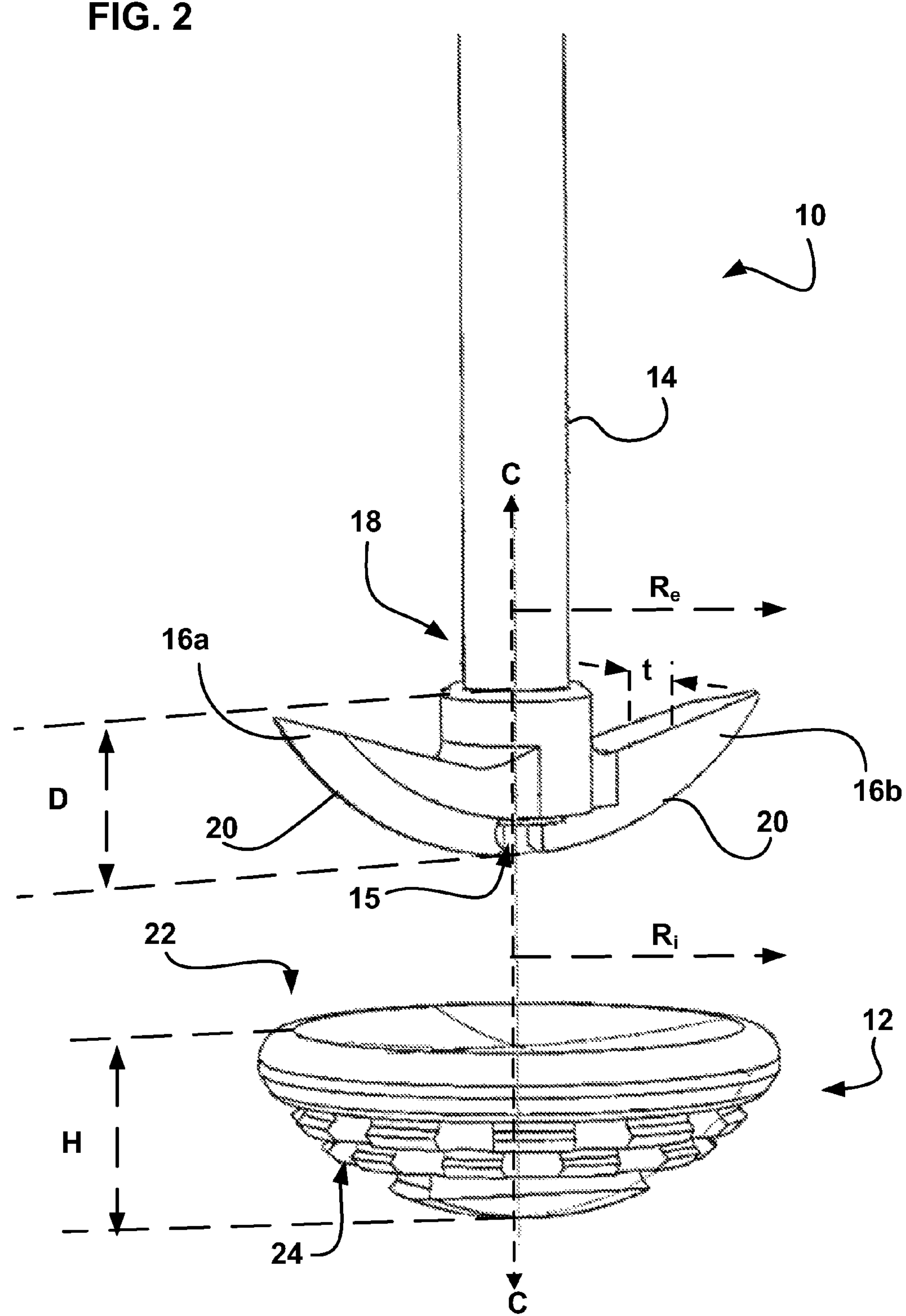
FIG. 2 illustrates a perspective view of an example of an excision device and an implant.

Turning now to FIG. 2, the overall radius $R_e$ of the cutters 16*a*, 16*b* may define the radius of the implant site created by the excision device 10 within the articular surface and may also substantially correspond to the radius $R_i$ of the implant 12. In addition, the depth D of the cutters 16*a*, 16*b* may also define the height of the excision site created by the excision device 10 and may also substantially correspond to the height H of the implant 12. For example, the overall radius $R_e$ of the cutters 16*a*, 16*b* may be between 7.0 mm to 20.0 mm, for example, 7.0 mm to 15.0 mm and/or 10.0 mm to 12.5 mm (including all values and ranges therein) and the depth D may be between 4.0 mm to 10.0 mm, for example, 5 mm (including all values and ranges therein).

According to at least one embodiment, the excision device 10 may include a first and a second cutter 16*a*, 16*b* which may be disposed approximately 180 degrees relative to each other. For example, the cutters 16*a*, 16*b* may extend generally radially outwardly from the shaft about a first and a second generally opposite side of the distal end 18 of the shaft 14. The cutters 16*a*, 16*b* may also have a generally slim profile configured to be disposed between two adjacent articular surfaces as explained further herein. For example, the cutters 16*a*, 16*b* may have a cross-sectional thickness (t) of 0.5 mm to 3.0 mm, for example, 2.0 mm (including all values and ranges therein). In one embodiment the at least one cutter may provide a generally hemispherical excision site regardless of the angle which the guide pin is disposed relative to the articular surface 54.

Figure 3:
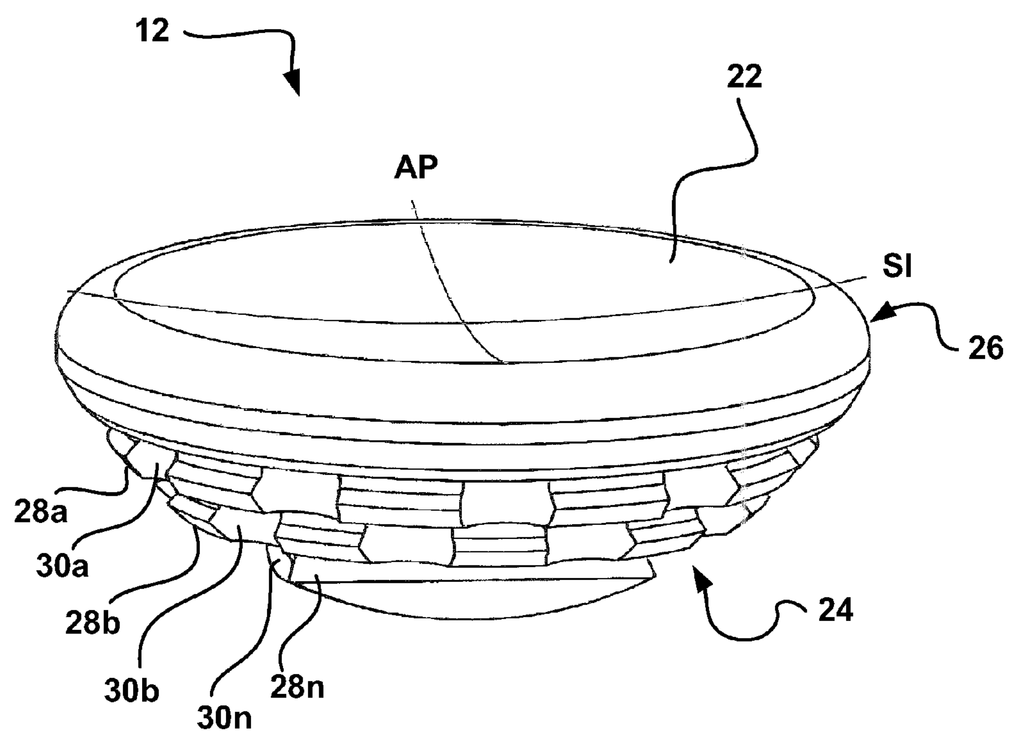
FIG. 3 illustrates an example of an implant.

The implant 12 may include a load bearing surface 22 and a bone facing surface 24. Turning now to FIG. 3, a top perspective view of an implant 12 consistent with at least one embodiment herein is generally illustrated. The load bearing surface 22 may have a contour substantially corresponding to or based on the contour of the patient's articular surface being replaced (i.e., the articular surface which is removed by the excision device 10). The contour of the load bearing surface 22 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates.

The load bearing surface 22 may be based on two or more curvatures, for example, the anterior-posterior (AP) curvature and the superior-inferior (SI) curvature. One or more of the AP and/or SI curvatures may themselves be based on multiple curves, (for example, as generally described in U.S. patent application Ser. No. 12/027,121, filed Feb. 6, 2008 and entitled SYSTEM AND METHOD FOR JOINT RESURFACE REPAIR, which is fully incorporated herein by reference). The load bearing surface 22 may be generally concaved. For example, the load bearing surface 22 may have a generally hemi-spherical shape.

The load bearing surface 22 may also include a beveled region 26 disposed about the perimeter of the load bearing surface 22. The beveled region 26 may reduce the potential of further damage to the surrounding articular surface by eliminating a hard transition between the load bearing surface 22 and the remaining articular surface. The beveled region 26 may be particularly helpful if a portion of the implant 12 is slightly proud with respect to the remaining articular surface.

The bone facing surface 24 may be configured to be generally received in the excision site created by the excision device 10. For example, the bone facing surface 24 may have a generally hemi-spherical shape substantially corresponding to the contour of the cutting surfaces 20 of the cutters 16*a*, 16*b*. The bone facing surface 24 may also include one or more lips, protrusions, ribs or the like 28*a*-28*n* configured to increase the mechanical connection between the implant 12 and the patient's bone within the excision site. Again, these lips or the like 28*a*-28*n* may generally correspond to the contours of the cutting surfaces 20 of the cutters 16*a*, 16*b*. The voids or space 30*a*-30*n* between the lips 28*a*-28*n* may create pockets for bone in-growth and/or bone cement.

Figure 4:
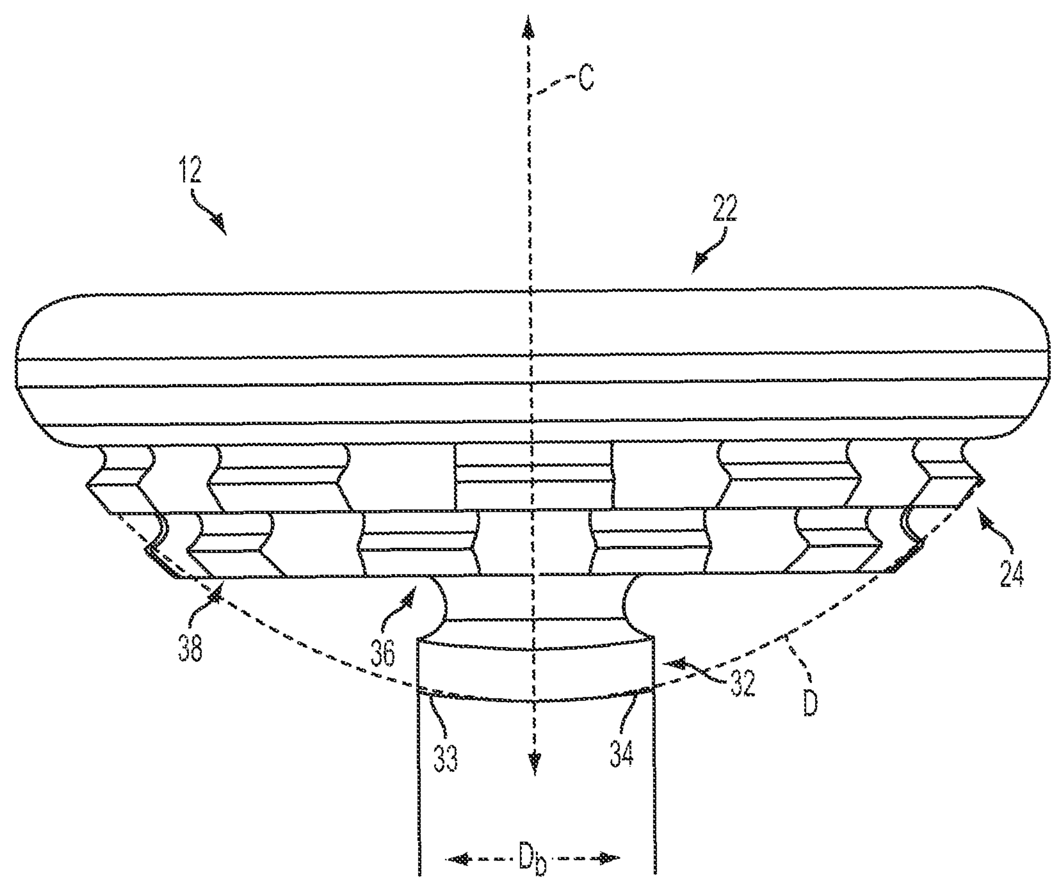
FIG. 4 illustrates a side view of an example of an implant.
Figure 5A:
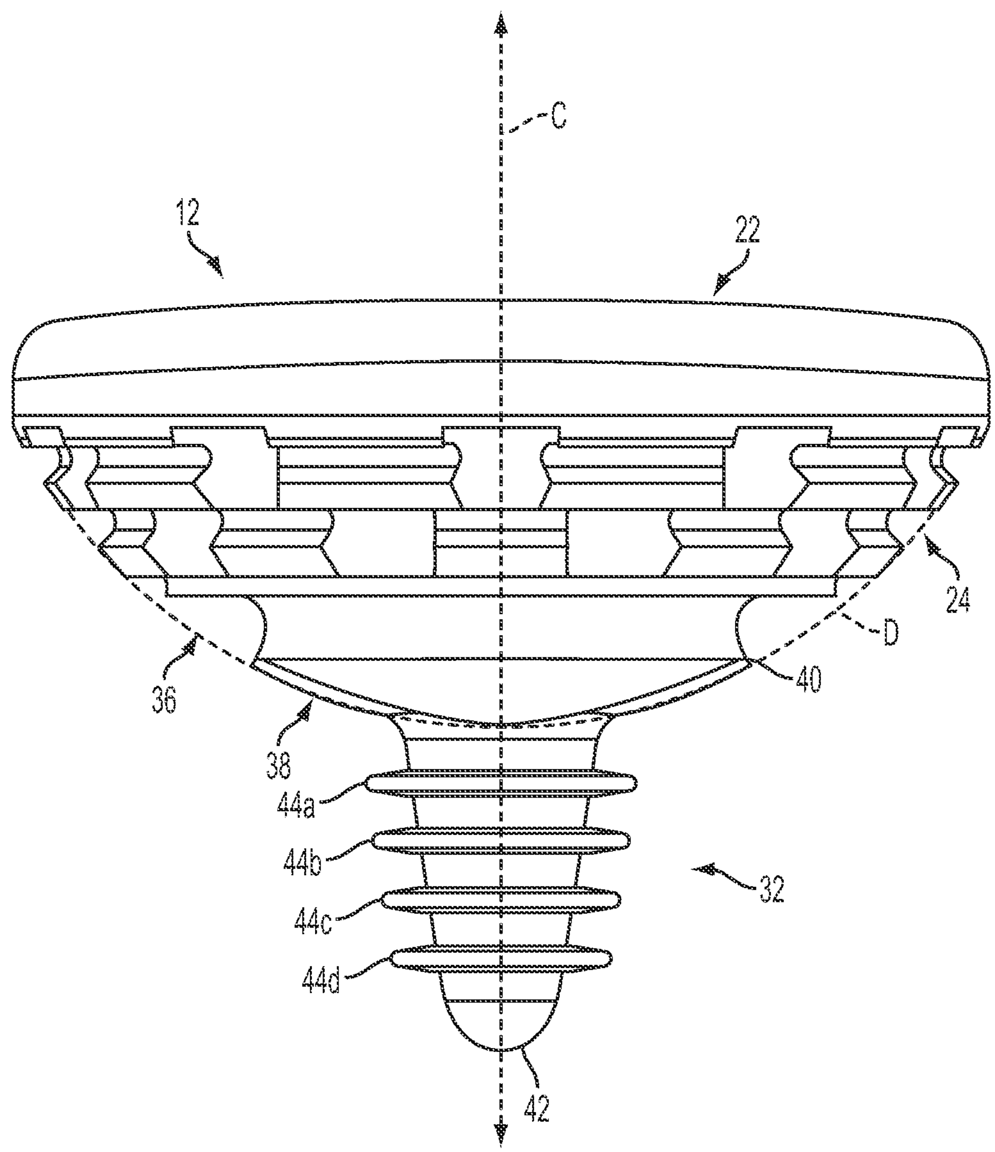
FIG. 5*a* illustrates a side view of another example of an implant.
Figure 5B:
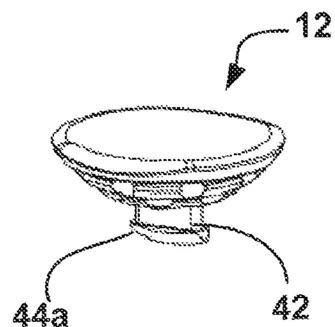
FIG. 5*b* illustrates a perspective view of an example of an implant.
Figure 5C:
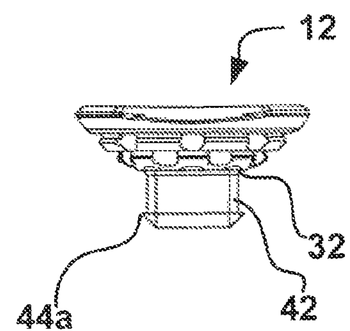
FIG. 5*c* illustrates a side view of an example of the implant of FIG. 5*b;*
Figure 5D:
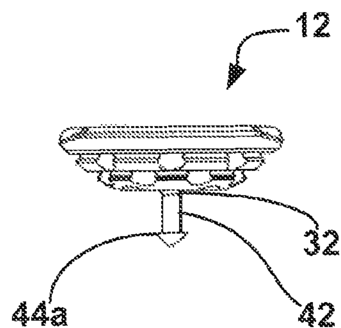
FIG. 5*d* illustrates another side view of an example of the implant of FIG. 5*b;*
Figure 5E:
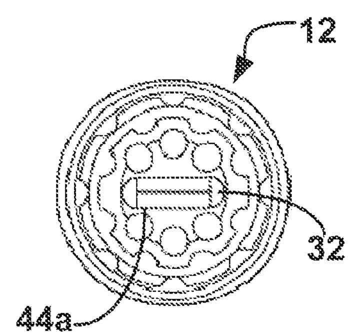
FIG. 5*e* illustrates a bottom view of an example of the implant FIG. 5*b;*
Figure 5F:
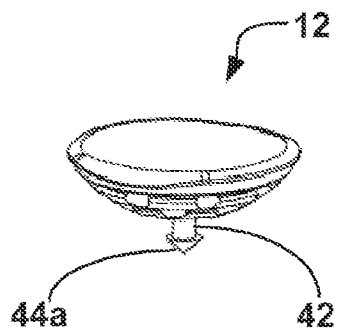
FIG. 5*f* illustrates a side perspective view of an example of the implant of FIG. 5*b;*

Turning now to FIGS. 4 and 5*a*, the implant 12 may optionally include at least one keel or tail 32 extending generally outwardly from the bone facing surface 24. For example, the implant 12 may include at least one keel 32 including a protrusion or button 34 disposed about a distal end of a base region 36 as generally illustrated in FIG. 4. For example, the implant 12 may include a single keel 32 extending generally downwardly and away from the bottom surface 38 of the bone facing surface 24 generally along the central axis C of the implant 12. The base region 36 may be coupled to the bottom surface 38 of the bone facing surface 24 and may have an hour-glass shape which may initially taper radially inwardly and then taper radially outwardly. The bottom surface 33 of the button 34 may have a curvature substantially corresponding to the curvature of the implant site. For example, the bottom surface of the button 34 may have a curvature (generally illustrated by dotted curve D) substantially corresponding to the curvature of the cutting surfaces 20.

The button 34 may extend generally radially outwardly from a distal end of the base region 36. As such, the button 34 may have a diameter $D_b$ greater than at least a portion of the base region 36, for example, the portion of the base region adjacent to the button 34. According to one embodiment, the diameter $D_b$ of the button 34 may be the same as or slightly larger than the diameter of the cavity in the excision site in which it is configured to be received. As such, the button 34 may form an interference fit with the cavity in the excision site which may secure the implant 12 to the bone and may also facilitate alignment of the implant 12 with respect to the articular surface and the excision site. Alternatively, the diameter $D_b$ of the button 34 may be slightly smaller than the diameter of the cavity in which it is configured to be received. As such, the button 34 may also facilitate alignment of the implant 12 with respect to the articular surface and the excision site. In addition, bone cement or the like may be disposed around the keel within the cavity to increase the mechanical connection between the keel 32 and the bone.

FIG. 5*a* illustrates another embodiment of a keel 32. The keel 32 may include a base region 36 extending generally outwardly/downwardly and away from the bottom surface 38 of the bone facing surface 24 generally along the central axis C of the implant 12. For example, the keel 32 may extend outwardly/downwardly and away from the bottom surface 38 of the bone facing surface 24 beyond the curvature D substantially corresponding to the curvature of the cutting surfaces 20. The keel 32 may be configured to be received in an additional cavity, pocket or the like formed within the excision site. The additional cavity may be formed subsequent to the formation of the excision site using an additional cutter, chisel, drill or the like (not shown).

The base region 36 may include one or more radial lips, grooves, protrusions or the like 40. The keel 32 may also include a protrusion 42 extending generally downwardly and away from the base portion 36 generally along the central axis C of the implant 12. The protrusion 42 may include one or more radial lips, grooves, protrusions or the like 44*a*-44*n*. As discussed herein, the keel 32 may be configured to engage a cavity or the like disposed within the excision site and may be configured align the implant 12 with respect to the articular surface and/or the excision site and may also increase the mechanical coupling of the implant 12 to the bone.

Figure 5G:
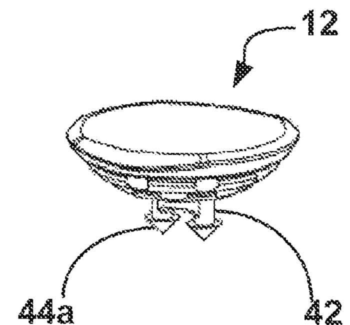
FIG. 5*g* illustrates a side perspective view of another example of an implant.

While the keels 32 illustrated in FIGS. 4 and 5*a* are shown having a generally concentric shape, the keel 32 may have other configurations. For example, in the embodiment illustrated in FIG. 5*b* through 5*f* the keel 32 and/or the protrusion 42 extending from the keel 32 may have a shape configured to prevent rotations of the implant 12 with respect to the articular surface. The keel 32 may have a non-circular shape configured to be received in the excision site in a lock-and-key configuration. By way of example, the keel 32 may have a generally multifaceted geometry (such as, but not limited to, rectangular, pentagonal, hexagonal or the like) configured to received in the excision site. Similarly, the protrusion 42 may exhibit a multifaceted geometry such as generally oblong or rectangular, pentagonal, hexagonal, or the like. The protrusion 42 may also exhibit an additional (or second) protrusion 44*a* extending outwardly in a radial direction from the central axis of the implant 12, which may form a raised edge or surface around the perimeter of the protrusion 42. As illustrated, protrusion 42 may end in a relatively pointed tip, or may exhibit a curvature as illustrated in FIG. 5*a*. FIG. 5*g* illustrates a further embodiment of protrusion 42, wherein the protrusion 42 may be formed from a variety of features, such as circular, rectangular, etc. It may be appreciated that, the implant 12 and the keel 32 may be a single, integral or unitary component or may be formed from two or more pieces which may be secured to each other (either permanently or removably secured).

Turning now to FIGS. 6-10, one method of installing an implant 12 consistent with the present disclosure is generally illustrated. One or more incisions 49 may be created proximate the patient's shoulder 50 to provide access to the defect 52 on the patient's articular surface 54, for example, using a scalpel or the like. The incision 49 may be made through the anterior portion of the patient. Again, the present disclosure will describe a system and method for replacing a portion of the articular surface of the glenoid; however, it should be understood that the system and method according to the present disclosure may also be used to resurface articular surfaces other than the glenoid. The system and method consistent with one embodiment of the present disclosure may allow for "key-hole" surgery in which a minimum number and size of incisions are made. As may be appreciated, "key-hole" surgery may reduce the amount of pain and/or discomfort experienced by the patient and may reduce healing times.

Figure 6:
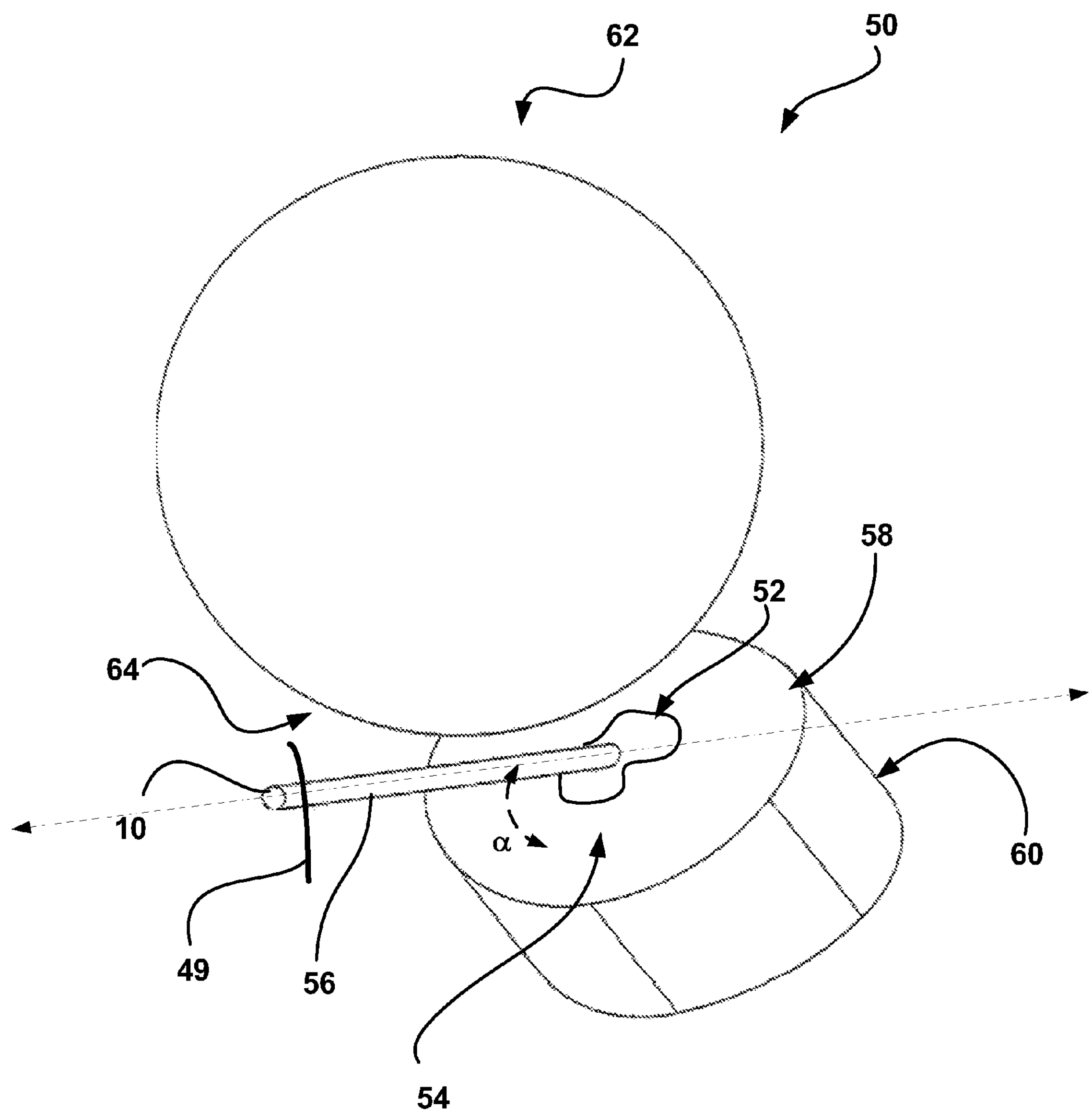
FIG. 6 illustrates an example of a guide pin positioned in the glenoid surface of a scapula.

Once the incision is created, a guide pin 56, FIG. 6, may be positioned about the glenoid 58 on the scapula 60 to provide an access passageway to the glenoidal articular surface 54 as will be described herein. Consistent with one embodiment, the guide pin 56 may comprise threaded and/or self-tapping tip (not shown) configured to be secured to the patient's bone. The guide pin 56 may be secured to the bone using a drill or the like (not shown) and at least a portion of which may be disposed proximate to and/or within the defect site 52 on the articular surface 54. Optionally, a drill guide (not shown) may be used to facilitate alignment of the guide pin 56 with respect to the articular surface 54.

The guide pin 56 may be disposed at an angle $\alpha$ relative to the articular surface 54. Angle $\alpha$ may be less than or equal to 90 degrees, wherein $\alpha \leq 90$ degrees with respect to the articular surface 54. In some examples, angle $\alpha$ may be less or equal to 90 degrees and greater than or equal to 45 degrees with respect to the articular surface 54, wherein 45 degrees$\leq \alpha \leq$90 degrees with respect to the articular surface 54. In further examples, 90 degrees>α>45 degrees and/or 90 degrees>α≥45 degrees, with respect to the articular surface 54. The degree of the angle α may depend on the location and/or size of the defect 52 and may be selected to avoid contact with the humerus 62. In some circumstances, the degree of the angle α may also be selected to avoid contact with the perimeter of the articular surface 54.

Figure 7:
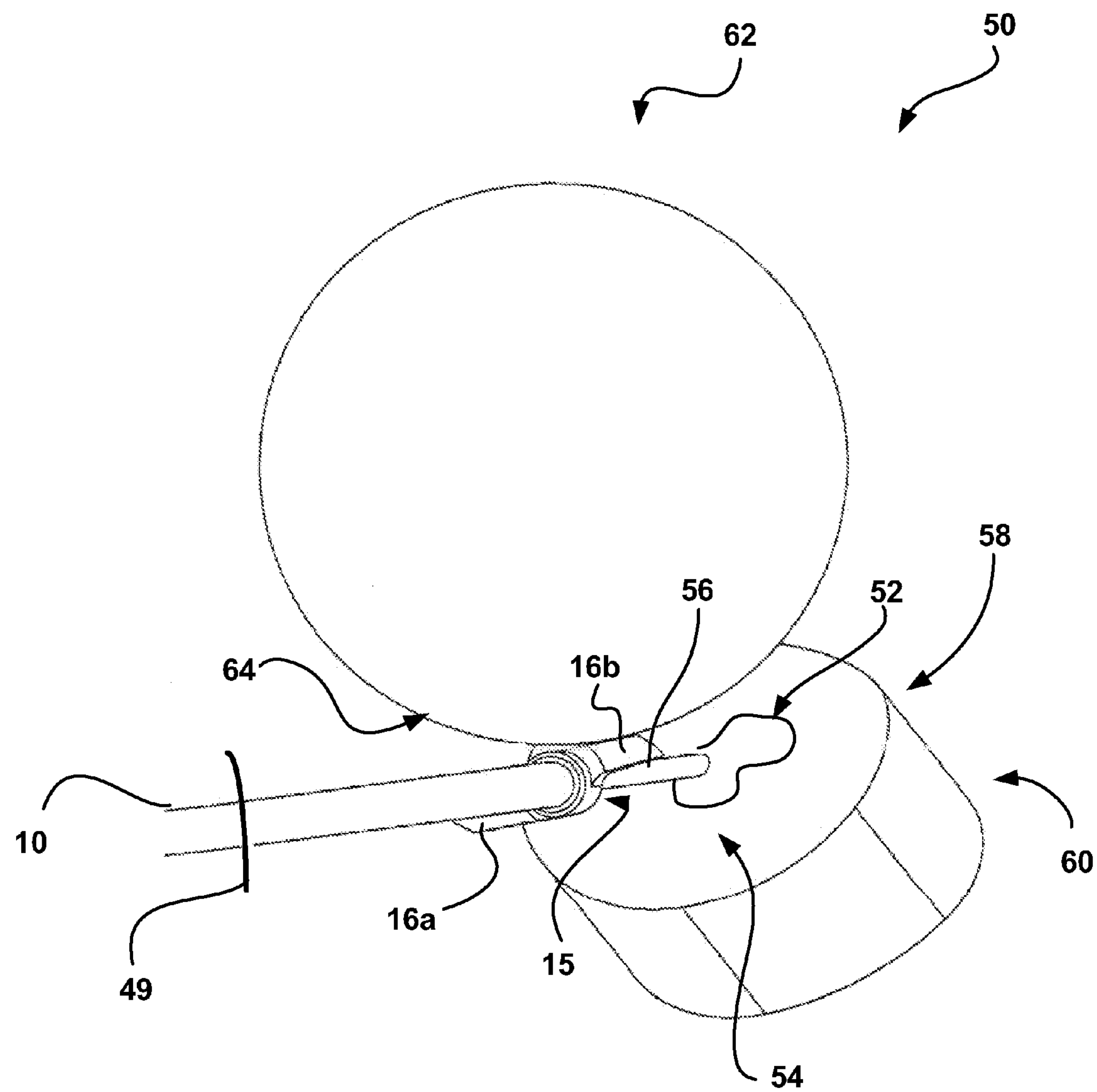
FIG. 7 illustrates an example of an excision device including a cannulated shaft and a cutter positioned at the distal end of the cannulated shaft passing over the guide pin positioned in the glenoid surface of a scapula.
Figure 8:
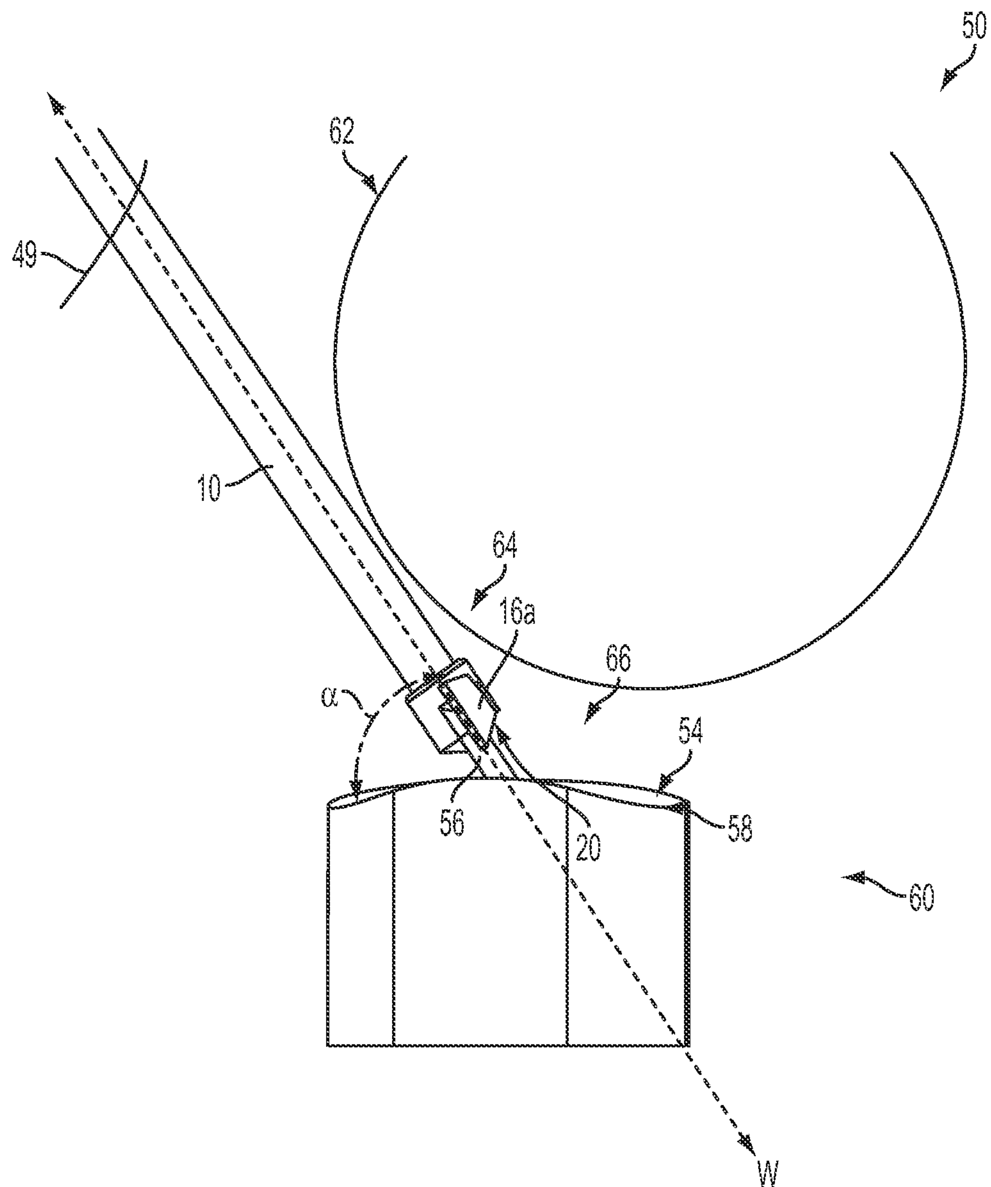
FIG. 8 illustrates a side view of an example of an excision device including a cannulated shaft and a cutter positioned at the distal end of the cannulated shaft passing over the guide pin positioned in the glenoid surface of a scapula.

Once the guide pin 56 is secured to the articular surface 54, the excision device 10 may be advanced over the guide pin 56 as generally illustrated in FIG. 7. For example, the guide pin 56 may be received within the passageway 15 defined by the cannulated shaft 14. According to at least one embodiment, the cutters 16*a*, 16*b* may be generally aligned in a single plane extending along the longitudinal axis of the excision device 10. The plane of the cutters 16*a*, 16*b* may be orientated generally tangential to the articular surface 64 of the humerus 62 such that the cutters 16*a*, 16*b* may slide by the articular surface 64 of the humerus 62 and between the humerus 62 and the scapula 60 as generally illustrated in FIGS. 7 and 8.

Once the cutters 16*a*, 16*b* are advanced over the guide pin 56 to the articular surface 54, the excision device 10 may be rotated about the guide pin 56. As may be best seen in FIG. 8, a pocket of cavity 66 may be present between the articular surface 54 of the glenoid 58 and the articular surface 64 of the humerus 62. The cutters 16*a*, 16*b* of the excision device 10 may therefore rotate about the guide pin 56 without contacting the articular surface 64 of the humerus 62. The cutters 16*a*, 16*b* may have generally flat cutting surfaces 20, forming a point along the length thereof, or may have serrated cutting surfaces.

Figure 9:
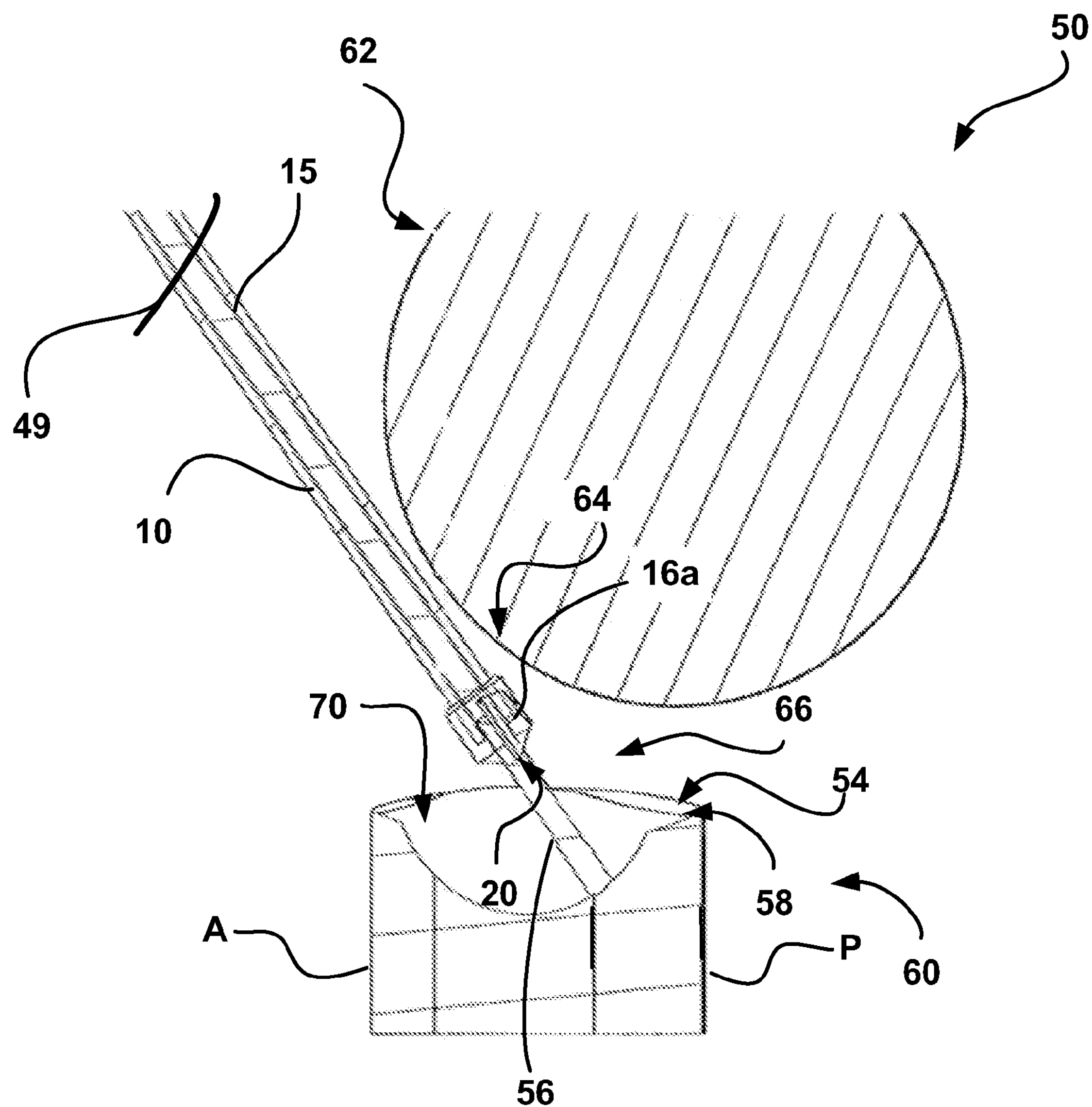
FIG. 9 illustrates a side-cross sectional view of an excision device including a cannulated shaft and a cutter positioned at the distal end of the cannulated shaft passing over the guide pin positioned in the glenoid surface of a scapula.

The excision device 10 may thus be rotated about the guide pin 56 to form an excision site 70 within the articular surface 54 of the glenoid 60 as generally illustrated in FIG. 9. Due to the contour of the cutting surfaces 20 of the cutters 16*a*, 16*b*, the excision site 70 created by the excision device 10 may have a generally hemi-spherical configuration regardless of the angle α of the guide pin 56.

Figure 10:
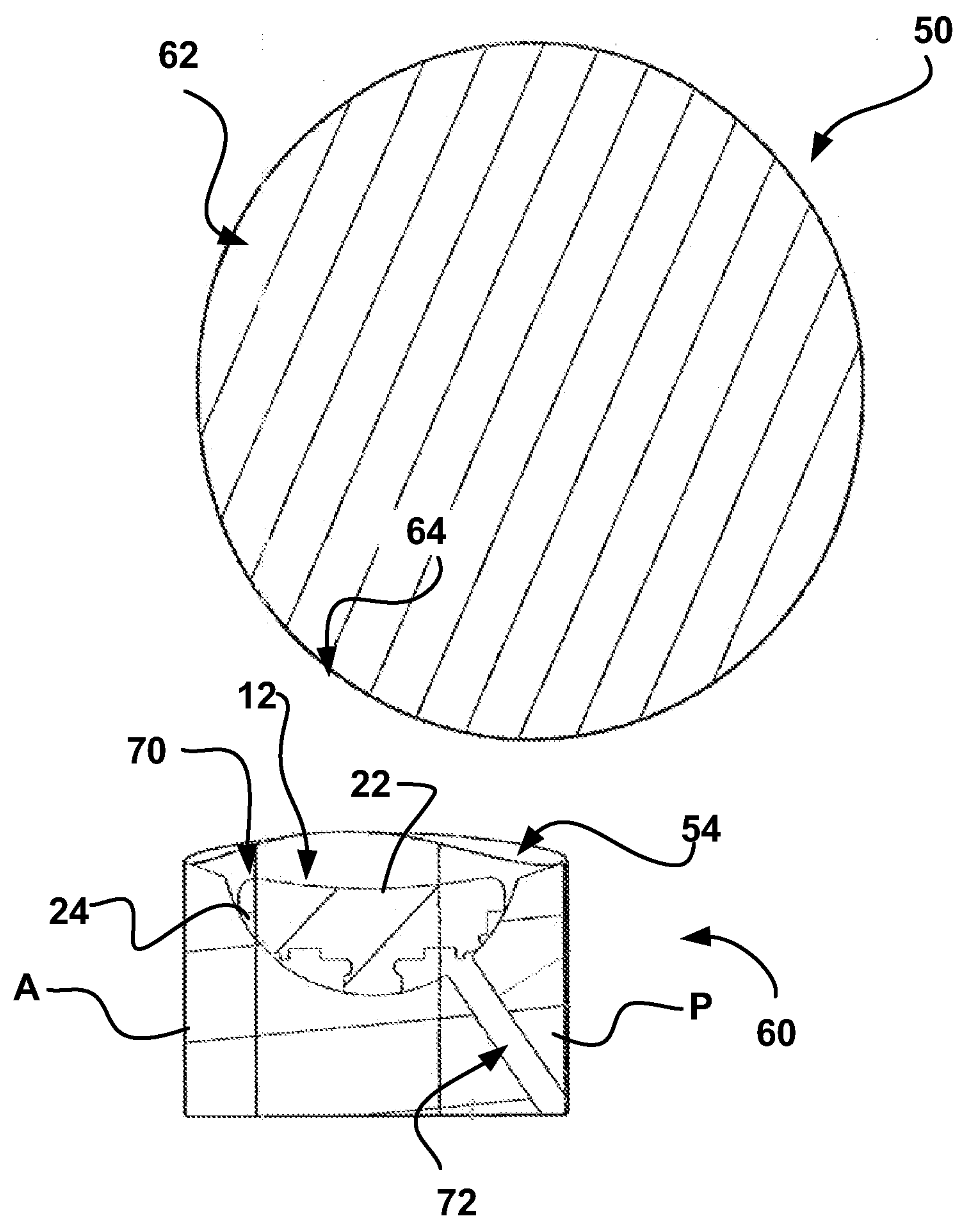
FIG. 10 illustrates a side-cross sectional view of an excision site including an implant.

Once the excision site 70 is formed within the articular surface 54, the excision device 10 and the guide pin 56 may be removed as generally illustrated in FIG. 10. The removal of the guide pin 56 may leave a cavity 72 formed by the distal tip of the guide pin 56. The implant 12 may then be received in the excision site 70. The spherical configuration of the excision site 70 may normalize the implant 12 with respect to the remaining articular surface 54. The load bearing surface 22 of the implant 12 may substantially match the original contour of the patient's articular surface 54 which was removed.

Figure 11:
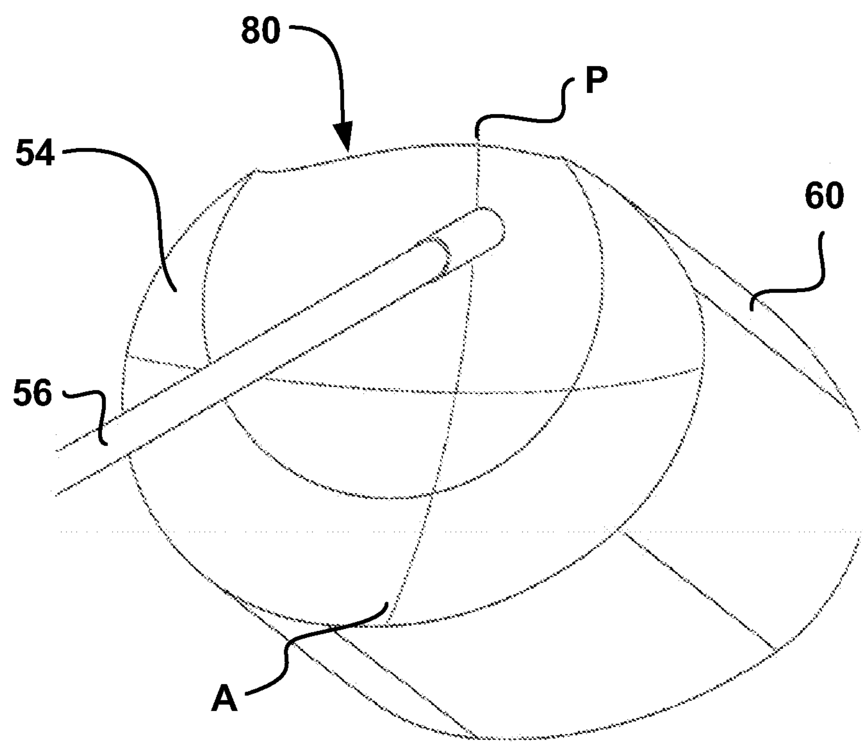
FIG. 11 illustrates an example wherein a portion of the perimeter of the articular surface is damaged and the guide pin is positioned such that a repair may be made at or near the perimeter of the articular surface.

As illustrated in FIG. 11, the system and method according to the present disclosure may also repair a defect 80 on the articular surface 54 in which a portion of the perimeter of the articular surface 54 is damaged or missing. For example, the posterior portion P of the articular surface 54 may have a defect 80 wherein a portion of the perimeter of the articular surface 54 is missing which may be caused by advanced chronic shoulder dislocation and/or early onset arthritis. To repair a defect 80 proximate the perimeter of the articular surface 54, the guide pin 56 may be moved further towards the posterior end P of the articular surface 54. The exact location of the guide pin 56 with respect to the articular surface 54 may depend on the location and size of the defect 80 as well as the size of the cutters 16*a*, 16*b* of the excision device 10.

Figure 12:
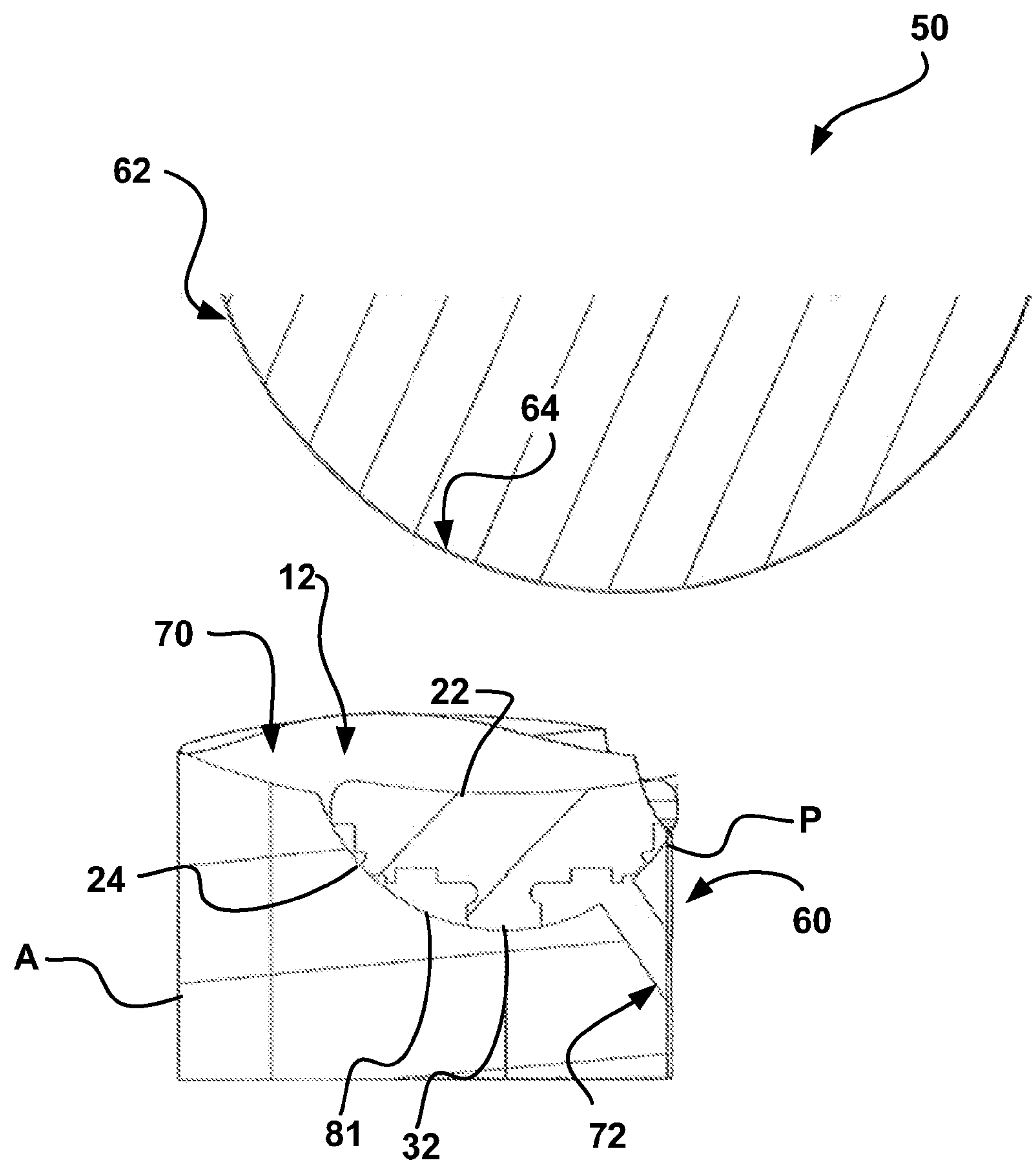
FIG. 12 illustrates a side-cross sectional view of an excision site including an example of an implant positioned at or near the perimeter of the articular surface.

According to one embodiment, the guide pin 56 may be located a distance away from the perimeter of the articular surface 54 which generally corresponds to the radius $R_e$ of the cutters 16*a*, 16*b*. The excision device 10 may be advanced over the guide pin 56 and rotated as described herein. Accordingly, the cutters 16*a*, 16*b* may remove a portion of the articular surface 54 to form an excision site 81 disposed about the perimeter of the articular surface 54 as generally illustrated in FIG. 12. The excision device 10 and the guide pin 56 may then be removed and the implant 12 may be received within the excision site 81. As may be seen in FIG. 12, a portion of the implant 12 may replace the perimeter of the articular surface 54 which was damaged and/or missing.

Figure 13:
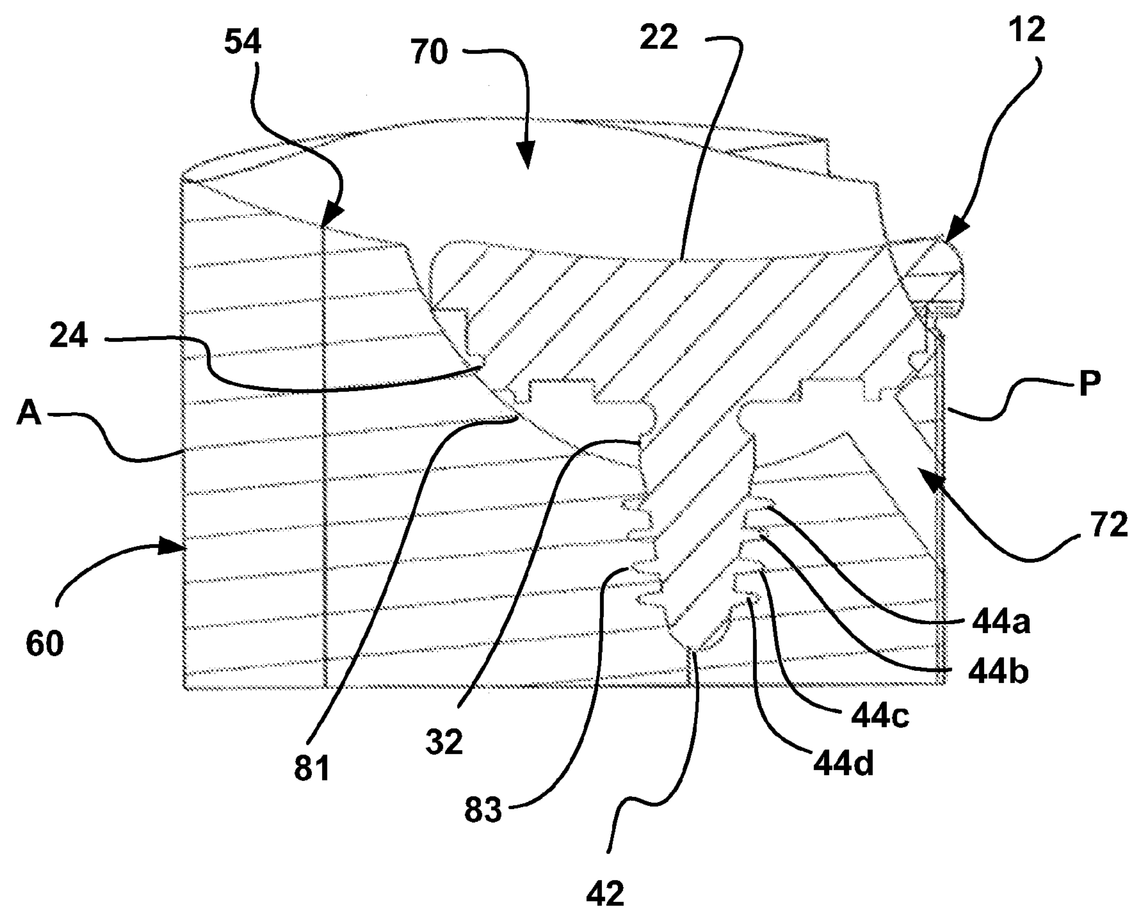
FIG. 13 illustrates an example of a side-cross sectional view of an example of an excision site including an example of an implant positioned at or near the perimeter of the articular surface.

The implant 12 may also include a keel 32 as generally illustrated in FIGS. 12 and 13. The keel 32 may facilitate alignment of the implant 12 with respect to the articular surface 54 and/or may provide an increased mechanical connection between the implant 12 and the bone. As discussed herein, the excision site 81 may also include one or more cavities 83, FIG. 13, configured to received at least a portion of the keel 32 (for example, but not limited to, one or more radial lips 44*a*-44*n* of the protrusion 42.

Once the position/orientation of the implant 12 has been confirmed (i.e., the contour of the load bearing surface 22 has been confirmed along the AP and/or SI planes to generally correspond to the original contour of the articular surface), the implant 12 may be secured to the bone. The implant 12 may be held in place by the lips, protrusions, ribs or the like 28*a*-28*n* of the bone facing surface 24, the keel 32, and/or bone cement or the like.

Turning to FIGS. 14-21, one system and/or method for locating an implant 12 consistent with the present disclosure is generally illustrated. The description of the system and methods herein are not limited to the treatment of any single articular surface of the glenoid and may apply not only to the one or more articular surfaces that may be present in the glenoid but to other articular surfaces through out the body as well.

Figure 14A:
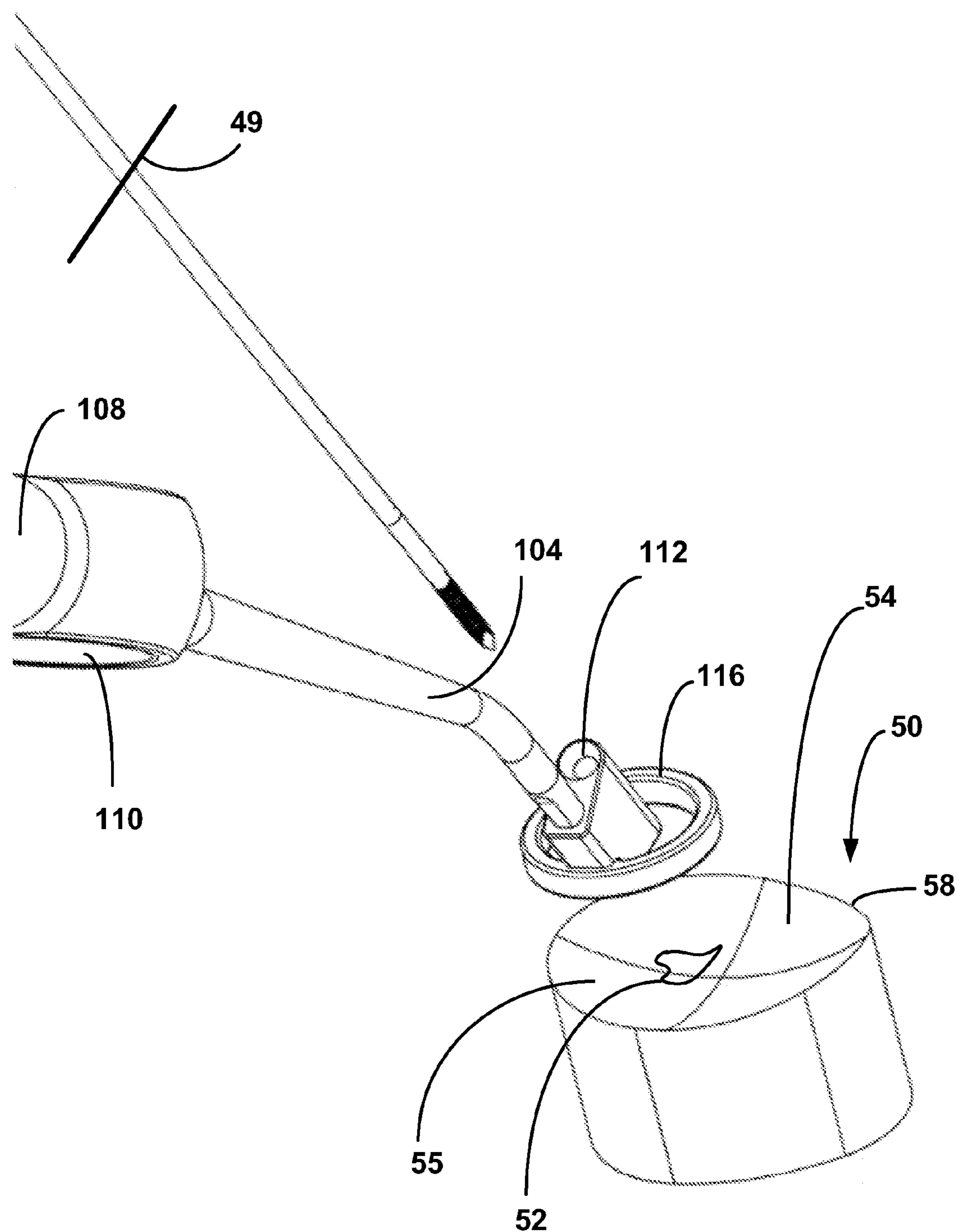
FIG. 14 illustrates an example of perspective view of an example of an excision guide and guide pin relative to an articular surface of a glenoid.
FIG. 14*b* illustrates an cross-sectional view of the side view of an example of an excision guide having a guide pin positioned therethrough, wherein at least a portion of the guide pin is disposed in an articular surface.
FIG. 14*c* illustrates a cross-section view of a side view of an embodiment of an excision guide.

One or more incisions 49 may be created proximate to the patient's shoulder 50 to provide access to the defect on the patient's articular surface 54, using, for example, a scalpel or the like. As may be appreciated, the glenoid may include one or more articular surfaces 54. Each of the articular surfaces may define a concavity as illustrated in FIG. 14.

Figure 14B:
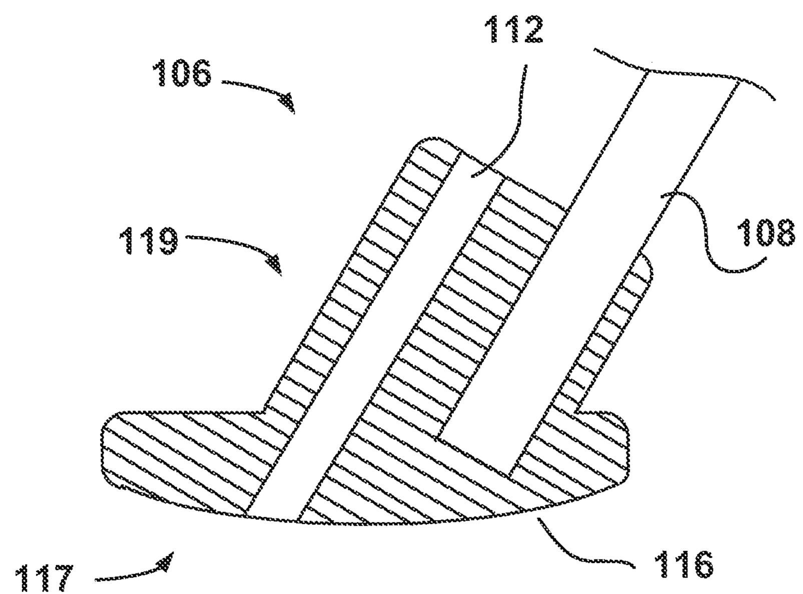
Figure 14C:
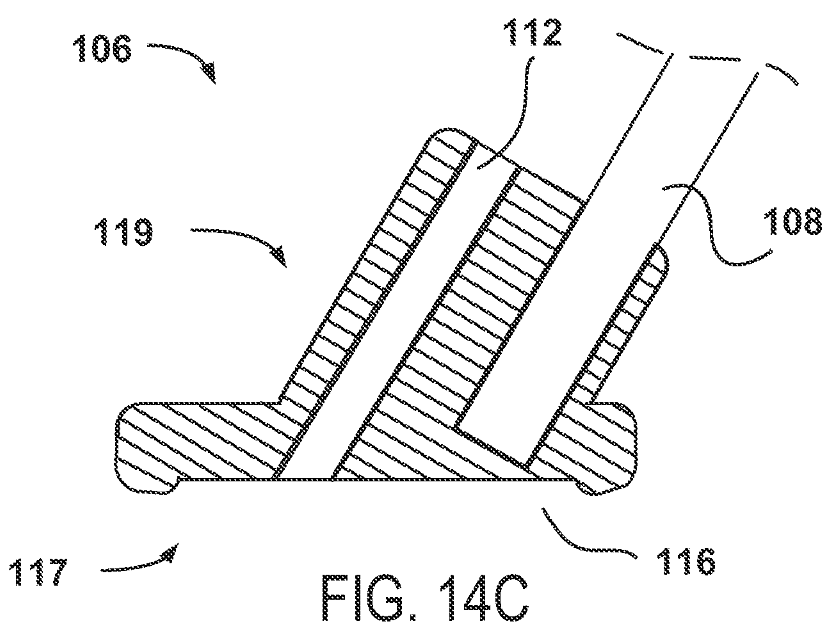

A portion of an excision guide 102 may be positioned within the incision and located between the humerus 62 and the articular surface 54 of the glenoid 58. The excision guide may include an arm 104 and a head 106, which may, in some embodiments, be inserted through the incision in such a manner to avoid contact with the humerus 62. FIGS. 14*b* and *c* illustrate embodiments of the excision guide head 106 and, in particular, variations in the contact surfaces 116 of the excision guide head 106 located on the lower portion 117 of the excision guide head 106. For example, in one embodiment, illustrated in FIG. 14*b*, the contact surface 116 may generally conform to the articular surface 54. In another embodiment, illustrated in FIG. 14*c*, the contact surface 116 may be a ring near the periphery of the lower portion 117 of the excision guide head 106. As may be appreciated in some embodiments, when in the shape of a ring, the contact surface may be continuous or may, in other embodiments, be discontinuous forming ridges around the contact surface 116. The excision guide 102 may also include a handle 108, which may or may not include one or more indentations 110 to assist in manipulation and/or stabilization of the excision guide 102. The handle may be affixed to the upper portion of the excision guide head 119.

The head 106 of the excision guide 102 may be located over a defect 52 of an articular surface 54. The head 106 may locate the excision guide 102 relative to the articular surface 54. In some embodiments, the head 106 may be generally centered on the articular surface 54 including the defect 52. For example, in one embodiment, the head 106 may be located generally centered in the concavity 55 of the articular surface 54. Once the head 106 is positioned over the defect 52, the guide pin 56 may be received into and pass through a guide sleeve 112 disposed on the head 106. As illustrated in FIGS. 14*b* and *c*, the guide sleeve 112 may define an opening from the upper surface 119 of the excision guide head 106 through the lower surface 117 of the excision guide head 106. The guide sleeve 112 may position the guide pin 56 relative to the defect 52 on the articular surface. In addition, the guide sleeve 112 may be formed in and/or integral to the head 106 or may be formed in an insert connected to the head 106.

Figure 15:
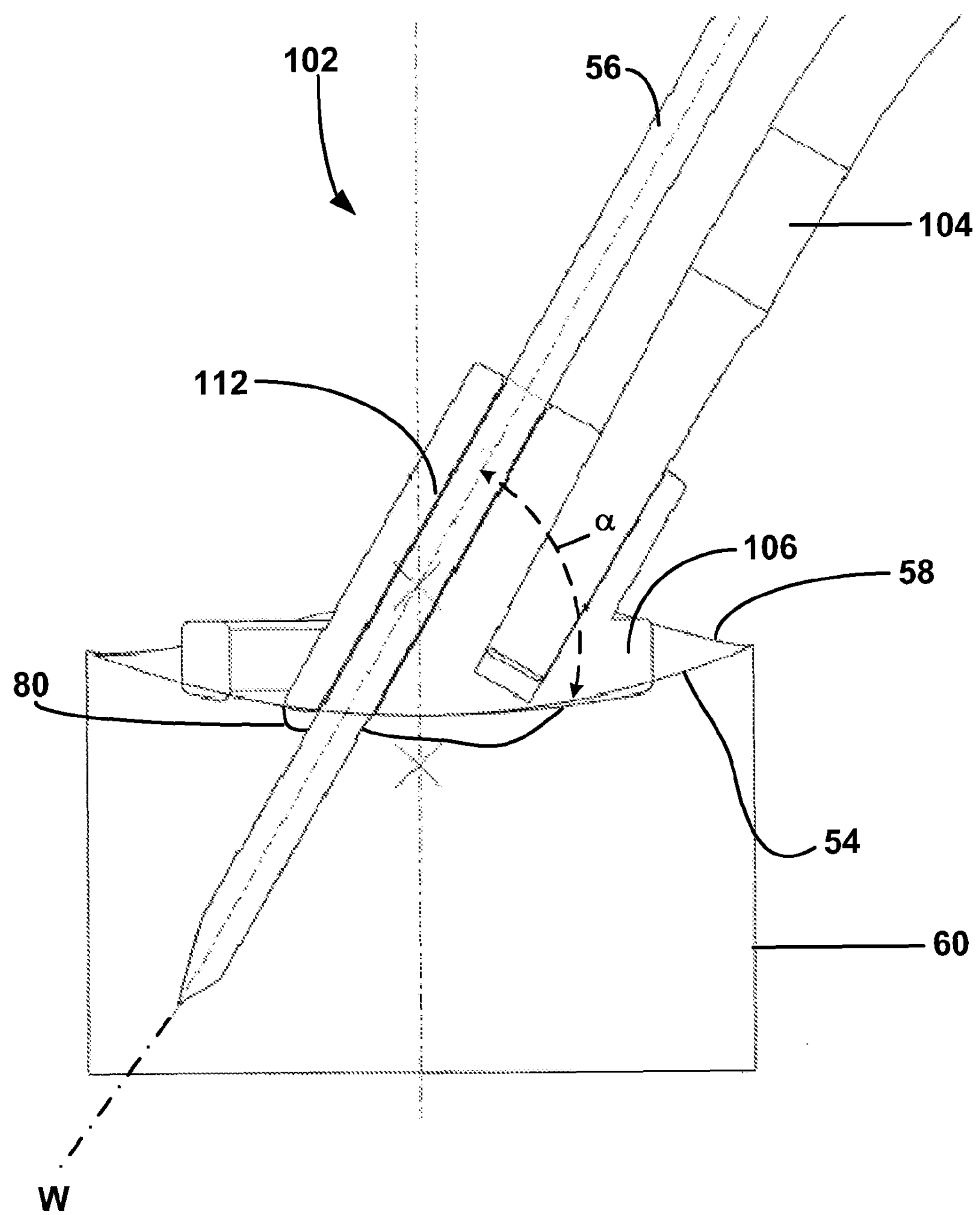
FIG. 15 illustrates a cross-sectional view of a side view of another

As illustrated in FIG. 15, the excision guide 102 may orient the working axis (W) of the guide pin 56 in one or more planes. For example, in one aspect, the guide sleeve 112 may angle the guide pin 56, such that the guide pin may be positioned at an angle α that may be 90 degrees or less from the articular surface, including all values and increments in the range of 10 degrees to 90 degrees, such as in one embodiment 45 degrees to 75 degrees or in a further embodiment 60 degrees from the articular surface 54.

Figure 16:
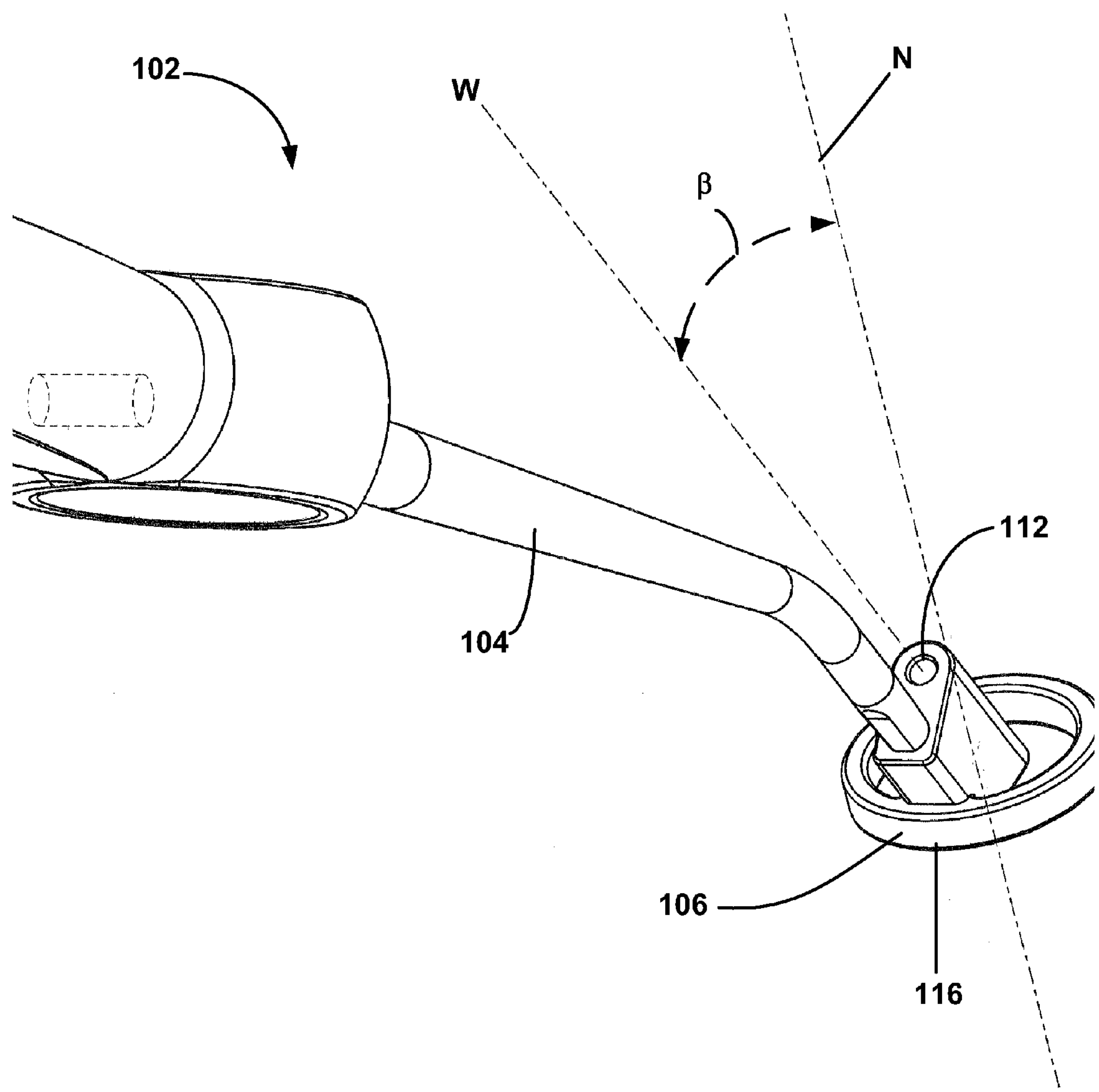
FIG. 16 illustrates a cross-sectional side view of an example of a excision device including at least one cutter portioned over a guide pin and relative to the excision guide.

In another aspect, the guide sleeve 112 of the excision guide 102 may orient the working axis (W) of the guide pin 56 at an angle β relative to a normal axis (N). The normal axis (N) may, in some embodiments, be generally normal and central to a defect 80 in the articular surface 54. Angle β may be 90 degrees or less and in some examples, including all values and increments in the range of 5 degrees and 80 degrees, such as in the range of 10 degrees to 30 degrees. FIG. 16 illustrates another example of the working axis (W) defined by the guide sleeve 112 to an axis (N) generally central and normal to the lowest point of the contact surface 116 of the excision guide head 106, which may correspond to the axis generally normal and centrally located to defect 80 or to the deepest point of the excision site 70.

Figure 17:
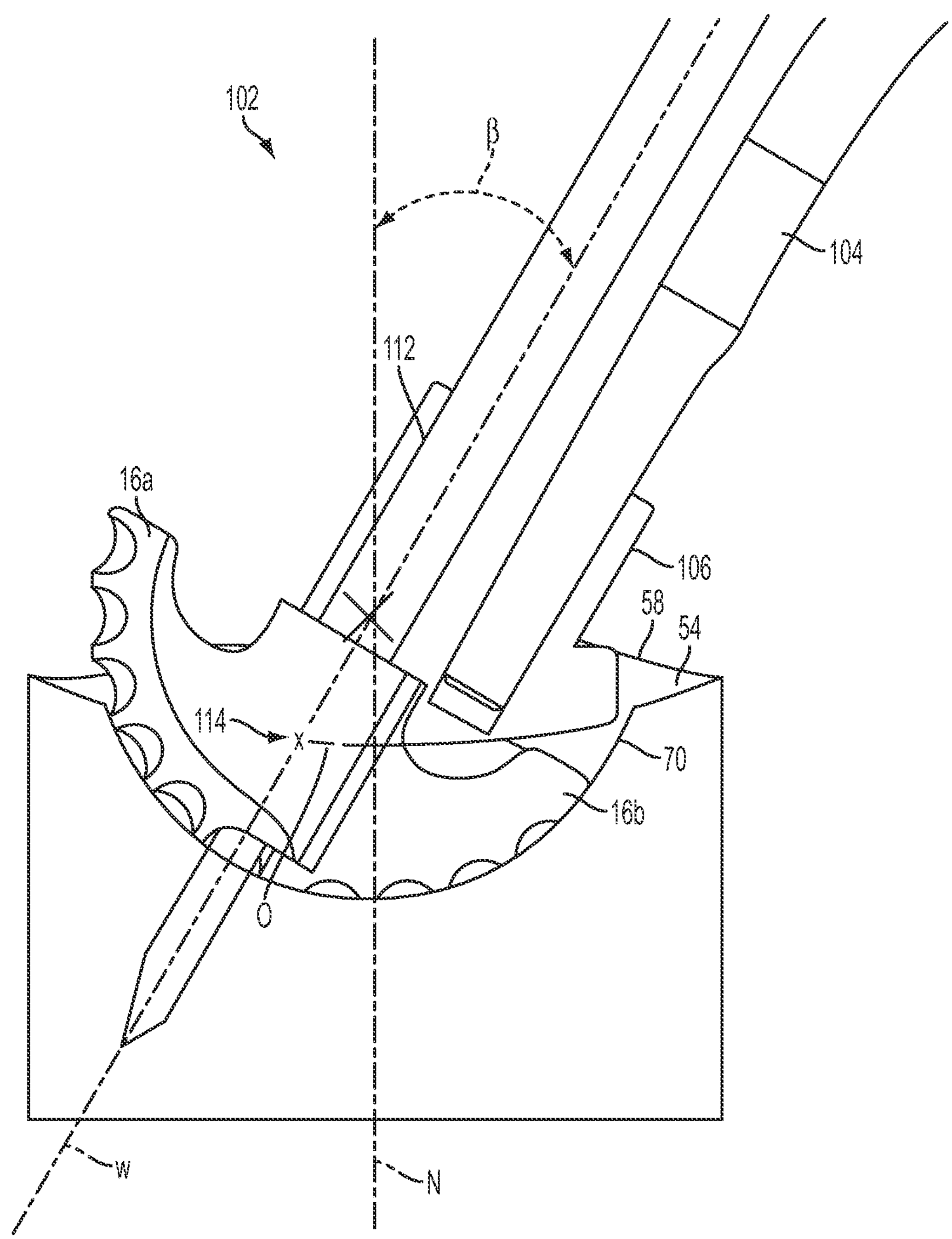
FIG. 17 illustrates a perspective view of an example of an excision guide.

The guide sleeve 112 may also offset the intended entry point 114 of the guide pin 56 in the articular surface 54 radially outward from the axis (N) normal and generally central to the excision site and/or the articular surface 54. FIG. 17 illustrates an embodiment of the positioning of the at least one cutter 16*a*, 16*b* relative to the positioning of the excision guide 102. In one embodiment, the offset (O) may be determined based on the angle of entry of the guide pin 56 (α or β) into the articular surface 54 and/or the depth of the desired excision site, or the height of the desired implant. For example, the offset (O) may be proportional to the angle α of the guide pin 56 to the articular surface 54 or angle β of the guide pin 56 to the normal axis (N).

The working axis (W) may be positioned at an angle β in the range of 10 degrees to 90 degrees, such as in one embodiment, 15 degrees to 45 degrees, or in a further embodiment 60 degrees from the normal axis (N). As may be appreciated, in some embodiments, the surface of the excision guide head 116 may exhibit some degree of curvature and may be convex. The curvature of the surface of the excision guide head 116 may be configured to generally match the curvature of at least a portion of the articular surface 54. In some embodiments, it may be appreciated, that the curvature of the articular surface 54 and the surface of the excision guide head may not match exactly but may provide a "close fit" sufficient to locate the excision guide head 106 within the glenoid 58. In some non-limiting embodiments, the curvature of the excision guide head surface 116 may be generally hemispherical, including pyriform or teardrop in shape.

Figure 18:
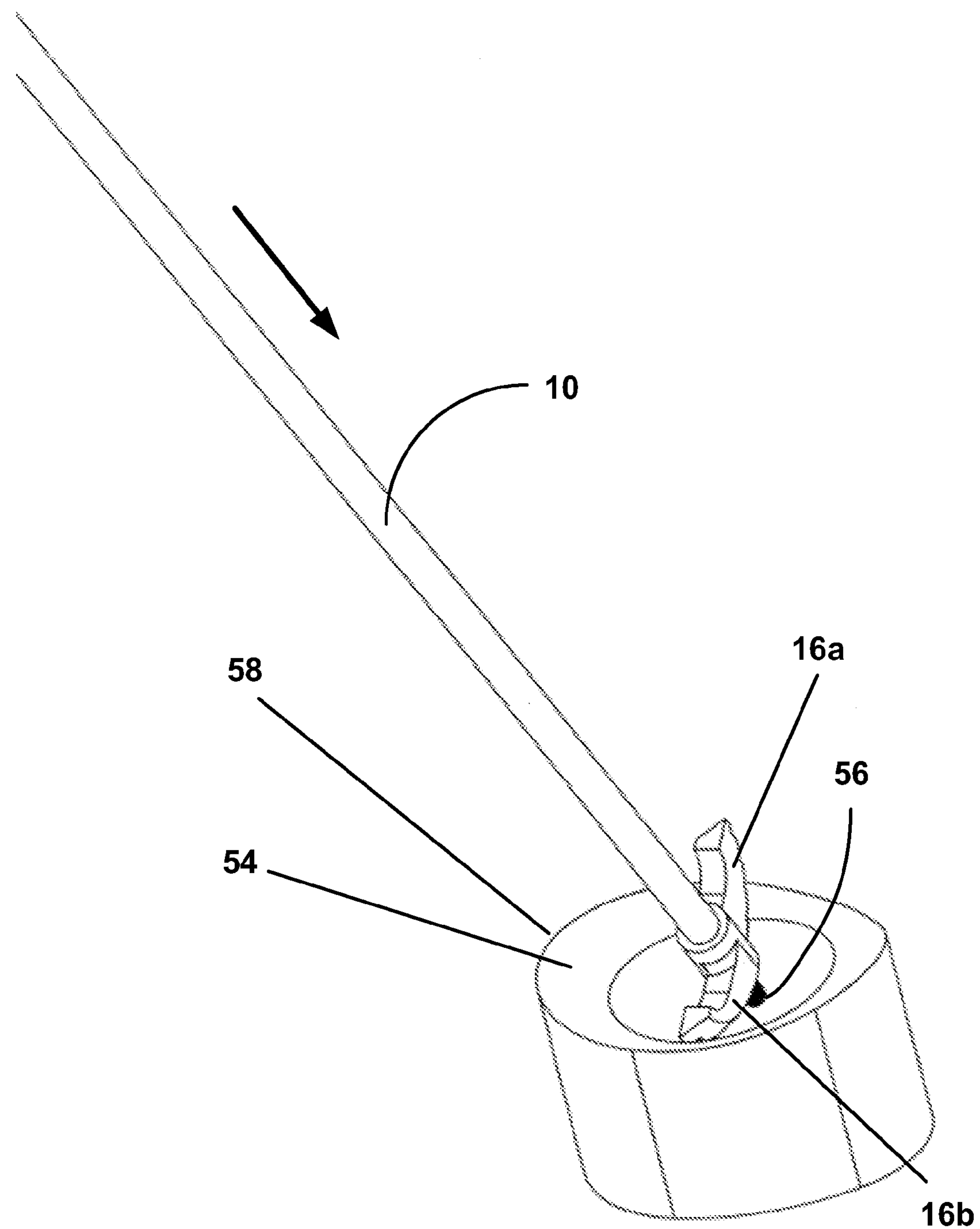
FIG. 18 illustrates a perspective view of an example of an excision device advance over a guide pin.

Once the guide pin 56 is positioned in the articular surface 54 of the glenoid 58, as illustrated in FIG. 15, the excision guide 102 may be removed from the glenoid 58 by sliding the excision guide 102 up the guide pin 56 away from the glenoid 58. As illustrated in FIG. 18, the excision device 10, including one or more cutters 16*a* and 16*b*, may be slid (in direction of arrow) over the guide pin 56 and, as described above, the excision device 10 may be rotated forming an excision site 70 in the articular surface 54.

Figure 19A:
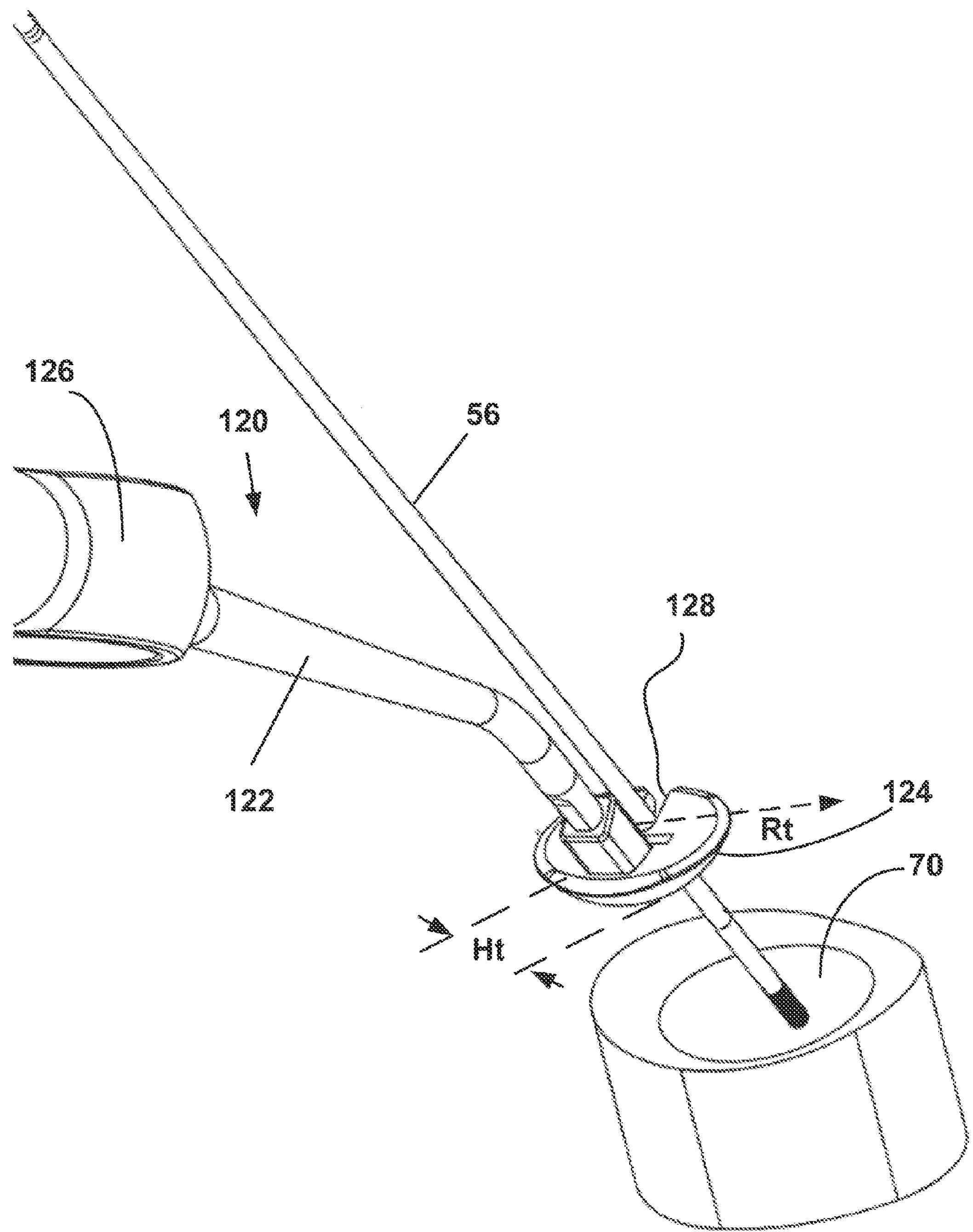
FIG. 19 illustrates a perspective view of an example of an impact guide received by a guide pin.
Figure 19B:
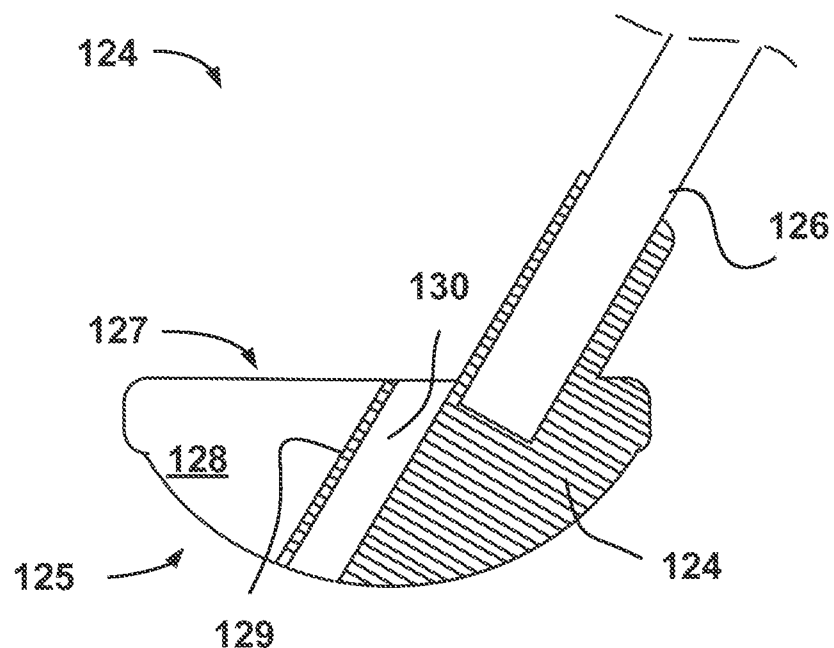
Figure 19C:
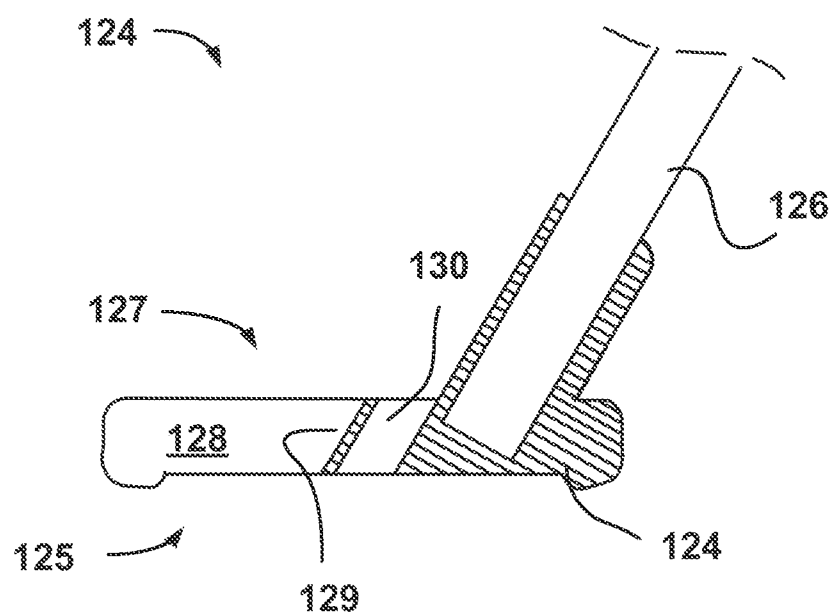

The excision device 10 may then be removed from the guide pin 56 and an impact guide 120 may be inserted through the incision 49 and over the guide pin 56, an embodiment of which is illustrated in FIGS. 19*a* through 19*c*. The impact guide 120 may include an impact guide arm 122, an impact guide head 124 and an impact guide handle 126. In one embodiment, the impact guide 120 may be the same as the excision guide 102, wherein the head 106 of the excision guide 102 may be interchangeable with the one or more impact guide heads 124. In another embodiment, the impact guide 120 may be separately provided from the excision guide 102.

As may be appreciated, the impact guide heads 124 may generally correspond to or mimic the size and shape of an implant, described above. An embodiment of an impact guide head is illustrated in FIG. 19*b*, wherein the impact guide head 124 may include a lower portion 125 that substantially conforms to the generally hemispherical excision site. The impact guide head may exhibit a given height $H_t$ and radius $R_t$ matching that of an implant to be provided in the excision site 70 (see FIG. 19*a*). In another embodiment, illustrated in FIG. 19*c*, the impact guide may include a lower portion 127 that includes a ring or bevel around the periphery that may conform to the excision site. The remainder of the lower portion 125 may be recessed.

The impact guide head 124 may include a guide notch 128, which may be inserted over the guide pin 56 or around the guide pin 56 (as illustrated in FIG. 19*a*). It may be appreciated that while a notch is illustrated defining an opening in the periphery of the impact guide head 124, i.e., extending to the periphery of the impact guide head 124, the guide notch 128 may also include a sleeve defined in the impact guide head 124. As illustrated in FIGS. 19*b* and 19*c*, the guide notch 128 may generally define an opening from the upper portion 127 through the lower portion 125 of the impact guide head 124. In addition, the guide notch 128 may include at least one surface 129 that may accommodate the angle and offset of the guide pin 56 relative to the articular surface 54, such that the impact guide head 124 may be positioned generally central within the excision site 70 and the guide pin 56 may rest on the surface 129.

Upon placement of the impact guide head 124 by the impact guide 120 into the excision site 70, a determination may be made as to whether the excision site 70 is sufficiently deep enough to accommodate the implant that may eventually be placed within the excision 70. As may be appreciated, if the excision site 70 is not sufficient deep, or properly formed, the impact guide 120 may be removed from the excision site 70 and the guide pin 56. The excision device 10 may again be placed over the guide pin 56 and further excision may be provided to deepen or further form the excision site 70. This procedure of checking the excision site 70 using the impact guide head 124 may be repeated until it is determined that an implant will fit within the excision site 70. In some embodiments, the use of the impact guide 120 may be to prevent the implant from being too proud in the excision site and from rising above the articular surface 54. In other embodiments, the impact guide head 124 and/or the impact guide 120, may be interchanged with one or more impact guide heads and/or impact guides to determine which implant may better fit or accommodate the excision site in terms of the implant radius or height. Accordingly, one or more impact guide heads 124 may be provided. In some embodiments, the impact guide heads 124 may be interchangeable and removable from the impact guide 120. In other embodiments, a number of impact guides 120 may be provided including different sized impact guide heads 124 fixed to the impact guide 120.

Figure 20:
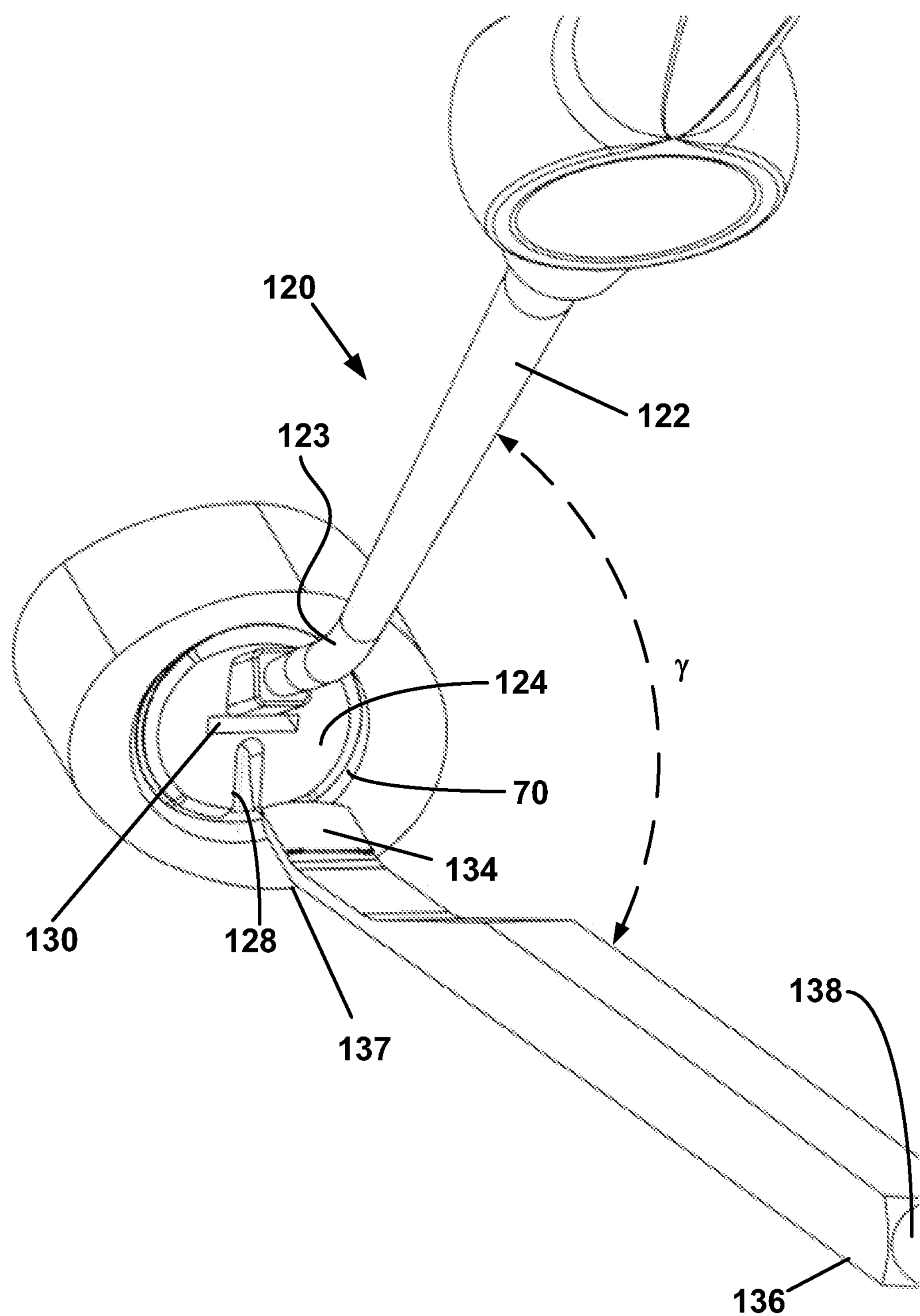
FIG. 20 illustrates a perspective view of an example of an impact guide positioned in an excision site and an impact device.
Figure 21:
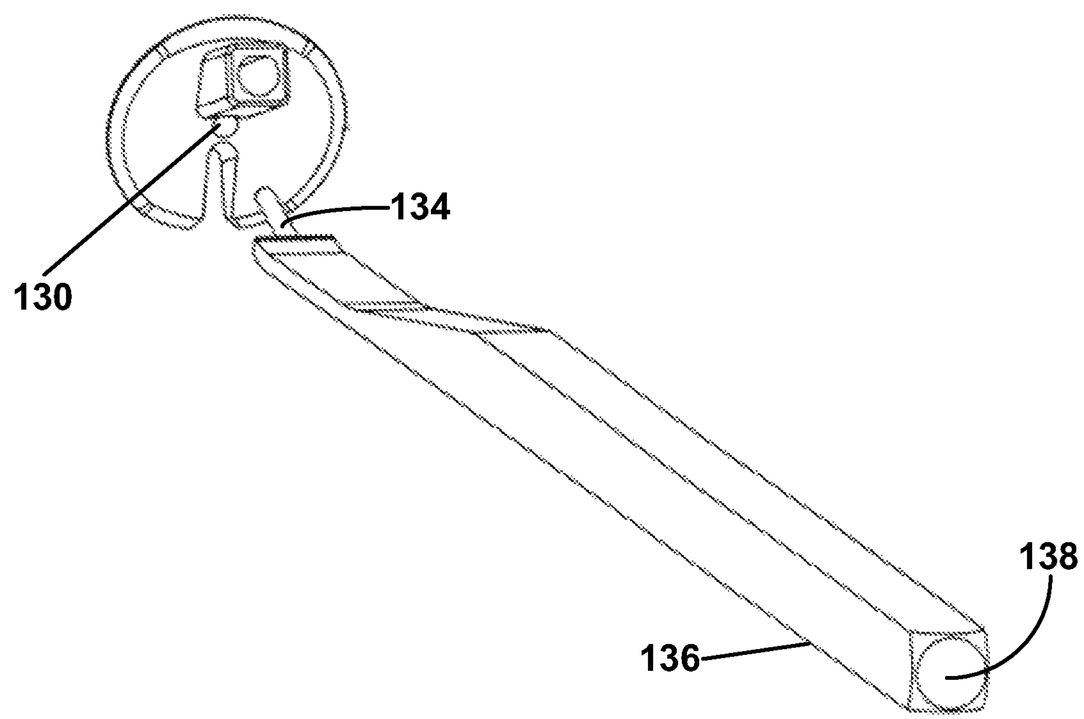
FIG. 21 illustrates a perspective view of another embodiment of an impact guide and an impact device.

Once an impact guide has been selected based on, for example, the size of the excision site, the impact guide head 124 may be seated in the excision site 70 as illustrated in the embodiment of FIG. 20. In one embodiment, the guide pin 56 may optionally be removed before or after seating the selected impact guide head 124. The impact guide head 124 may include an impact slot 130 defined therein. As illustrated in FIG. 20, the impact slot 130 is generally rectangular in cross-section; however, as may be appreciated, other cross-sectional geometries may be provided, such as circular, as illustrated in FIG. 21, as well as elliptical shaped, square shaped, etc. An impact device 132, such as a chisel, punch or awl may be provided, the distal end 134 of which may fit in and extend through the impact slot 130. Therefore, in some embodiments, the distal end may be longer than the length of the impact slot. In addition, the distal end of the impact device 132 may exhibit a cross-sectional area that may be slightly smaller than that of the impact slot 130. The proximal end 136 of the impact device 132 may provide a striking surface 138, which may be hit by hand, or with a hammer or other device, causing the impact device 132 to extend through the impact slot 130 creating a secondary excision site 140 in the primary or first excision site 70. In some embodiments, the impact device may include a sagittal saw or other cutting device, which may be inserted through the impact slot 130. If the guide pin 56 has not yet been removed, it may be removed at this time.

While the proximal end 136 of the impact device 132 is illustrated in FIG. 20 as being provided at an angle γ to the arm 122 of the impact guide 120, wherein angle γ may be in the range of 15 degrees to 120 degrees, including all values and increments therein, in some embodiments, the impact device 132 may be inserted closer to the impact guide 120, wherein angle γ may be in the range of 0 degrees to 45 degrees, including all values and increments therein. In other embodiments, the proximal portion 136 of the impact device may be generally parallel to the arm 122 of the impact guide 120. In such a manner, the impact device 132 may be inserted into incision 49 in the patient (FIG. 6) without the need for expanding the size of the incision 49 greater than necessary to accommodate the head of the excision guide or the head of the impact guide. Further, the impact device 132 may include a curvature 137, which may generally fit over the curvature 123 of the arm 122 of the impact guide 120.

Figure 22:
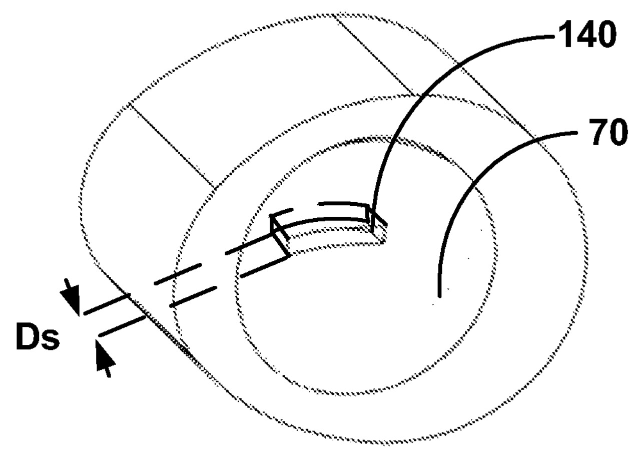
FIG. 22 illustrates a perspective view of an example of a secondary excision site provided in the bottom of a first or primary excision site.
Figure 23:
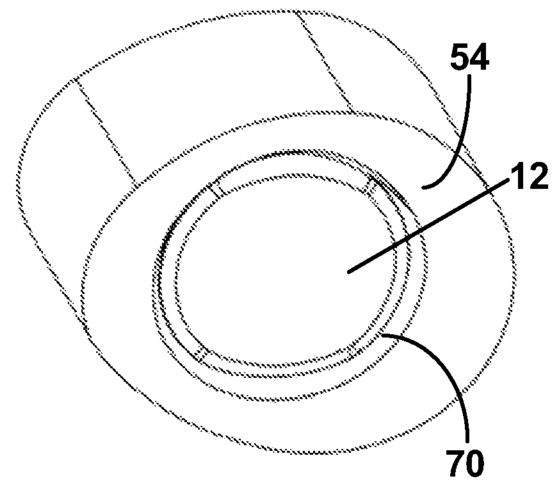
FIG. 23 illustrates an example of a perspective view of an implant positioned in an excision site.

FIG. 22 illustrates an embodiment of a secondary excision site 140 provided in an excision site 70. The secondary excision site 140 is illustrated as being generally rectangular; other cross-sectional geometries may be provided as well. In addition, the depth $D_s$ of the secondary excision site (illustrated in broken lines) may be formed to generally correspond with protrusions 34, 42, 44*a-d* that may extend from the keel 32 of the bone facing surface of the implant 12, illustrated in the embodiments of FIGS. 4 and 5*a-f*.

While the implant 12 may be held in place in some examples through a mechanical fit, such as through an interference fitbone adhesive may be used to secure the implant 12 in place in other embodiments. In such a manner a layer of bone adhesive may be delivered to the excision site 70, and optionally to the secondary excision site 140 and the implant 12 may be situated over the adhesive and positioned within the excision site.

Accordingly, an aspect of the present disclosure relates to a system for repairing a defect on a patient's articular surface. The system may include a guide pin configured to be secured into an articular surface of a glenoid, an excision guide and an excision device.

The excision guide may include a guide head wherein the guide head includes a contact surface configured to locate the excision guide relative to the articular surface. In some embodiments, the guide head may be configured to be positioned generally central on the articular surface. The excision guide may also include a guide sleeve disposed on the guide head. The guide sleeve may be configured to receive the guide pin therethrough and position the guide pin at an angle β relative to an axis generally normal and central to a defect on the articular surface, wherein angle β is less than 90 degrees. In some embodiments, angle β may be in the range of 10 degrees to 90 degrees. In further embodiments, angle β may be in the range of 10 degrees to 30 degrees. The guide sleeve may also be configured to radially offset a point of entry the guide pin into the articular surface from the axis. The excision guide may further include an excision guide arm affixed to the guide head and a handle affixed to the guide arm.

The excision device may include a cannulated shaft and at least one cutter. The cannulated shaft may be configured to be advanced over the guide pin. The at least one cutter may be configured to form a generally hemi-spherical excision site in the articular surface.

A further aspect of the present disclosure relates to a system for repairing a defect on a patient's articular surface. The system may include a guide pin configured to be secured into an articular surface of a glenoid, an impact guide and an impact device.

The impact guide may include an impact guide head having an upper portion and a lower portion. In some embodiments, the impact guide head may have a height Ht that corresponds to a height H of an implant configured to be received in the excision site. In some embodiments, the impact guide head may have a radius Rt that corresponds to a radius Ri of an implant configured to be received in the excision site. In further embodiments, the impact guide head may be releasably coupled to an impact guide arm.

The impact guide head may also have a guide notch defining a first opening through the impact guide head from the upper portion to the lower portion of the impact guide head. The impact guide head may also include a periphery and the first opening may extend to the periphery. The guide notch may be configured to receive the guide pin.

The impact guide may also include an impact slot defining a second opening through the impact guide head from the upper portion of the impact guide head to the lower portion of the impact guide head. The lower portion of the guide head may be configured to be received in an excision site of the articular surface.

The impact device may be configured to be received in and extend through the impact slot. The impact device may include a proximal end and a distal end, wherein the proximal end includes a striking surface and the distal end is configured to be received in and extend through the impact slot. In some embodiments, the impact device may include a chisel. The impact device may be positioned at an angle γ relative to the impact guide arm, wherein angle γ is in the range 0 degrees to 45 degrees. The impact guide may also includes an impact guide arm and the impact device may include a proximal end and a distal end, and the proximal end of the impact device may be configured to be disposed generally parallel to the impact guide arm when the distal end is received in the impact slot.

Another aspect of the present disclosure relates to a method for repairing a defect on a patient's articular surface. The method may include positioning on an articular surface an excision guide, wherein the excision guide includes a guide head and a guide sleeve disposed on the guide head, wherein the guide head may includes a contact surface configured to locate the excision guide relative to the articular surface. The method may also include advancing a guide pin through the guide sleeve, wherein the guide sleeve is configured to receive the guide pin therethrough and position the guide pin at an angle β relative to an axis generally normal and central to a defect on the articular surface, wherein angle β is less than 90 degrees. The guide pin may then be secured to the articular surface.

The method may also include advancing an excision device over the guide pin, wherein the excision device includes a cannulated shaft and at least one cutter. A generally hemi-spherical excision site may be formed in the articular surface with the cutter. A secondary excision site may also be formed within the generally hemi-spherical excision site in which a portion of the implant may be positioned.

In some embodiments, the method may include advancing an impact guide over the guide pin, wherein the impact guide includes an impact guide head, a guide notch defined in the impact guide head and an impact slot defined in the impact guide head, wherein the guide notch may be configured to receive the guide pin. The impact guide head may then be located in the excision site.

As mentioned above, the present disclosure is not intended to be limited to a system or method which must satisfy one or more of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure.

What is claimed is:

1. A system for repairing a defect on a portion of an articular surface of a patient's glenoid, said system comprising:
- a guide pin to be secured into said articular surface of said glenoid proximate to said defect:
- an excision device comprising:
  - a cannulated shaft to be advanced over and rotated about said guide pin; and
  - one or more cutters having a generally arcuate shape to form a generally hemi-spherical primary excision site in a portion of said glenoid articular surface having a diameter generally corresponding to a diameter of an implant, wherein all of said one or more cutters extend outward from said cannulated shaft and are generally aligned in a single plane extending along a longitudinal axis of said cannulated shaft; and
- a guide including:
  - a guide arm; and
  - a guide head including:
    - an upper portion and a lower portion; and
    - a passageway including at least one interior surface, said at least one interior surface extending through said guide head from said upper portion to said lower portion at an angle β less than 90 degrees relative to an axis generally normal and central to said guide head, wherein said at least one interior surface is to receive said guide pin and extends through said guide head such that an entry point of said guide pin into said glenoid articular surface is offset from said axis generally normal and central to said guide head and such that said excision device, when advanced over said guide pin, forms said generally hemispherical primary excision site having a center that is generally coaxial with a center of said guide head and said axis.

2. The system of claim 1, wherein said passageway extends to periphery of the guide head.

3. The system of claim 1, wherein said guide head is releasably coupled to said guide arm.

4. The system of claim 1, wherein said guide head has a height Ht that corresponds to a height H of said implant configured to be received in said primary excision site.

5. The system of claim 1, wherein said guide head has a radius Rt that corresponds to a radius Ri of said implant configured to be received in said primary excision site.

6. The system of claim 1, further comprising an impact device comprising a proximal end and a distal end, wherein the proximal end includes a striking surface and said distal end is configured to be received in and extend through an impact slot extending through said guide head from said upper portion to said lower portion.

7. The system of claim 6, wherein said impact device includes a chisel.

8. The system of claim 6, wherein said impact slot is configured to arrange said impact device at an angle γ relative to the guide arm, wherein angle γ is in the range 0 degrees to 45 degrees.

9. The system of claim 6, wherein said proximal end of said impact device is configured to be disposed generally parallel to said guide arm when distal end of said impact device is received in said impact slot.

10. The system of claim 1, further comprising an impact slot disposed generally between said passageway and said guide arm, said impact slot defining an opening through said guide head from said upper portion to said lower portion.

11. The system of claim 1, wherein said passageway further includes a guide sleeve defining said at least one interior surface, said guide sleeve configured to receive said guide pin therethrough.

12. The system of claim 1, wherein an interior surface of said lower portion of said guide is recessed relative to a periphery of said guide head.

13. The system of claim 1, wherein at least a portion of said lower portion of said guide is configured to contact said primary excision site.

14. The system of claim 1, further comprising said implant configured to be received within said primary excision site centered about said axis such that at least a portion of a load bearing surface of said implant is generally flush with a remaining portion of said glenoid articular surface at least partially surrounding said implant.

15. The system of claim 14, wherein said guide head has a height Ht that corresponds to a height H of said implant.

16. The system of claim 14, wherein said guide head has a radius Rt that corresponds to a radius Ri of said implant.

17. The system of claim 14, wherein said one or more cutters have a radius that corresponds to a radius Ri of said implant.

* * * * *